(12) United States Patent
Fellmann et al.

(10) Patent No.: US 8,901,288 B2
(45) Date of Patent: Dec. 2, 2014

(54) HIGH THROUGHPUT METHODS FOR FUNCTIONALLY DETERMINING RNA INTERFERENCE EFFICIENCY

(75) Inventors: Christof Fellmann, Cold Spring Harbor, NY (US); Scott W. Lowe, Cold Spring Harbor, NY (US); Gregory J. Hannon, Huntington, NY (US); Johannes E. Zuber, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 470 days.

(21) Appl. No.: 12/739,382

(22) PCT Filed: Oct. 24, 2008

(86) PCT No.: PCT/US2008/081193
§ 371 (c)(1),
(2), (4) Date: Sep. 14, 2010

(87) PCT Pub. No.: WO2009/055724
PCT Pub. Date: Apr. 30, 2009

(65) Prior Publication Data
US 2011/0015093 A1 Jan. 20, 2011

Related U.S. Application Data

(60) Provisional application No. 61/000,538, filed on Oct. 26, 2007.

(51) Int. Cl.
*C07H 21/00* (2006.01)
*C12Q 1/68* (2006.01)
*C12N 15/10* (2006.01)

(52) U.S. Cl.
CPC .......... *C12N 15/1086* (2013.01); *C12Q 1/6897* (2013.01)
USPC ...................................................... 536/24.5

(58) Field of Classification Search
None
See application file for complete search history.

(56) References Cited

U.S. PATENT DOCUMENTS

| 5,672,485 A | 9/1997 | Foster et al. | |
| 2005/0042641 A1* | 2/2005 | Mittal et al. | 435/6 |
| 2006/0123494 A1 | 6/2006 | Wu et al. | |
| 2006/0135456 A1 | 6/2006 | Hannon et al. | |
| 2006/0212950 A1* | 9/2006 | Tuschl et al. | 800/14 |
| 2007/0044164 A1 | 2/2007 | Dickins et al. | |

FOREIGN PATENT DOCUMENTS

WO    WO 2006/063786    *  6/2006  ............. C12N 15/64

OTHER PUBLICATIONS

Lee, et al. (2003) Translation Start Sequences Affect the Efficiency of Silencing of *Agrobacterium tumefaciens* T-DNA Oncogenes. Plant Physiology, v.133:966-77.*
NCBI Entrez Accession No. U55761 [online]. [Retrieved on Dec. 14, 2012]. Retrieved from the Internet: <http://folk.uio.no/torgeirh/plasmidlibrary/pEGFP-1.html>.*
International Search Report and Written Opinion mailed on Mar. 23, 2009 for International Patent Application No. PCT/US2008/081193, filed Oct. 24, 2008.
Urlinger et al., "Exploring the sequence space for tetracycline dependent transcriptional activators: Novel mutations yield expanded range and sensitivity," PNAS, vol. 97, pp. 7963-7968 (2000).
Fellmann et al., "Functional identification of optimized RNAi triggers using a massively parallel sensor assay," Molecular Cell, vol. 41, pp. 733-746 (Mar. 2011).
Castanotto et al., "Sensor and Sensitivity: A screen for elite shRNAs," Molecular Therapy, vol. 19, pp. 823-825, (May 2011).

* cited by examiner

*Primary Examiner* — Jennifer McDonald
(74) *Attorney, Agent, or Firm* — Wilmer Cutler Pickering Hale and Dorr LLP

(57) ABSTRACT

Provided is a single construct combining a sequence encoding an RNAi molecule, a sequence encoding a reporter, and a target sequence specific for the RNAi molecule. The construct can be used to determine the potency of the encoded RNAi molecule in a direct and unbiased way. These results can be used to inform the design of potent RNAi molecules of various types and can be extended to several other applications, including: (1) generation of tiled libraries comprising every possible RNAi molecule-encoding sequence for a given gene target; (2) large-scale parallel validation of RNAi molecules targeting many genes to generate validated RNAi molecule-encoding libraries; (3) experimental comparison of design algorithms and strategies; and (4) investigation of RNAi biology in target site mutagenesis assays by screening pools containing single nucleotide changes in target sites and/or in the RNAi molecule to identify the most relevant sequence characteristics of potent RNAi-target site predictions.

36 Claims, 35 Drawing Sheets

US 8,901,288 B2

HIGH THROUGHPUT METHODS FOR FUNCTIONALLY DETERMINING RNA INTERFERENCE EFFICIENCY

Figure 1:
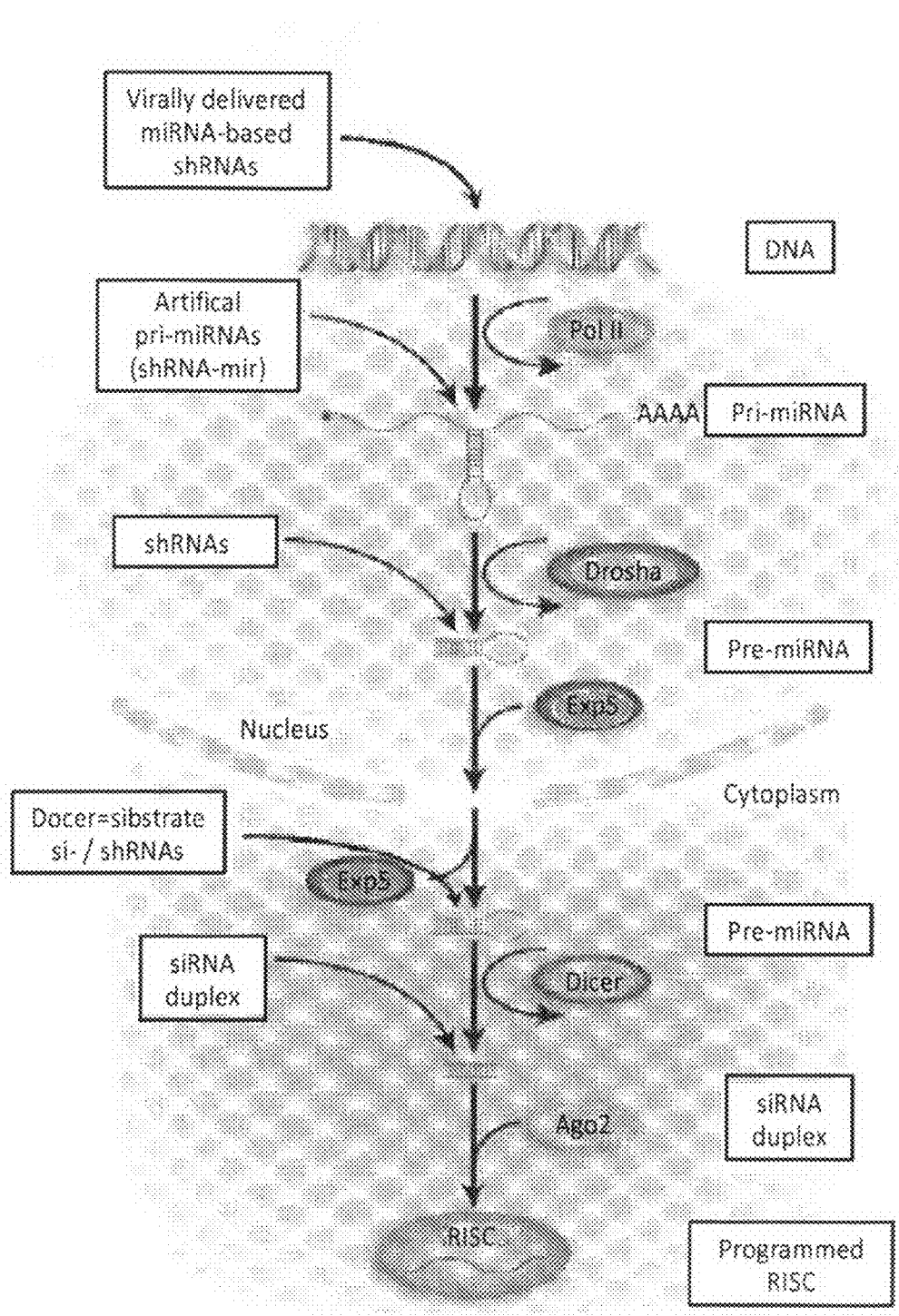

This application is a U.S. National Phase Application under 35 U.S.C. §371 of International Patent Application No. PCT/US2008/081193 filed Oct. 24, 2008, and published as WO 2009/055724 on Apr. 30, 2009, which claims the benefit of priority of U.S. Provisional Application Ser. No. 61/000, 538, filed Oct. 26, 2007, the disclosures of which are hereby incorporated by reference in their entireties.

This invention was made in part with government support under grant No. 5U01CA105388 awarded by the National Institutes of Health. The United States government may have certain rights in this invention.

SEQUENCE LISTING

The instant application contains a Sequence Listing which has been submitted via EFS-Web and is hereby incorporated by reference in its entirety. Said ASCII copy, created on May 23, 2012, is named 28700145.txt and is 1,377 bytes in size.

1. BACKGROUND OF THE INVENTION

The advent of RNA interference has opened new horizons in molecular biology by enabling specific suppression of the function of virtually any gene. RNAi is a sequence-specific posttranscriptional gene silencing mechanism triggered by double-stranded RNA (dsRNA). It causes degradation or translational repression of mRNAs complementary in sequence to the dsRNA. Effective inhibition by the RNAi pathway requires the identification of functional small interfering RNAs (siRNAs) or short hairpin RNAs (shRNAs). To this end, prediction algorithms based on various design rules have been implemented and, recently, improved by the use of artificial neural networks. Nevertheless, these algorithms often fail to correctly forecast si- or shRNA potency.

A number of shRNA libraries have been constructed to date (see, e.g., Bernards et al., (2006), *Nature Methods* 3, 701-706; Chang et al. (2006), *Nature Methods* 3, 707-714). But one of the most challenging problems for creating an interfering RNA molecule library is the identification of effective and specific interfering RNA molecules. Potent interfering RNA molecules are needed because partial knockdown does not lead to clear loss-of-function effects. Experimental evidence has shown that differences as subtle as a one base pair (bp) shift on the target mRNA can turn a potent interfering RNA molecule into a weak one.

Design rules have been established by researchers for the creation of effective and specific si- or shRNAs (reviewed in Pei and Tuschl (2006), *Nat. Methods* 3, 670-676). The most important features include the thermodynamic asymmetry of the RNA duplex, sequence homology of the seed sequence to its cognate target mRNA but not to other mRNAs, and a set of single nucleotide positional preferences. These and further understandings of the RNAi mechanism have been integrated into computer algorithms for in silico prediction of effective and specific shRNAs. Although these programs have improved the design of duplex RNAs, they are nonetheless imperfect. Not every predicted interfering RNA meets the desired thresholds of potency and specificity, so that experimental proof of target protein knockdown remains indispensable. In fact, as part of the findings of this disclosure, it was determined that existing libraries created by such prediction algorithms showed that about 80% of these shRNAs fail to confer efficient target knockdown.

In an effort to improve the design of potent RNAi triggers, various in-silico algorithms and computational tools have been established over the last years. Birmingham et al. ((2007), *Nature Protocols* 2: 2068-2078) provide a comprehensive overview of existing RNAi design algorithms. For example, BIOPREDsi was developed based on an empirically trained neural network (Huesken et al. (2005), *Nat. Biotechnol.* 23, 995-1001) and considerably improved the rate of correct predictions. Nevertheless, predictions derived from these algorithms are still not perfect, but typically contain a mix of functional and non-functional RNAi triggers. Therefore, the identification of functional and potent RNAi triggers still requires individual experimental evaluation of each predicted RNAi trigger prior to use in downstream applications. To improve this limitation, it is desirable to develop new experimental approaches to identify effective RNAi triggers, which could complement or even replace rule-driven selection strategies.

Current experimental validation tactics include Western blots, quantitative reverse-transcription polymerase chain reactions (qRT-PCR), mass spectroscopy, and reporter assays. Western blots are advantageous in that they directly measure protein content and are, therefore, one of the most reliable methods, since they report shRNA effects on transcriptional and translational levels. But specific antibodies are not always available, and can be laborious or impossible to produce. In addition, the tagging of a specific gene with e.g., Flag-tags or His-tags, requires intensive cloning steps and is not applicable to endogenous genes. While qRT-PCR may be broadly applicable and can be relatively easy to perform, the downside of this technology is that no precise quantitative readouts can be obtained because only transcriptional effects are reported. Furthermore, both Western blots and qRT-PCR are gene-specific assays. Thus, only parallel but no high-throughput approaches are currently feasible. To a certain degree, mass spectroscopy allows for high-throughput methods and also directly determines protein levels. However, quantification is difficult, especially for non-abundant proteins that often require purification procedures in addition to knowledge about the specific peptide patterns.

The majority of published shRNA reporter assays employ plasmids carrying mRNA target sequence/reporter gene fusions that are co-introduced into cells with the target-specific sh- or si-RNA (reviewed in Pei and Tuschl, 2006, supra; Smart et al. (2005) *Biol. Proced. Online* 7: 1-7). Such reporter assays may report shRNA activity on the transcriptional and translational levels, but are unsuited for high-throughput methods. Instead, these assays, which often require extensive cloning, are aimed at testing the effect of different sh- or siRNAs directed against a single target mRNA.

Thus, there is a need in the art for a high-throughput in vitro method for rapidly and simultaneously testing, identifying, and ranking interfering RNA molecules that target different sequences. In addition, there is a need for a method to identify target sequences for RNA interference, which can then be used to inform RNAi design for therapeutic applications in human and veterinary medicine.

2. SUMMARY OF THE INVENTION

In biological, biomedical, and/or clinical applications, it is important to identify the most potent RNAi molecules for a given target gene. It is equally important to identify targets that are most amenable to RNA interference. Current design algorithms can enrich for functional RNAi molecules, but do not allow for an accurate prediction of potency, for example, as measured by target protein knockdown levels. Current design algorithms also fail to rule out dysfunctional predictions (i.e., RNAi molecules that fail to adequately suppress target gene expression). Thus, the present invention provides a system for functionally determining the efficiency of RNA interference in a high-throughput manner, thereby providing RNAi molecules experimentally tested for high potency. The present invention also provides a system for evaluating target genes for RNA interference and informing RNAi design.

The core of the invention is the combination, on one construct, of a sequence encoding an RNAi molecule, a sequence encoding a reporter, and a target sequence that is specific for the RNAi molecule (cognate target sequence), and the use of the construct to determine the potency of the encoded RNAi molecule in a direct and unbiased way. These results can be used to inform the design of potent RNAi molecules of various types and can be extended to several other applications, as described below. The method can be applied in high-throughput functional screening of up to every possible RNAi molecule for a given gene target due to at least two aspects: (1) coupling, i.e., both the RNAi-molecule encoding oligonucleotide, and its cognate target sequence, are cloned into the same vector, and (2) pooled cloning, i.e., all desired RNAi-molecule encoding sequence-target sequence pairs, are cloned together into an expression-reporter vector, as opposed to single cloning where each different RNAi-molecule encoding oligonucleotide is cloned separately from its target. Pooled cloning therefore comprises large pools of RNAi-encoding molecules (i.e., at least about twenty thousand, thirty thousand, forty thousand or more different sequences) and their cognate targets, which are cloned simultaneously, in a single reaction. The approach of the present invention has several applications, including: (1) generation of tiled libraries that comprise every possible RNAi-molecule encoding sequence for a given gene target; (2) large-scale parallel validation of RNAi molecules targeting many genes to generate validated RNAi-molecule encoding libraries; (3) experimental comparison of design algorithms and strategies; and (4) investigation of RNAi biology in target site mutagenesis assays by screening pools containing single nucleotide exchanges, insertions, or deletions in target sites and/or the RNAi molecule to identify the most relevant sequence characteristics of potent RNAi-target site predictions.

In one aspect, the invention provides plasmids or reporter constructs for testing the potency or efficacy of an RNAi molecule, such plasmids or constructs comprising minimally, a promoter; a sequence encoding an RNAi molecule, operably linked to the promoter, and a target sensor comprising (i) a sequence encoding a reporter and (ii) a target sequence that comprises from about 8 to about 29 contiguous nucleotides complementary to at least a portion of the guide strand of the RNAi molecule. In a preferred embodiment, the sequence in the reporter construct encodes an shRNA.

The target sequence is located in the target sensor in a region that does not compromise function of the reporter. For example, the target sequence can be located in an untranslated region (UTR) of the reporter sequence, such as in the 5' UTR or the 3' UTR. The target sequence can also be located in a translated region of the reporter sequence, provided that the reporter remains functional. In preferred embodiment, the target sequence comprises about a 19 to about a 22 nucleotide sequence. In one embodiment, the target sequence is about 19 to about 22 nucleotides.

In another aspect, the invention provides a construct comprising, in 5' to 3' order: (a) a first promoter; (b) a sequence encoding an RNAi molecule, which is under the transcriptional control of the first promoter; (c) a second promoter; (d) a sequence encoding a reporter that is under the transcriptional control of the second promoter; and (e) a target sequence that comprises from about an 8 to about a 29 nucleotide sequence that is complementary to at least a portion of the guide strand of the RNAi molecule, such that the target sequence is part of the same mRNA transcript of the reporter sequence.

The promoter is typically a ubiquitous, cell-type specific, or tissue specific promoter. The promoter can be constitutive or conditional. For example, a tetracycline-responsive element (TRE) expression system uses an inducible Tet-responsive promoter. In a Tet-On system, the promoter is inducible, for example by the addition of tetracycline (Tet) or, more commonly, its derivative, doxycycline (Dox), in a cell that expresses the rtTA reverse Tet-transactivator. The rtTA binds to the Tet-operator sequence (tetO; part of the TRE promoter) when complexed with Dox, whereby it promotes transcription from the TRE promoter. A "TRE promoter" is an inducible promoter suitable for use in a Tet-responsive expression system.

The sequence encoding an RNAi molecule is also referred to as an RNAi coding sequence. The coding sequence can be, for example, a sequence that encodes an shRNA molecule. For example, the shRNA molecule can comprise a double-stranded RNA region that is about 16-29 nucleotides in length. In one aspect, the double-stranded RNA region of an shRNA molecule (i.e., the stem), is about 25 to about 29 nucleotides in length (each strand of the stem). In one aspect, the sequence that when transcribed forms the shRNA molecule comprises miR-30 sequences (an miR-30 backbone), except at least for the sequences that code for the duplex stem region of the shRNA molecule. In one aspect, the non-miR-30 sequence comprises the stem region in addition to the loop region of the shRNA. Coding sequences for shRNA molecules can be designed according to the teachings expressed in Hannon et al. (U.S. Publication No. 2006/0135456), Hannon et al. (International Publication No. WO2006/073601), and Dickins et al. (U.S. Publication No. 2007/0044164), the contents of which are hereby incorporated by reference.

In one aspect, the reporter construct comprises an additional reporter that is under the transcriptional control of the promoter that controls transcription of the RNAi molecule. As used herein, a "reporter sequence" includes a selection gene. The additional reporter sequence reports shRNA expression. In addition, the additional reporter can provide a spacer between the promoter and the sequence encoding the RNAi, which can make the RNAi more potent. When a selection gene is used, the viability of the cell can be based upon the expression of the selection gene. For example, the selection gene can code for neomycin resistance such that cells that do not possess reporter constructs will die in the presence of neomycin. Alternatively, the additional reporter sequence can code for a fluorescent protein that emits a different emission wavelength than the reporter sequence containing the target sequence. For example, the additional reporter sequence could be dsRed2, or a yellow fluorescent protein, or a blue fluorescent protein, and the reporter sequence containing the target sequence could be a green fluorescent protein.

In another embodiment, the reporter sequence is a lethal gene, wherein shRNA-mediated suppression of the lethal gene results in survival of cells infected with potent shRNAs. Alternatively, the reporter sequence encodes a surface antigen, and the population of RNAi molecules is exposed to a substrate coated with an antibody against the surface antigen. Cells containing weak RNAi molecules bind to the substrate, while those containing potent RNAi molecules remain unbound due to suppressed expression of the surface antigen.

The delivery system need only have the features that it allows (1) stable, single-copy genomic integration in reporter cells, and (2) cloning of large shRNA/target libraries. In one aspect, the reporter construct is a viral construct in the sense that it comprises flanking long terminal repeats (LTRs) and a packaging sequence. For example, the reporter construct can comprise a 5'LTR of a virus located upstream of the first promoter, a packaging signal located downstream of the 5'LTR and upstream of the first promoter, and a 3'LTR of a virus located downstream of the target sensor. In one aspect, the LTRs and the packaging signal are from a retrovirus, such as a murine stem cell virus (MSCV), and are preferably from a lentivirus. The sequences can also be from an avian virus or other suitable virus.

In one aspect, the invention provides a reporter construct comprising in 5' to 3' order the following features: (1) a retroviral 5'LTR, (2) a retroviral packaging signal, (3) an inducible promoter, (4) a selection gene whose transcription is controlled by the inducible promoter, (5) a sequence that codes for an RNAi molecule whose transcription is controlled by the inducible promoter, (6) a constitutive promoter, (7) a sequence encoding a reporter whose transcription is controlled by the constitutive promoter, (8) a target sequence that comprises about an 8 to about a 29 nucleotide sequence that is complementary to at least a portion of the guide strand of the RNAi molecule encoded by the sequence of (5), such that the target sensor sequence is part of the same mRNA transcript of the reporter, and (9) a retroviral 3'LTR. In a preferred embodiment, the retroviral 3'LTR is self-inactivating.

In a further aspect, the invention provides an RNAi library comprising a plurality of reporter constructs according to any aspect or embodiment of the invention, wherein each reporter construct in the plurality is identical except for the sequence encoding the RNAi molecule (and, consequently, the target sequence).

In one aspect, the RNAi library is a tiled library, where every possible guide sequence of a given target gene is represented in part of the RNAi coding sequences in the reporter constructs. As the RNAi coding sequences are coupled to the target sequences, the RNAi library also comprises every possible target sequence (of a given length, for example, 22 nucleotides) of a given target gene. The RNAi library that comprises reporter constructs can be tiled for more than one gene target. In one aspect, the RNAi library comprises at least 50, 100, 500, 1000, 5000, 10000, 20000, 60000, or 100000 or more different RNAi coding sequences. In one aspect, the RNAi library can comprise a library of sequences designed on the principles of algorithms. In one aspect, the RNAi library can comprise the most potent RNAi sequences as predicted by algorithms such that these sequences are tested or validated for their functional efficacy by the present methods.

The invention also provides a method of determining the potency or efficacy of RNAi molecules with respect to their ability to knock-down expression of gene via RNA interference, such that the guide sequence targets the target sequence. One method for determining the potency of an RNAi molecule comprises: (a) introducing a construct or an RNAi library according to any one of the aspects or embodiments of the invention into cells; and (b) determining the amount of reporter expression in the cells, wherein high reporter expression indicates a less potent RNAi molecule and low or no reporter expression indicates a more potent RNAi molecule.

In a particular aspect, the invention provides a method for determining the potency of RNAi molecules, the method comprising: (a) introducing into packaging cells an RNAi library that comprises reporter constructs that comprise: (i) a 5'LTR, (ii) a packaging signal, (iii) an inducible promoter that controls transcription of, (iv) a selection gene, and also (v) a sequence encoding an RNAi molecule, (vi) a constitutive promoter that controls transcription of (vii) a target sensor comprising (viii) a sequence encoding a reporter, which contains (ix) a target sequence that is complementary to at least a portion of one strand of the double-stranded region of the sequence encoding the RNAi molecule, and (x) a 3'LTR (preferably a self-inactivating 3'LTR), wherein the reporter constructs of the RNAi library are packaged into virions; (b) infecting a second population of cells with the virions; (c) sorting the cells based on reporter expression; and (d) determining the amount of reporter expression in the cells, wherein high reporter expression indicates a less potent RNAi molecule and low or no reporter expression indicates a more potent RNAi molecule.

The assessment of reporter expression can be qualitative or quantitative and can be comparative among a given population of cells expressing different RNAi molecules. The methods of the invention can be used not only to isolate the most potent RNAi molecules, but can also be used to identify RNAi molecules having different degrees of potency. The methods of the invention can also be used to identify target sequences for therapeutic and/or preventative clinical applications and to inform RNAi design for such applications.

The methods of the invention can further include the steps of separating cells exhibiting the greatest reduction in reporter expression; and determining the sequence of the RNAi molecules with the greatest inhibitory effects. In a preferred embodiment, cells are sorted based on the reversibility of reporter expression. The relationship between reversible reduction in reporter expression and potency of RNAi is direct, such that greater reversible reduction indicates more potent RNAi molecules. The methods can also include one or more additional steps selected from: adding to transformed cells an agent that activates transcription from an inducible promoter; adding to transformed cells a substance that causes the cells to die unless the cells are expressing a selection gene contained in the reporter construct; and sorting the transformed cells into different populations based on their degree of reporter expression, wherein the potency of the RNAi molecule for knocking-down gene expression inversely correlates to the degree of reporter expression. A "transformed cell" is one that has been genetically modified. Methods of introducing constructs into cells include, but are not limited to, liposome fusion (transposomes), viral infection, and routine nucleic acid transfection methods such as electroporation, calcium phosphate precipitation and microinjection.

After selection, enhanced back-sorting strategies can be conducted. In one aspect, Sensor ping-pong strategies are conducted on transformed cells to enrich for cell populations containing only reporter constructs that express potent RNAi molecules. In one aspect, the isolating and sorting is conducted by flow cytometry, preferably fluorescence-activated cell sorting.

The invention also provides a modified cell line comprising DF-1 chicken embryo fibroblasts (CEFs), wherein the DF-1 CEFs are genetically modified to express rtTA3 reverse tet-transactivator and EcoR ecotropic receptor, wherein the modified cell line enables single-copy genomic integration of tet-regulatable transgenes.

3. BRIEF DESCRIPTION OF THE FIGURES

FIG. 1. The miRNA pathway in vertebrate cells and its use as a tool for gene silencing. Artificial siRNAs can enter the miRNA pathway as: (1) ~21 nt synthetic siRNA duplexes; (2)

as ~27 nt Dicer-substrate siRNA duplexes; (3) as Dicer-substrate shRNA duplexes; (4) as stem-loop shRNAs mimicking pre-miRNAs; or (5) as miRNA-based shRNAs mimicking pri-miRNAs. See Kim et al., (2005), *Nat. Biotechnol.*, 23: 222-2261; Siolas et al., (2005), *Nat. Biotechnol.* 23: 227-231; and Silva et al., (2005), *Nature Genetics,* 37: 1281-1288; the contents of these papers are hereby incorporated by reference for all purposes. Strong target gene knockdowns are often achieved by viral delivery of miRNA-based shRNAs that are transcribed from RNA polymerase II promoters.

Figure 2A:
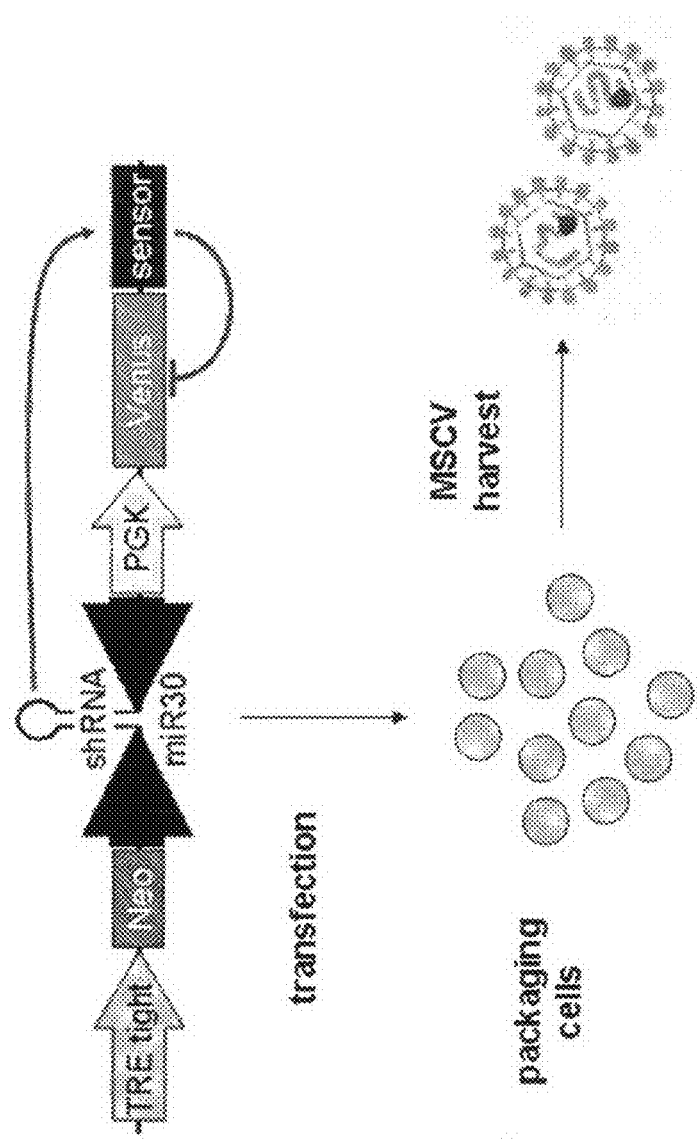
Figure 2B:
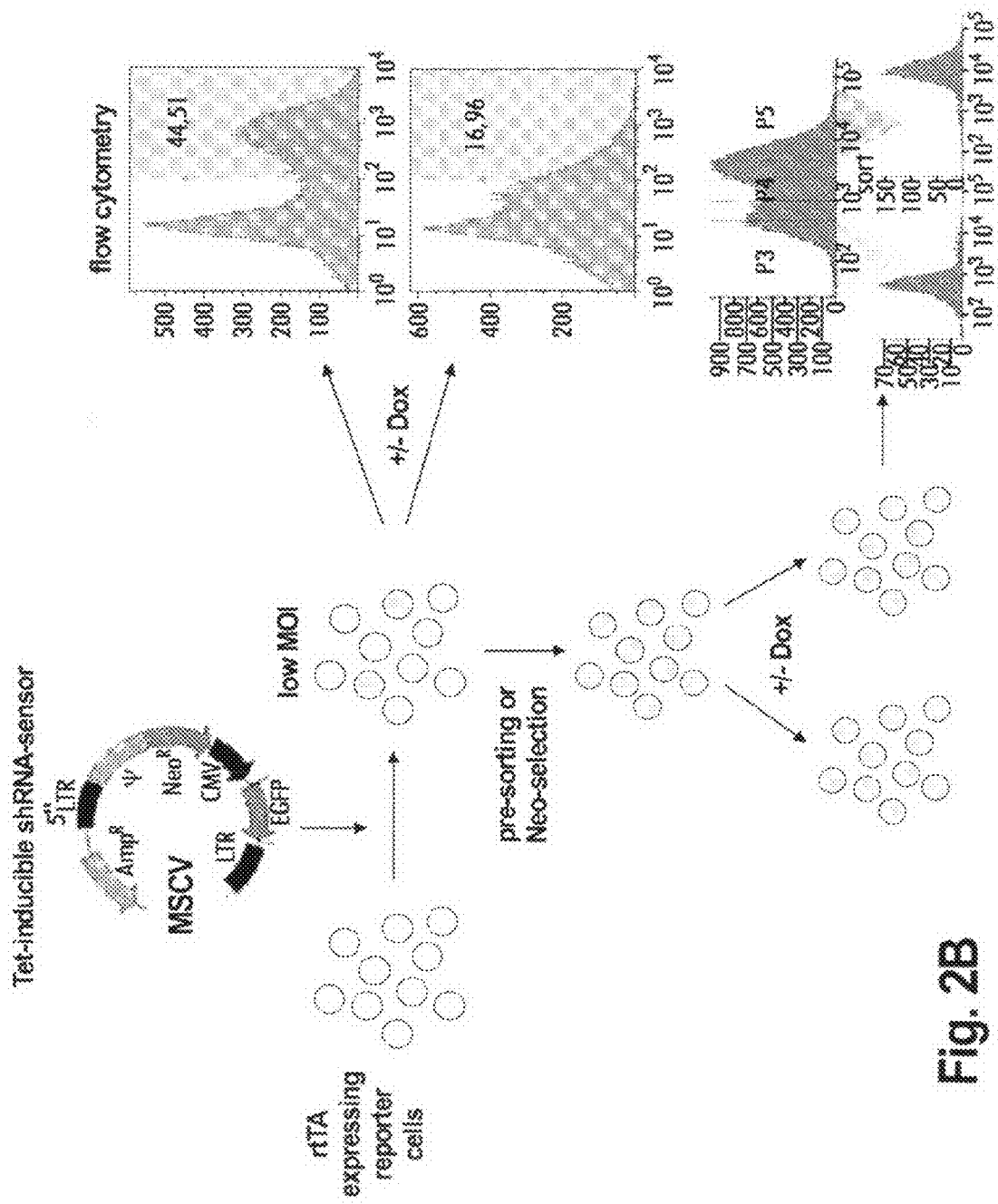

FIG. 2. Concept of an shRNA knockdown reporter assay. In this figure, an shRNA knockdown reporter assay comprises a fluorescent marker-target sensor construct integrated into a Dox-inducible retroviral shRNA expression vector. FIG. 2A shows an shRNA efficiency reporter vector being transfected into packaging cells (Phoenix HEK293T); retroviruses carrying the reporter construct are produced. FIG. 2B shows that the retroviral virions produced by the packaging cells are used to infect reporter cells that constitutively express the reverse tetracycline-controlled transactivator (rtTA), which, when bound to Dox, becomes an active transcription factor activating transcription on the TRE promoter. Subsequently, the cells can either be directly treated with or without Dox and analyzed and/or sorted on a flow cytometer, or first enriched for infected cells by Neo-selection or pre-sorting and then treated+/−Dox and analyzed/sorted.

FIG. 3. Characterization of TRMPV. The Dox-inducible retroviral vector TRMPV was characterized for its ability to conditionally express shRNAs in the Rosa-rtTA MEF cell line. FIG. 3A shows vector maps of the Tet-inducible vectors TRMPV, TRMPV with target sensor, and TtNmPV with target sensor. FIG. 3B shows an analysis of infection and induction efficiency of TRMPV in Rosa-rtTA MEFs. Quantification of cell sub-populations was done by flow cytometry (Guava EasyCyte). FIG. 3C shows a positive selection assay with a growth promoting p53 shRNA (sh.p53.1224) and a neutral luciferase shRNA (sh.Luci.1309) in Rosa-rtTA MEFs. Results were displayed either by plotting % GFP-positive cells or the cell number as a function of time. FIG. 3D shows a negative selection assay in Rosa-rtTA MEFs with partially lethal shRNAs against proliferating cell nuclear antigen (PCNA) and replication protein A3 (RPA3), as well as a neutral luciferase shRNA (sh.Luci.1309).

Figure 4A:
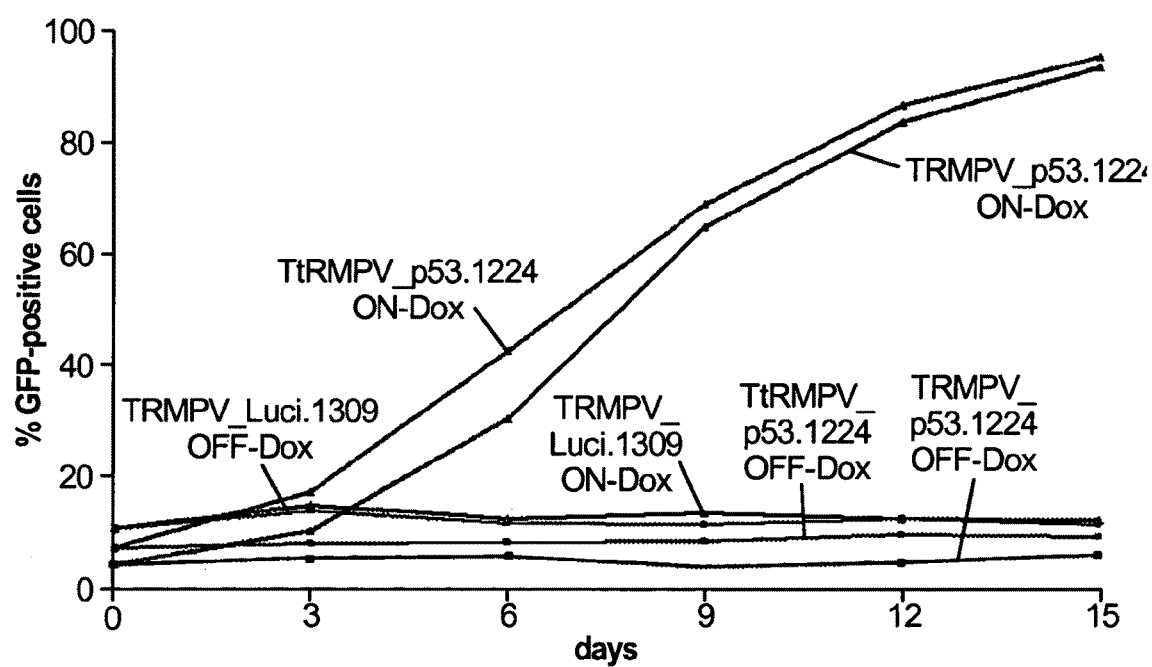
Figure 4B:
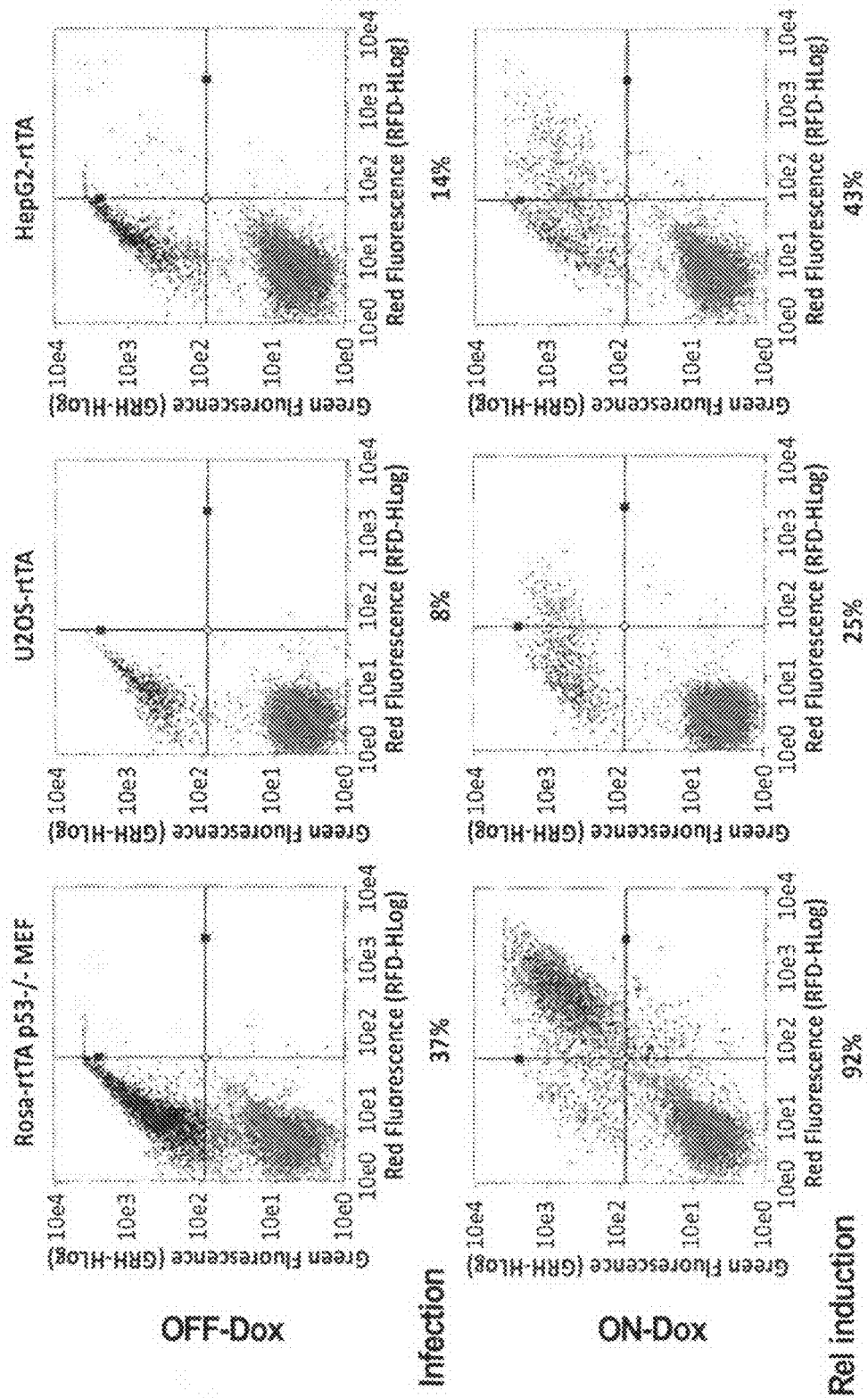
Figure 4C:
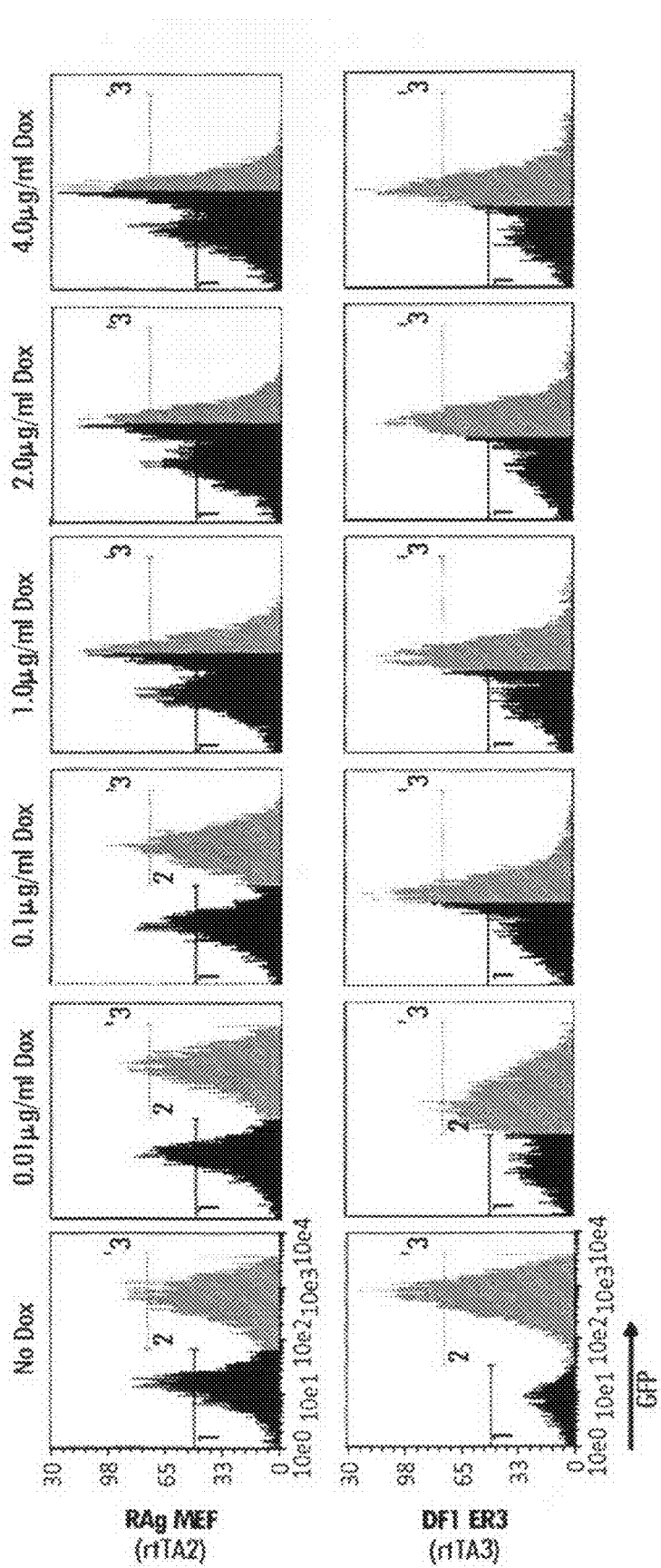

FIG. 4. Optimizing promoter and reporter cell line. FIG. 4A shows the results of a positive selection screen comparing basal activity and shRNA expression efficiency of two Dox-inducible promoters, TRE and TREtight (see Example 2). FIG. 4B shows infection and induction efficiency in U2OS-rtTA (Clontech), HepG2-rtTA (Clontech), and Rosa-rtTA p53$^{-/-}$ MEFs. Cells were treated for four days+/−Dox. Relative induction is calculated as the percentage of infected cells that express shRNAs. FIG. 4C shows evaluation of new DF1 ER3 reporter cell line. DF1 ER3s and RAg MEFs were infected at low MOI with TtNmPV sh&t Luci.1309 (excellent shRNA) produced in ecotropic Phoenix. Cells were treated for 4 days at different doxycycline concentrations. Green fluorescence intensity was quantified on a flow cytometer. The DF1 ER3 cell line expresses the rtTA3 reverse tet-transactivator that induces shRNA expression at much lower doxycycline concentrations than the rtTA2 reverse tet-transactivator expressed in the RAg MEFs.

Figure 5A:
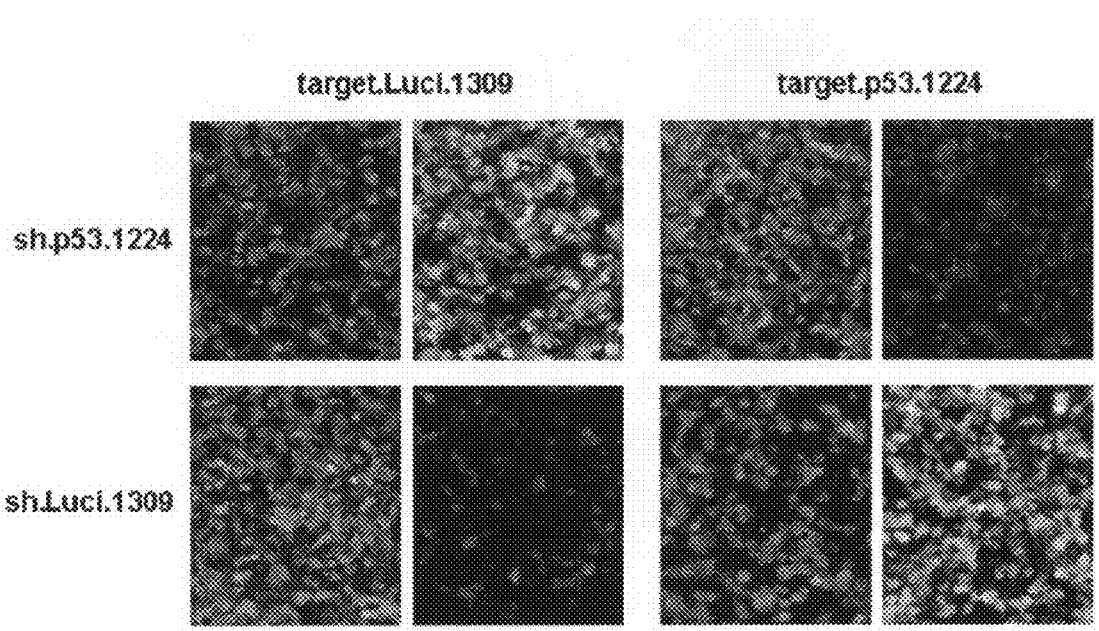
Figure 5B:
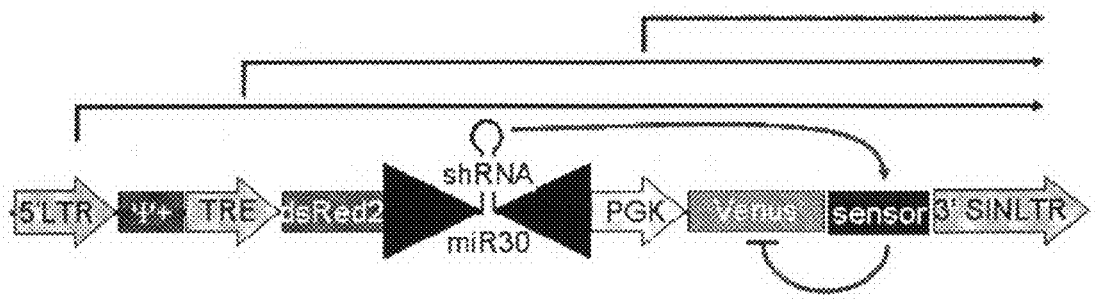
Figure 5C:
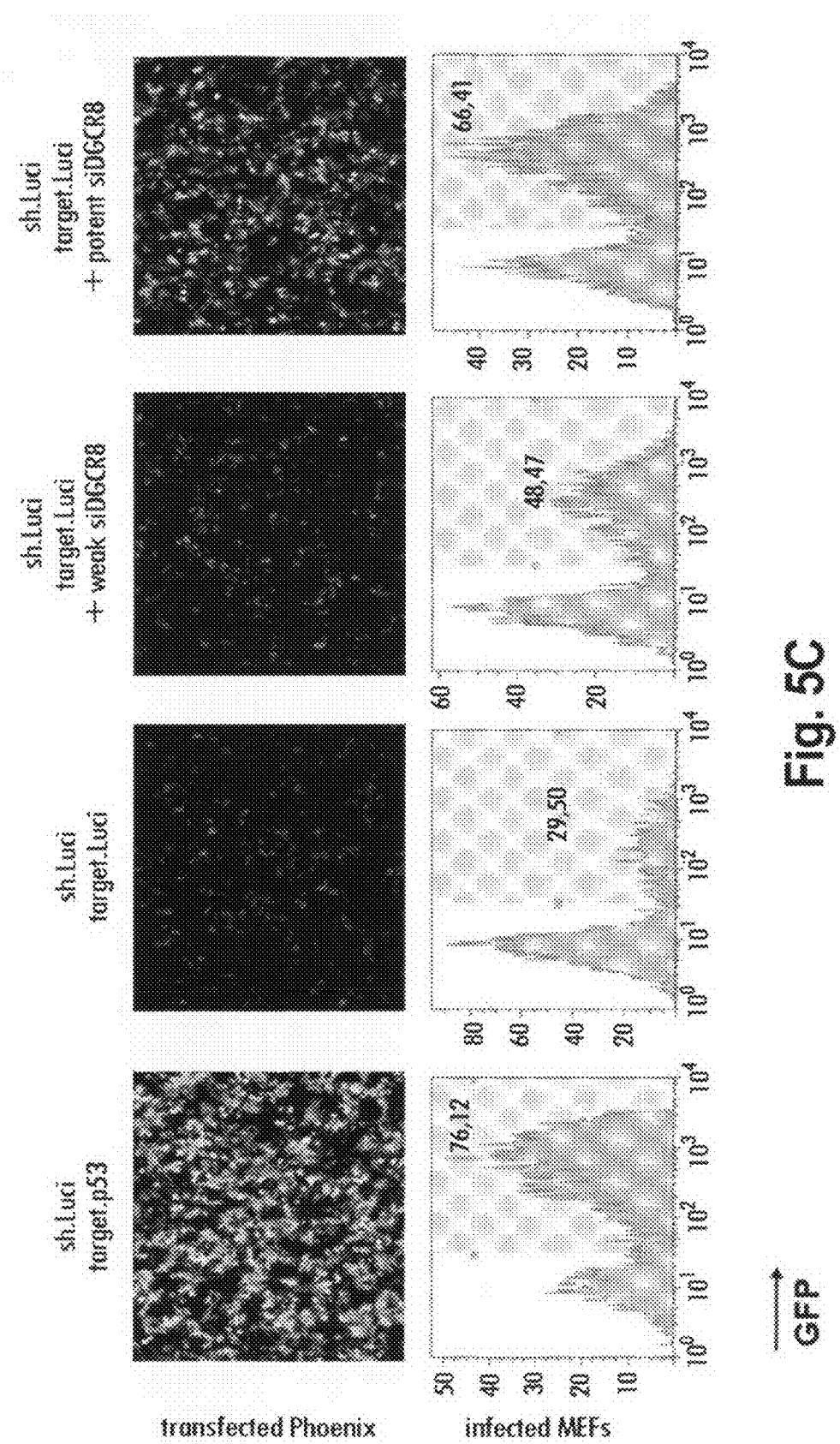

FIG. 5. Inhibition of the miRNA pathway in packaging cell lines reestablishes efficient viral packaging in presence of potent shRNA-sensor constructs. FIG. 5A shows ecotropic Phoenix (HEK293T) cells transfected with TRMPV sensor constructs containing one of two potent shRNAs (p53.1224, Luci.1309) expressed along with dsRed2 (red fluorescence) and either their cognate target sensor or the target sensor of the other shRNA. The target sensor is contained in the Venus (YFP, green fluorescence) transcript. Fluorescence microscopy images were taken 3 days after transfection. Presence of the correct target sensor (target p53.1224 for shRNA p53.1224, target Luci.1309 for shRNA Luci.1309) leads to dramatic reduction in Venus reporter gene expression, thereby proving that the sensor assay works. FIG. 5B shows a schematic representation of an exemplary reporter construct of the target sensor approach with the transcripts produced in transduced packaging cells. There are three independent transcripts in packaging cells: (i) the retroviral transcript driven by the LTR, which is the provirus, (ii) the leaky TRE transcript, which cannot be avoided, even with tighter promoters, since there will always be some leakiness due to the high number of copies in packaging cells, and (iii) the PGK-reporter-target sensor transcript. Transcripts (i) and (ii) contain the shRNA; all 3 transcripts contain the target sensor. Consequently, shRNAs will be produced and knockdown all three transcripts. Most relevantly, provirus will be reduced and thereby packaging inhibited: the more potent the shRNA, the less efficient the viral packaging. This is a huge issue, especially for large shRNA/sensor libraries since it leads to loss or underrepresentation of the most potent shRNAs already in the packaging step, prior to the assay. FIG. 5C shows reestablishment of equal retroviral packaging through suppression of components of the miRNA machinery. Phoenix packaging cells were transfected with TRMPV vectors expressing potent shRNAs (sh.Luci) and carrying cognate (target.Luci) or control target sensors (target.p53), either in the presence or absence of one of three DGCR8 siRNAs (two shown). Produced viruses were subsequently used to infect Rosa-rtTA p53−/− MEFs. Infection efficiencies were quantified on a flow cytometer. Potent shRNA-cognate sensor constructs induced Venus reporter gene knockdown in Phoenix packaging cells (upper row), resulting in reduced virus production as demonstrated by transduction rates of infected MEFs (lower row). Co-transfection of functional DGCR8 siRNAs disabled RNAi and reestablished equal and efficient retroviral packaging, independent of shRNA and presence or absence of a cognate target sensor.

Figure 6:
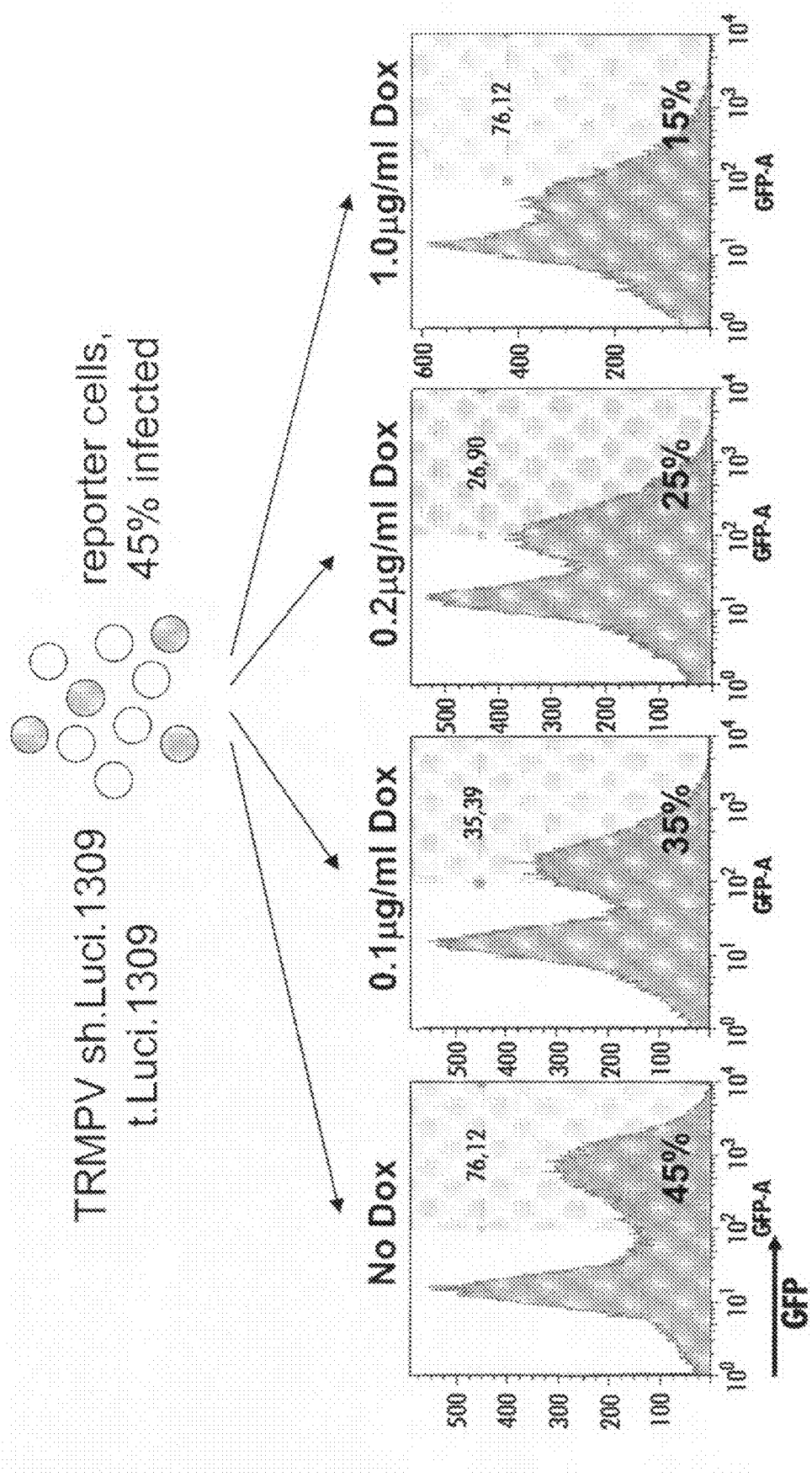

FIG. 6. Confirmation that potent RNAi molecules can specifically knockdown reporter gene expression via target sensors on the same transcript. Specificity of reporter gene knockdown was confirmed by a doxycycline titration. Rosa-rtTA MEFs partially infected (45%) with TRMPV sh.Luci.1309.t.Luci.1309 (or sh.p53.1224.t.p53.1224) were treated with six different Dox concentrations (0.00, 0.01, 0.02, 0.10, 0.20, 1.00 µg/ml). Cells were analyzed by flow cytometry for measuring reporter gene expression by green-intensity distribution.

Figure 7:
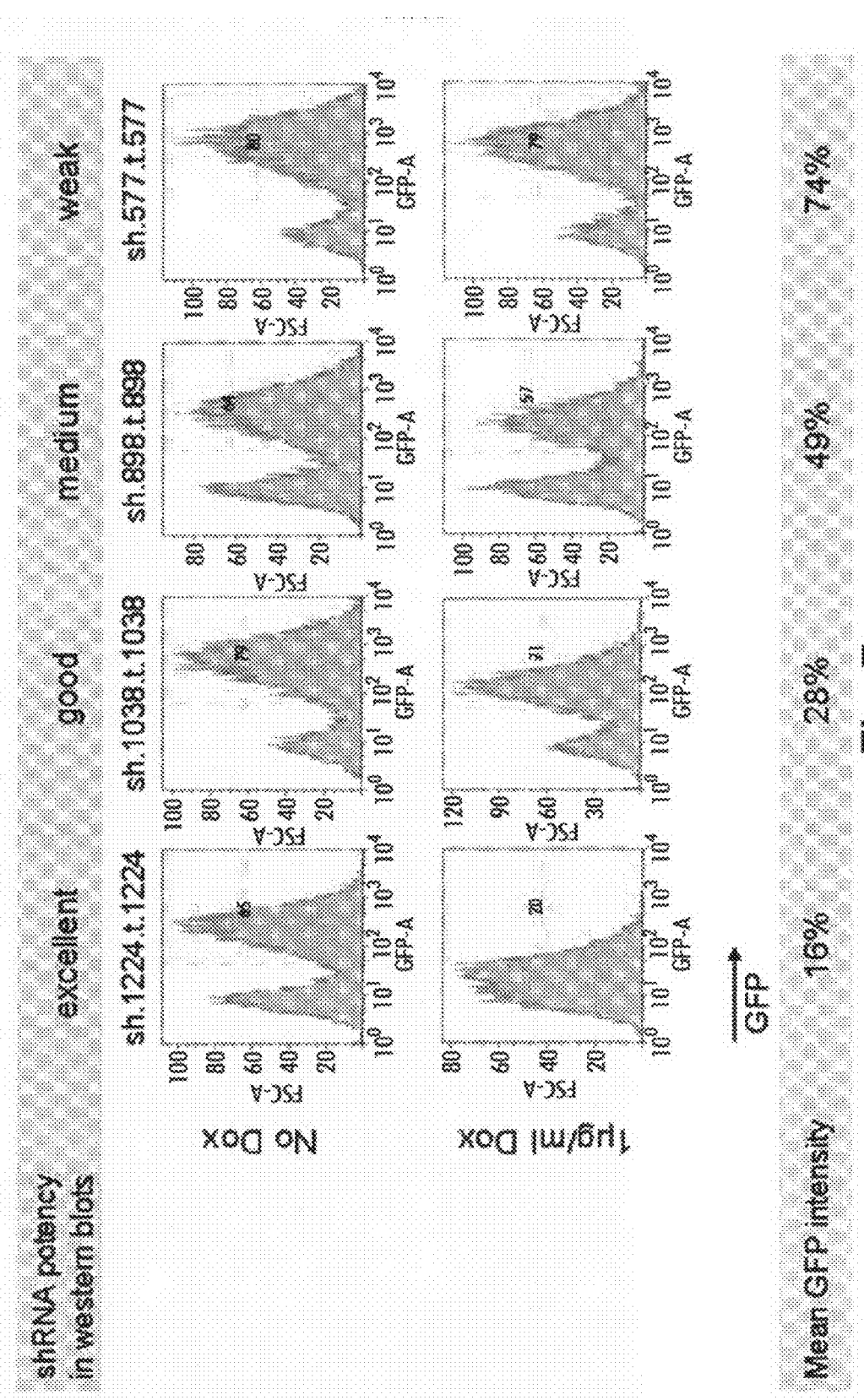

FIG. 7. Intermediate or weak RNAi molecules can also be predicted by the system. shRNA knockdown efficacy was evaluated. Rosa-rtTA p53$^{-/-}$ MEFs were infected with TRMPV vectors carrying different shRNAs with different known potencies in conjunction with their cognate target sensors. The green fluorescence intensity distribution was measured on a flow cytometer. The mean GFP intensity represents the percentage of the mean green intensity of the infected On-Dox population compared to the Off-Dox population. Western blot ranking was determined by previous blot analyses.

Figure 8A:
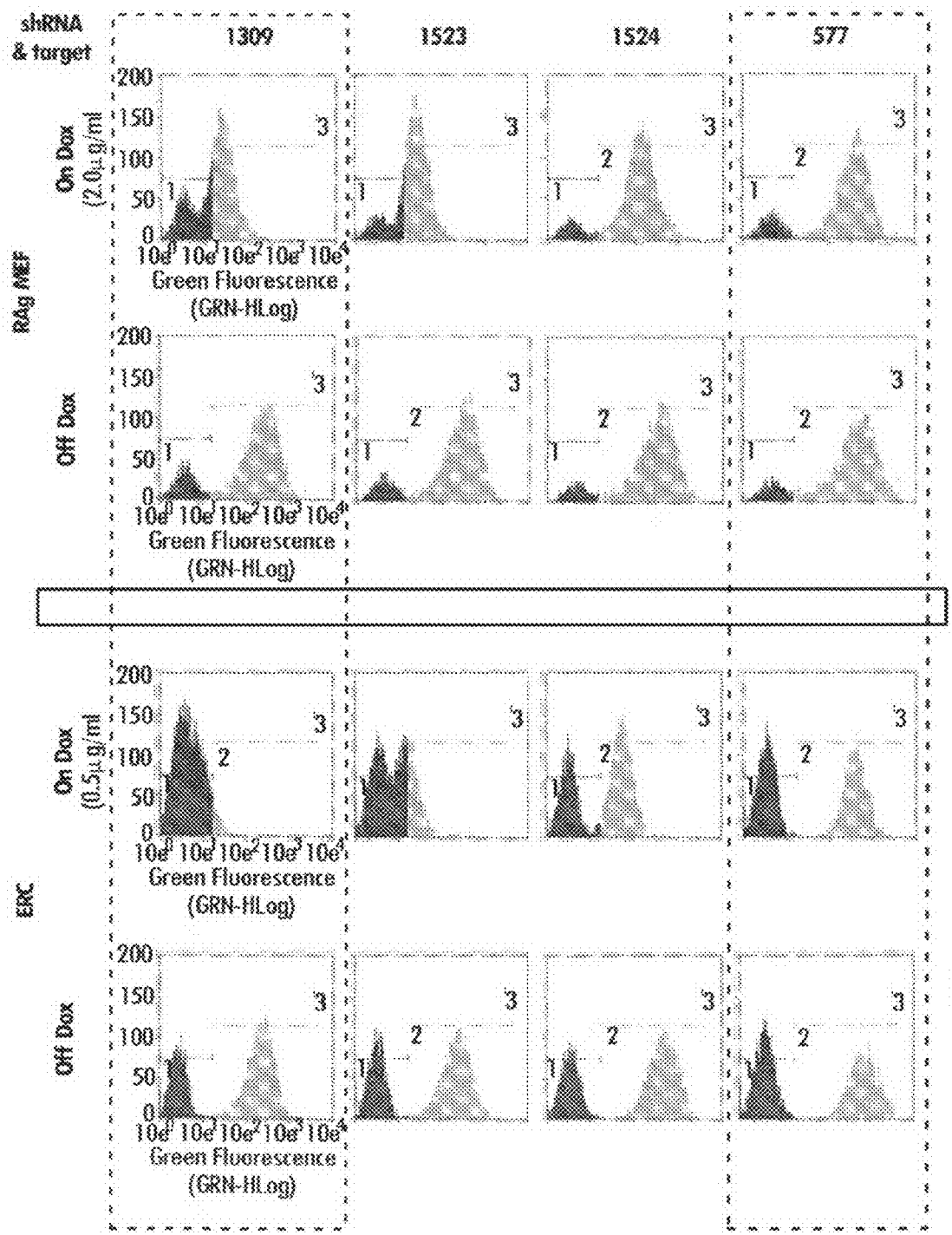
Figure 8B:
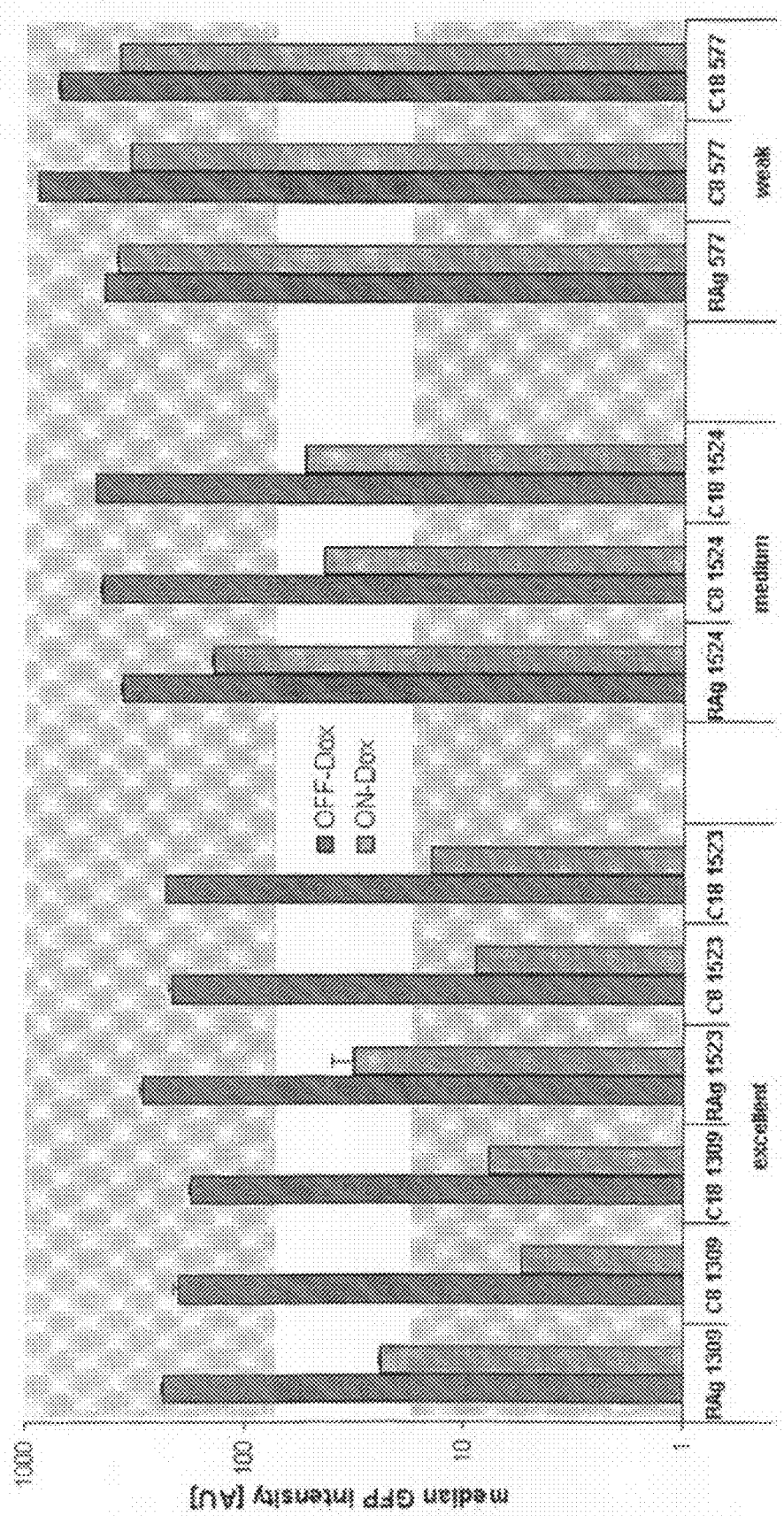

FIG. 8. The ERC cell line accurately predicts potency of well-characterized shRNAs. In FIG. 8A, RAg MEFs and ERCs (DF1ER3 C18) were infected with TtNmPV sh.Luci.1309, sh.PTEN.1523, sh.PTEN.1524, or sh.C/EBPa.577 and treated for 7 days+/−doxycycline. Green fluorescence was measured on a flow cytometer. FIG. 8B shows quantification of the experiment shown in FIG. 8A for the given Dox concentrations (500 ng/ml for ERC=DF1 ER3 C18=C18 and DF1 ER3 C8=C8; 2000 ng/ml for RAg MEF=RAg). The green-shift was quantified after 7 days+/−Dox.

Figure 9:
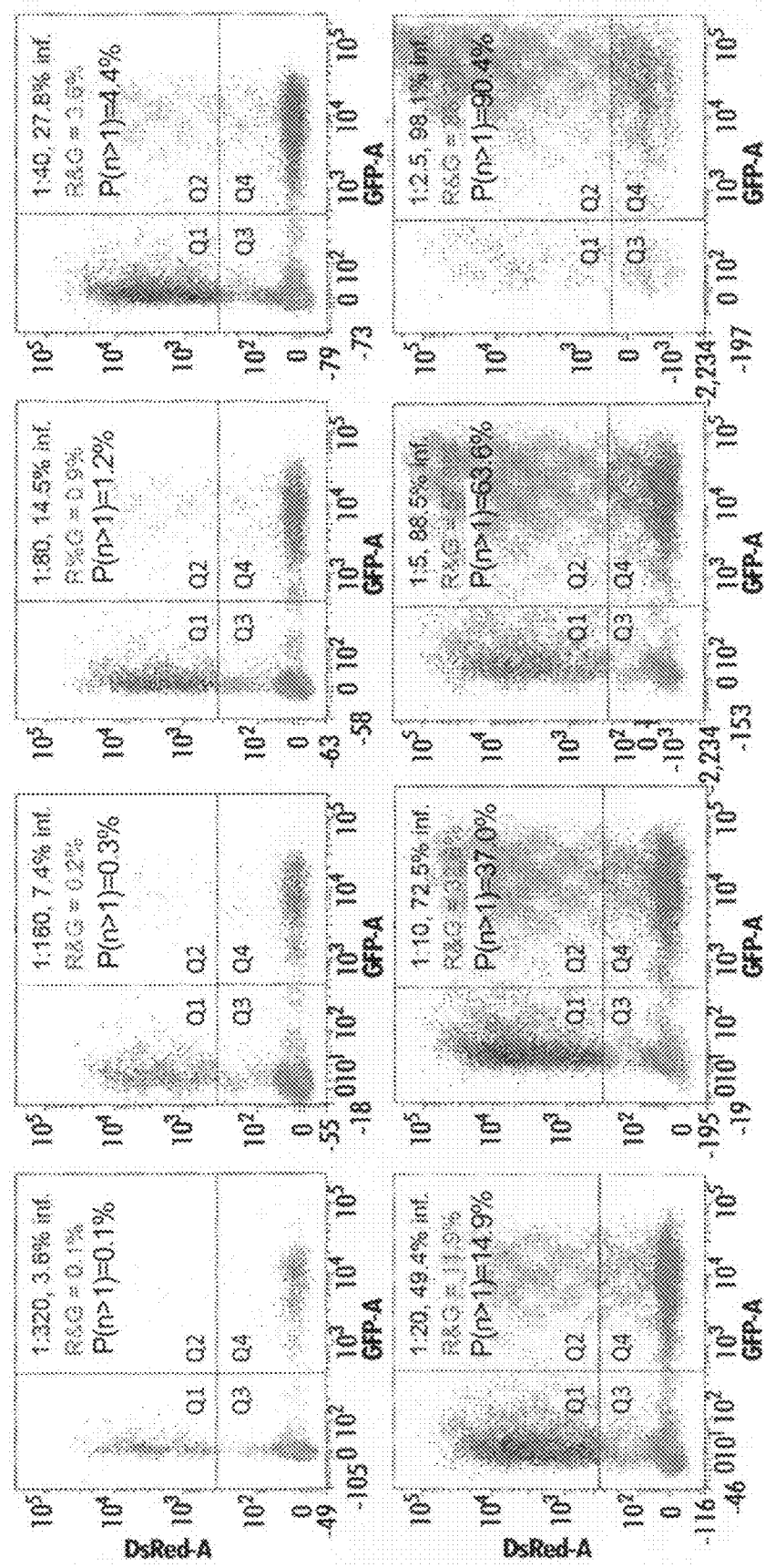

FIG. 9. ERCs show a strong correlation between infection percentage and genomic integrations. Dot plot of ERCs infected at different dilution rates (displayed as 1:X) with viral supernatants from ecotropic Phoenix (HEK 293T) co-transfected with MSCV-Red2 and MSCV-GFP. Two days after infection, the cells were analyzed on a flow cytometer and infection percentages determined. The percentage of infected cells (Q1+Q2+Q4) is shown (X % inf.) as well as the percentage of double positive cells (Q2, R&G=X). The theoretical value for multiple integrations, P(n>1), at the respective infection rate is displayed. Note that this value is always higher than the R&G value since it includes cells with multiple integrations of the same color.

Figure 10:
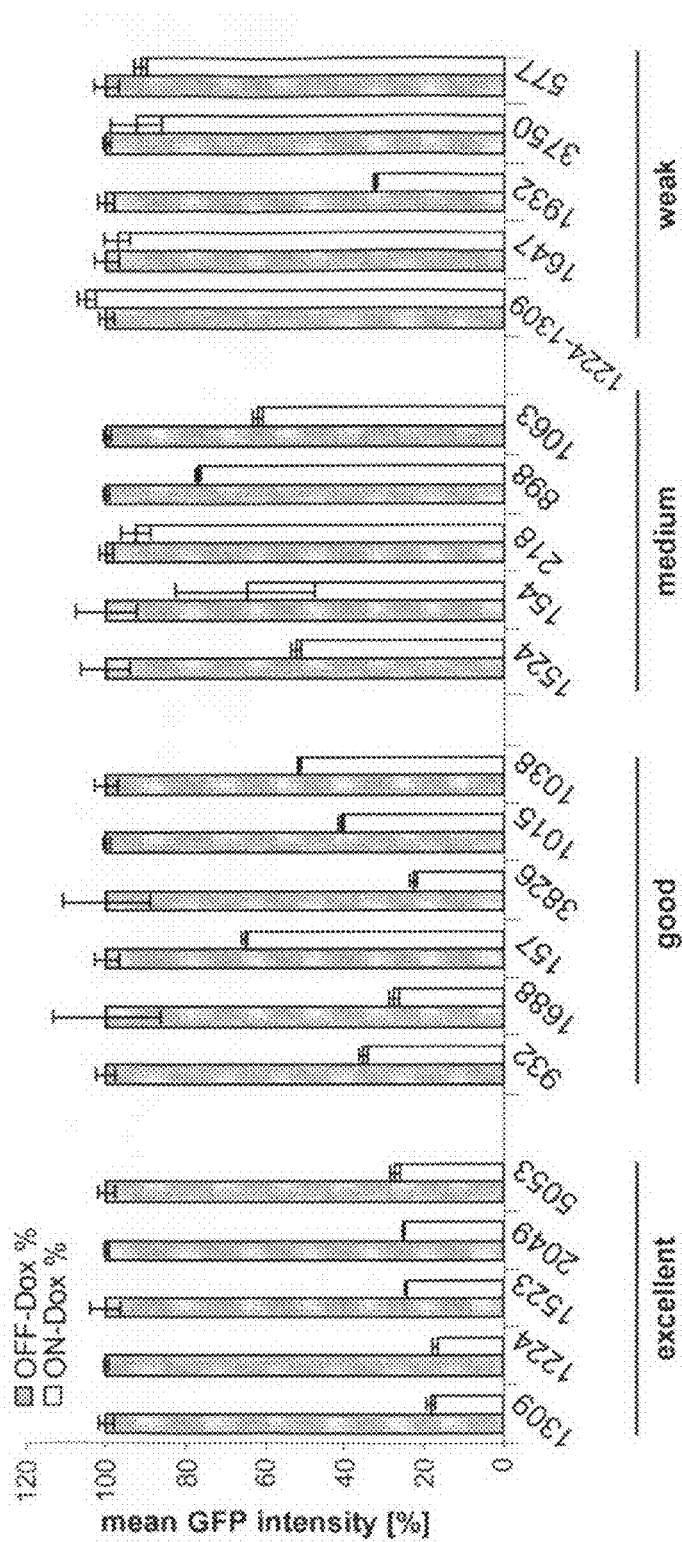

FIG. 10. Reporting shRNA knockdown efficacy. The accuracy of the reporter assay to predict shRNA knockdown efficacy was assessed by testing a set of 20 shRNA-target sensor constructs alongside one negative control. The shift in mean green fluorescence intensity was determined on a flow cytometer, and the value of the Off-Dox samples was set to 100%. Values are means of triplicates with standard deviations. All shRNAs are grouped according to Western blot analysis.

Figure 11:
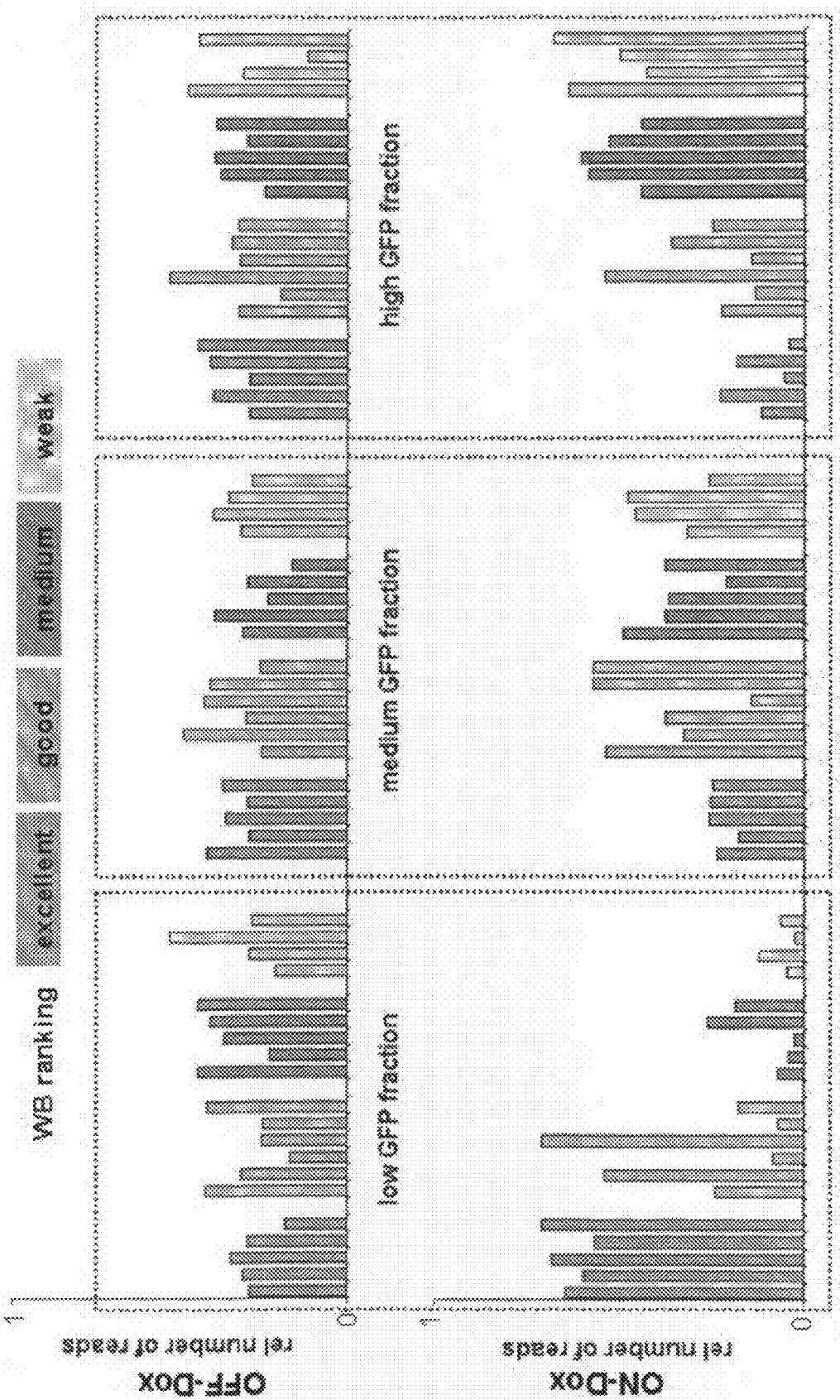

FIG. 11. Pooled evaluation of shRNA knockdown efficacy. Histograms representing the relative number of reads obtained for a given shRNA in a specific fraction. shRNAs are grouped according to Western blot ranking. The relative number of reads represents the percentage of reads that were present in that fraction for a given shRNA. Low=20% low GFP expression, medium=20% medium GFP expression, high=20% high GFP expression.

Figure 12:
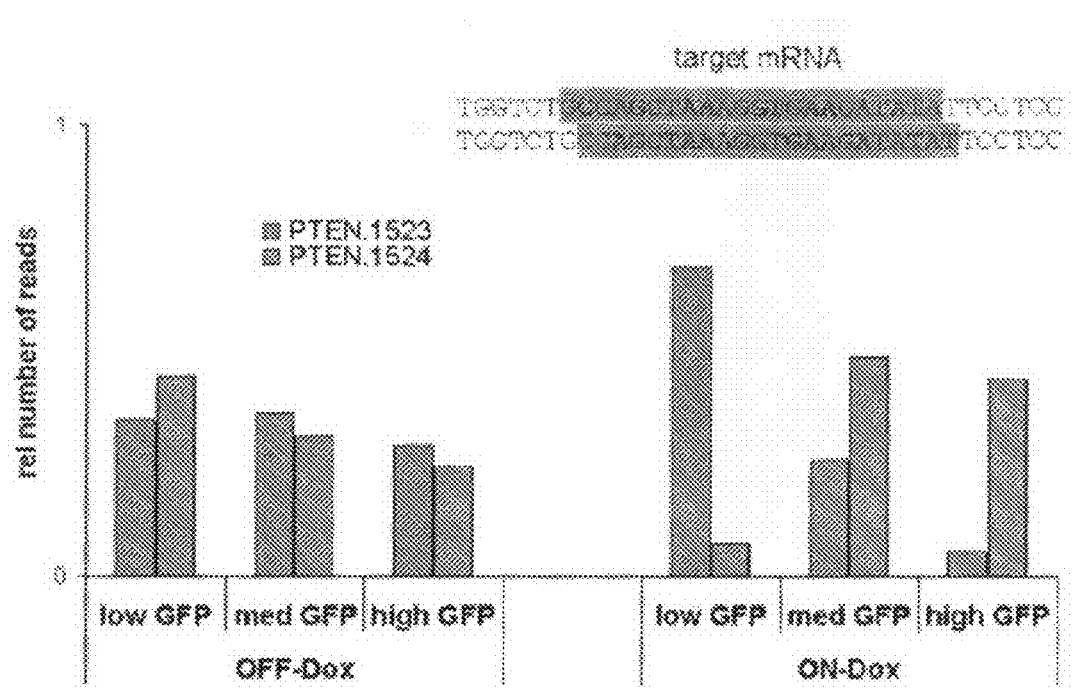

FIG. 12. The Sensor approach is capable of single nucleotide sensitivity. The sensitivity of the Sensor approach is exhibited by the PTEN shRNA efficacy testing. The figure shows a histogram of the relative number of reads (sequences) obtained for a given shRNA-target sensor construct in the named fraction. PTEN.1523 (SEQ ID NO: 3) and PTEN.1524 (SEQ ID NO: 4) are two shRNAs that are shifted by only one by on the target mRNA (SEQ ID NO: 1). The relative number of reads was calculated by dividing the number of reads for a given shRNA in a specific fraction by the sum of reads for that construct in the whole subpopulation. Low=20% low GFP expression, medium=20% medium GFP expression, high=20% high GFP expression.

Figures 13, 14:
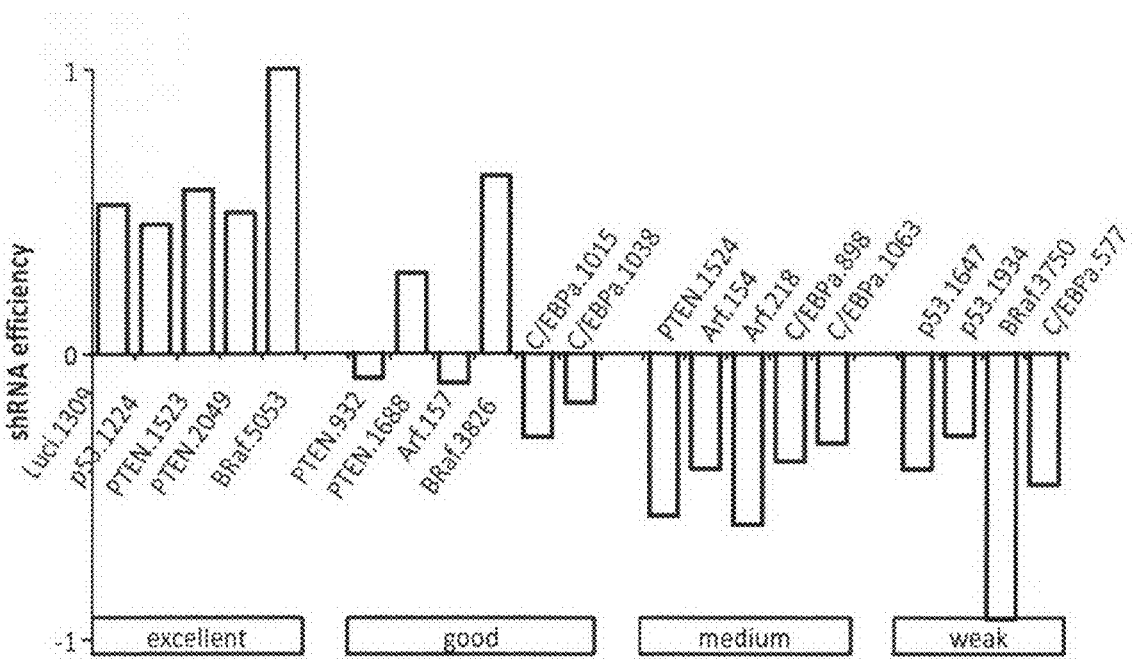

FIG. 13. Reporter assay based shRNA ranking. The figure shows a histogram for single variable readout for the evaluation of shRNA efficacy. Potent shRNAs receive a positive value (maximum 1) and inefficient shRNAs receive a negative value (minimum −1).

FIG. 14. Tiling. The figure shows a schematic of tiling or gene tiling, a process by which every siRNA or shRNA for a given target sequence (SEQ ID NO: 2) is produced. For example, when tiling a gene, every 22-nucleotide sequence (or other length sequence, i.e., from about 16 to about 29 nucleotides) fragment possible will give rise to a different si-/shRNA, and the guide strand will be completely complementary to those 22 nucleotides.

Figure 15:
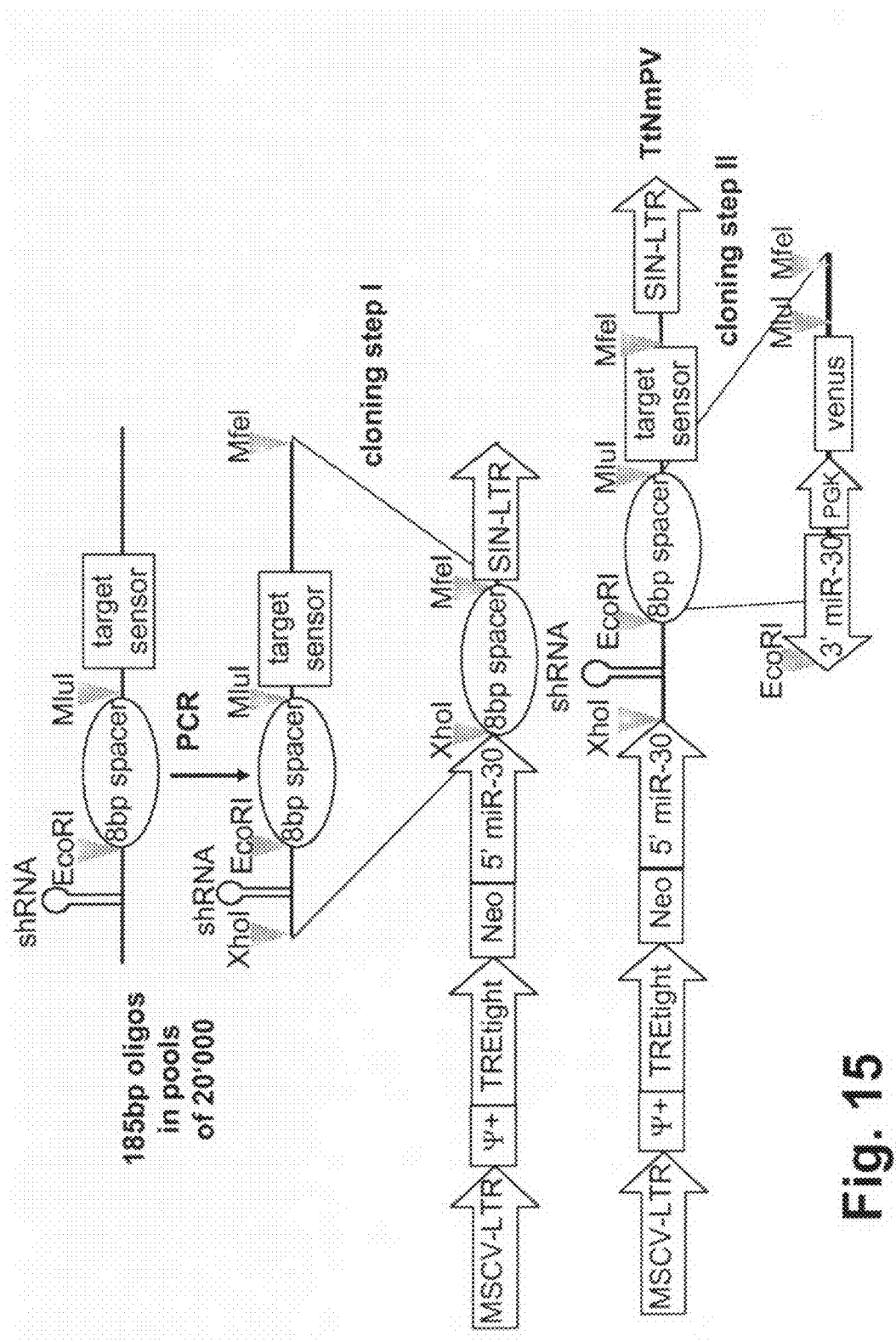

FIG. 15. Pooled cloning of shRNA-sensor constructs. The figure shows an exemplary strategy for pooled cloning of shRNAs and their cognate target sensors into an expression vector. Initially each shRNA and its cognate target sensor are synthesized by on-chip synthesis as one oligonucleotide. This guarantees the essential coupling of shRNA and its corresponding or cognate target sensor. Pools of approximately 20,000 shRNA-target sensor oligonucleotides are synthesized on each chip. These pools are subsequently amplified by polymerase chain reactions (PCR) with primers that add the missing endonuclease restriction sites. The amplified oligonucleotides are then cloned into expression vectors in which the sequence between the beginning of the shRNA and the end of the target sensor had been substituted by a small spacer, which is now replaced by the cut PCR product (cloning step I). In a second cloning step, the missing part of the expression vector is inserted between the shRNA and the target sensor, thereby completing the vector. In the example of TtNmPV, in a first step the 3' miR30-PGK-Venus coding sequence is cut out of the vector and replaced by oligonucleotides encoding the shRNA-target sensor library. In the second step this 3' miR30-PGK-Venus fragment is re-inserted into the product of cloning step I, thereby reconstituting the complete TtNmPV vector now containing an shRNA-target sensor library.

Figures 16A, 16B:
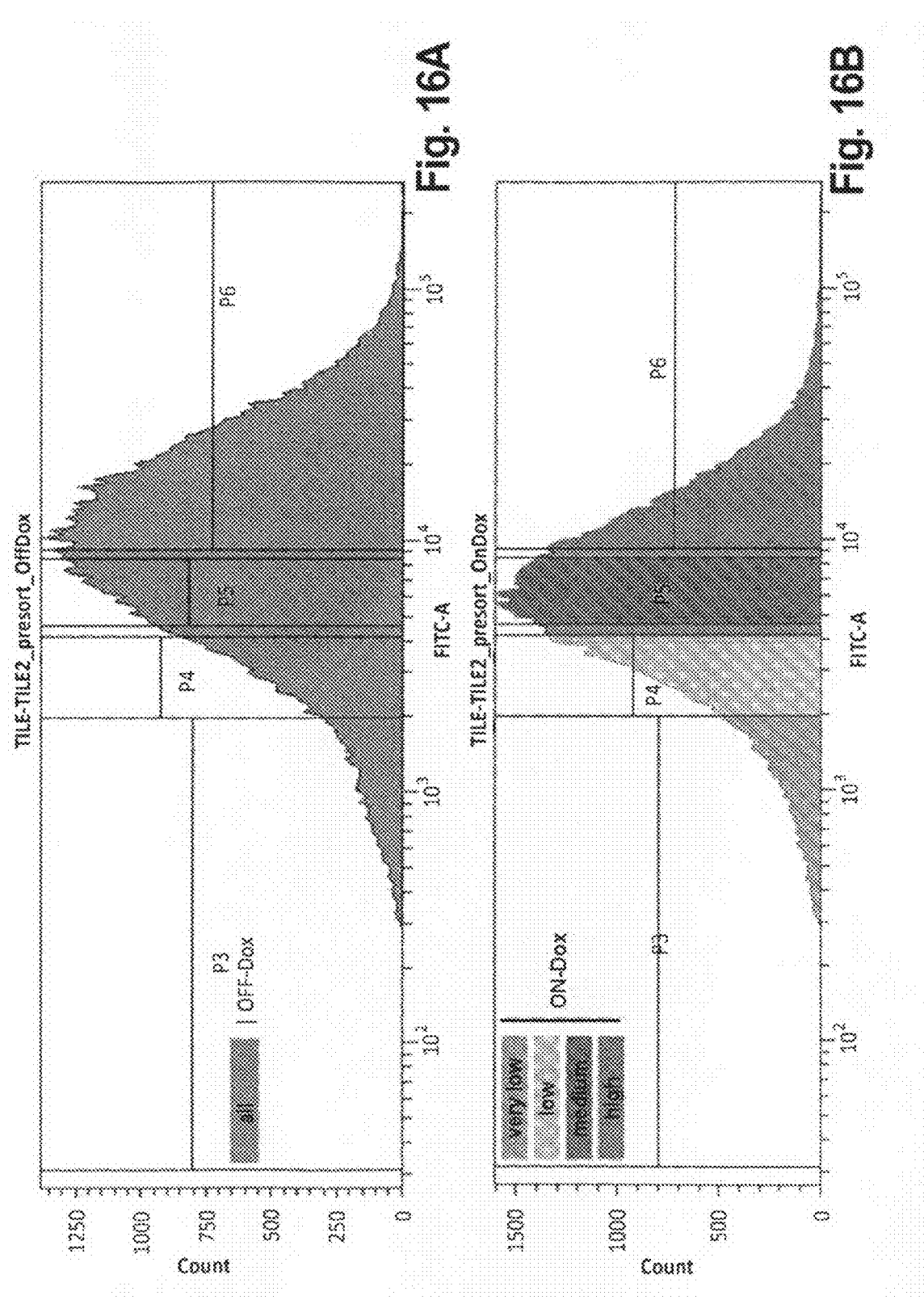

FIG. 16. Tiled-sensor 4-way sorting strategy. RAg MEFs were infected with a large tiled TtNmPV shRNA-target sensor library and either sorted or selected with neomycin for infection. FIG. 16A shows RAg MEF cells infected with a tiled TtNmPV library, which was kept for 7 days Off-Dox. The same sorting gates used for the On-Dox population (FIG. 16B) were overlaid here for clearer visualization of the green-shift. For sorting, however, gates were drawn to include the same percentages of cells in each fraction. FIG. 16B shows the infected cells after 7 days On-Dox (4 µg/mL). The sorting gates were color coded with the name of the respective sort fraction. 10% very low, 20% low, 30% medium, and 30% high GFP (Venus) expressing cells.

Figure 17:
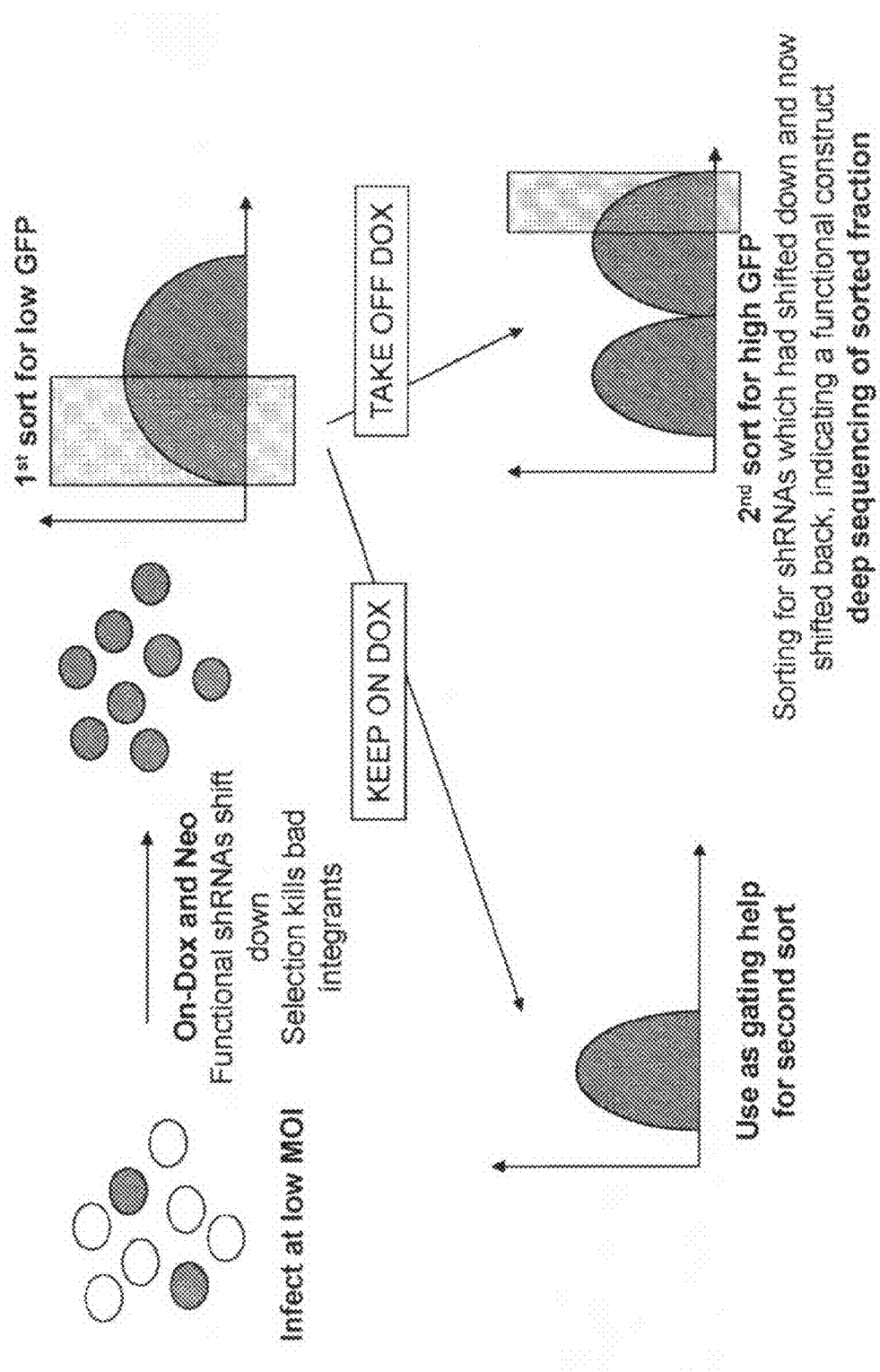

FIG. 17. Schematic of the tiled-sensor backshift sorting strategy. Target cells are infected at low multiplicity of infection (MOI) and directly treated with doxycycline. The first sort on low GFP expressing cells depletes all weak shRNAs and shRNAs that were not correctly synthesized, while enriching for potent shRNAs. The second sort (Off-Dox) depletes badly integrated shRNAs and enriches potent shRNAs.

Figure 18:
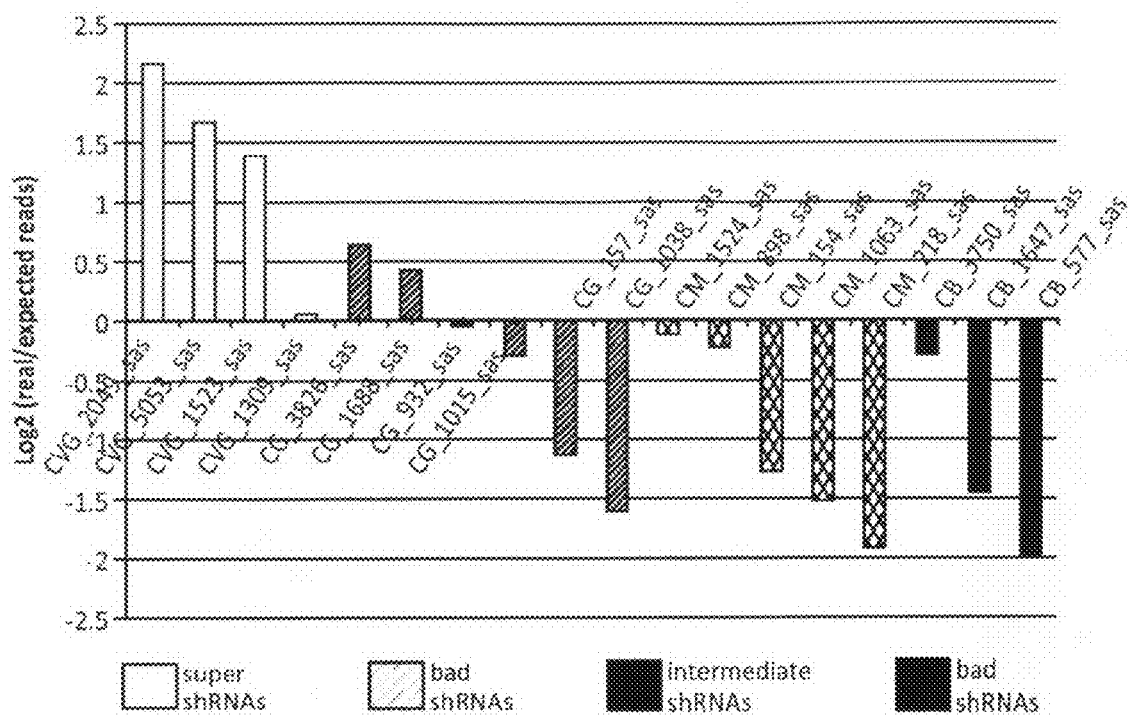

FIG. 18. TILE backshift on-chip controls. Representation of control shRNAs that were synthesized together with 20,000 other shRNAs on an oligonucleotide chip. Ranking: Log 2 (real vs. expected reads). Expected reads are calculated based on the distribution in the plasmid pools data.

Figure 19:
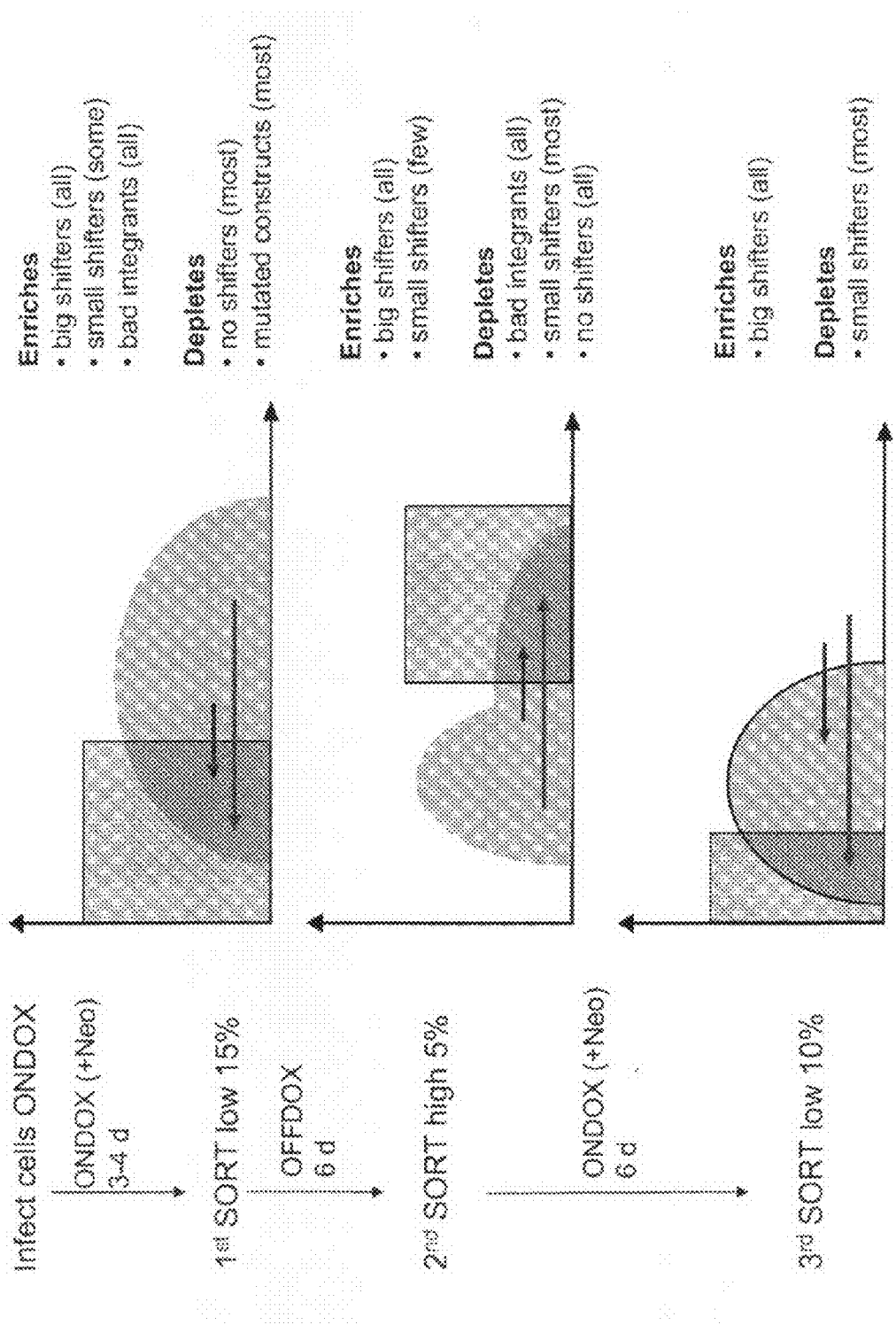

FIG. 19. Schematic of the tiled-sensor enhanced backshift strategy. Target cells are infected at low MOI and directly treated with doxycycline. The first sort on low GFP expressing cells depletes all weak shRNAs and shRNAs that were not correctly synthesized, while enriching for potent shRNAs. The second sort depletes badly integrated shRNAs and enriches potent shRNAs. The third sort further enriches for potent shRNAs that show a large GFP shift after a second round on doxycycline. This strategy is particularly useful if the expected amount of potent shRNAs is low, like it is the case with tiled libraries.

FIG. 20. Sensor Ping-Pong. FIG. 20A extends the scheme shown in FIG. 19. The flow cytometry sorting strategy is based on reference shRNA guided gating that directly assesses green-shift capabilities of shRNA-target sensor constructs. Infected cells are first sorted On-Dox for low GFP expression. Subsequently, sorted cells are kept in culture without doxycycline and then sorted for high GFP expression. In a third sort, cells are again sorted On-Dox including only the cells with the faintest GFP expression. For each step, sorting gates are drawn based on reference populations (Top5=5 excellent shRNAs; Bottom5=5 weak shRNAs). To further purify the sorted populations and select for potent shRNAs, sorting steps 2 and 3 can be iterated using the same Dox cycles and gating strategy. FIG. 20B shows that this sorting strategy accurately enriches for potent RNAi molecules. The distribution of sequencing reads is shown for the 18 control shRNAs after 3 or 5 sorts. The counted reads for each shRNA were normalized on the number of expected reads based on the distribution in the initial plasmid pool. The log 2 ratio indicates either enrichment (bars above the axis of abscissae) or depletion (bars below the axis of abscissae) of the given shRNA. The values are the average of two biological replicates with approximately 5,000,000 total sequence reads each. FIG. 20C shows general analysis of shRNA sequence data obtained from ERCs infected with the tiled sensor library and sorted with the Sensor Ping-Pong strategy. The graph shows pool complexity and distribution of read for (i) the plasmid pool, (ii) the unsorted infected cells and (iii) the cells after selected sorts. A general decrease in complexity and increase in representational variability can be observed with increasing sorts. FIG. 20D shows dot plots depicting the representation of shRNAs in the indicated pools (vector, S0, S1, S3, S5) as a function of their representation in the plasmid pool (vector). With increasing number of sorting steps, the correlation between initial and endpoint representation decreases. FIG. 20E shows dot plots depicting the correlation between shRNA representation in replicates (4 plots) and between unsorted and sorted cells (1 plot). Square Pearson correlation coefficients ($R^2$) are indicated. While the strong correlation between the biological replicates is retained throughout all 5 sorts, its decrease over iterated sorts shows that repeated cycles of induction and sorting resolve the correlation between initial and endpoint representation. FIG. 20F shows the transcript coverage (regarding shRNAs) of the cloned shRNA library for a selected gene with respect to the cloned chip (top panel), and the enrichment/depletion of particular shRNAs targeting a selected transcript after sorting of the infected cells (bottom panel). FIG. 20G shows that the prediction algorithms Biopredsi and DSIR were only able to predict, in their respective list of the ten best interfering RNAs against the selected target, one or two of the five most potent shRNAs, according to the sensor assay, of a tiled library to the p53, Bcl2, PCNA1, Hras, and mMyc genes, and were not able to predict any of the five most potent shRNAs found by the sensor assay for Mcl1, Rpa3, Kras, and hMyc. The results underscore the divergence in predicting interfering RNAs between existing prediction algorithms and the present invention. Hence, this highlights the novelty of the approach in predicting sequences that were not predicted by any other tool so far. Furthermore, as the shRNAs predicted by the present invention are potent, this underscores the need for the present invention to find the "best possible" shRNA. The deficiency of existing algorithms was shown previously (i) since only ~20% of predicted interfering RNAs are potent, and (ii) now since the present results show that there are very potent interfering RNAs (some of the best ones) that are not predicted by existing algorithms.

Figure 21:
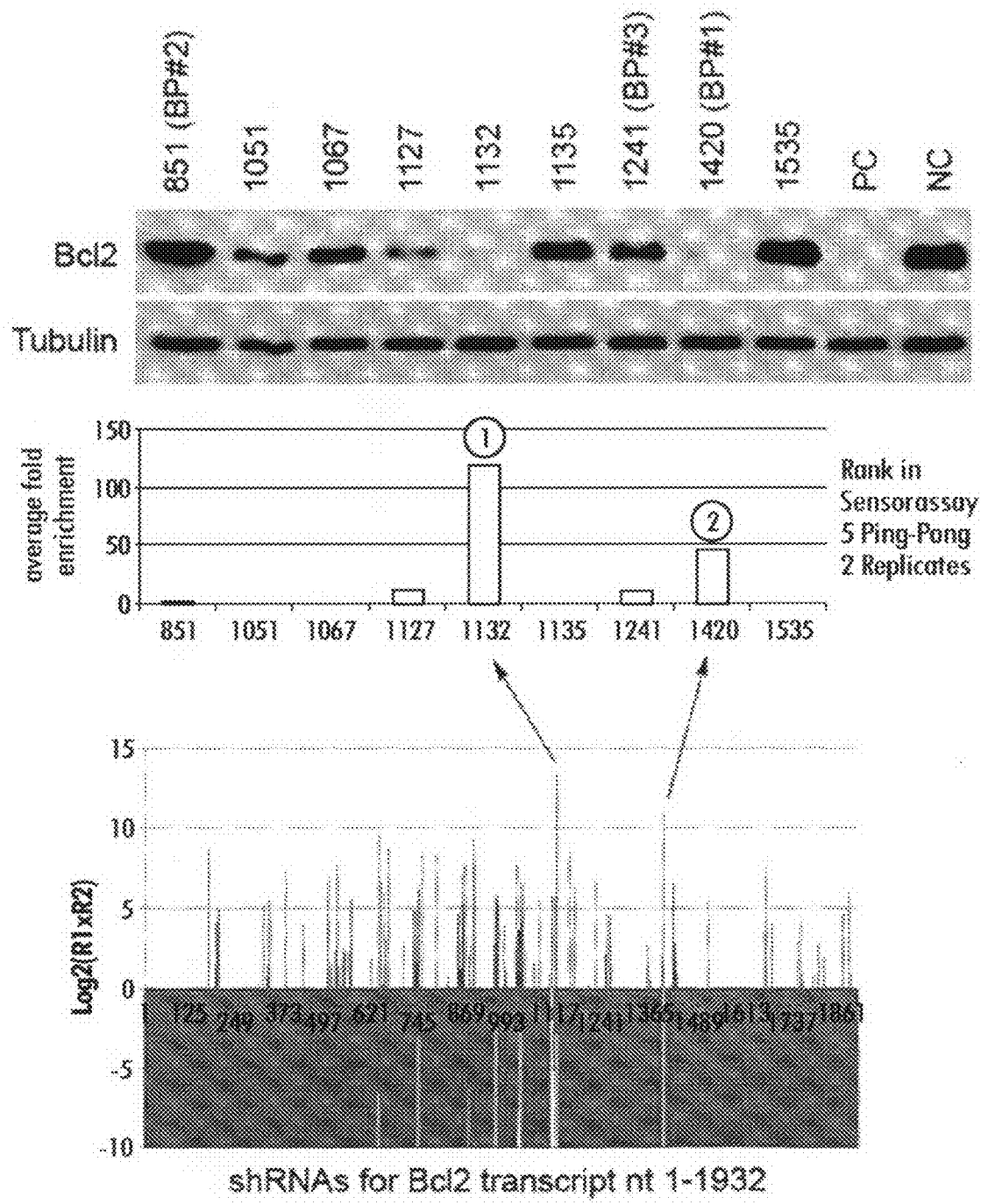

FIG. 21. Validation of optimized Bcl2 shRNAs. The common region of both murine Bcl2 isoforms (1932 nt) was tiled and all possible shRNAs were evaluated by the Sensor assay. Immunoblotting for Bcl2 of selected scoring and non-scoring shRNAs demonstrates that enrichment levels in the high-throughput reporter assay accurately predict shRNA potency and identify the best possible shRNAs targeting Bcl2. Tubulin was used as a loading control in the Western blot. BP# indicates the BIOPREDsi prediction rank. PC: positive control, very potent shRNA targeting only Bcl2 isoform 1 (outside common transcript); NC: negative control, potent control shRNA (sh.Luci.1309) targeting luciferase.

Figure 22:
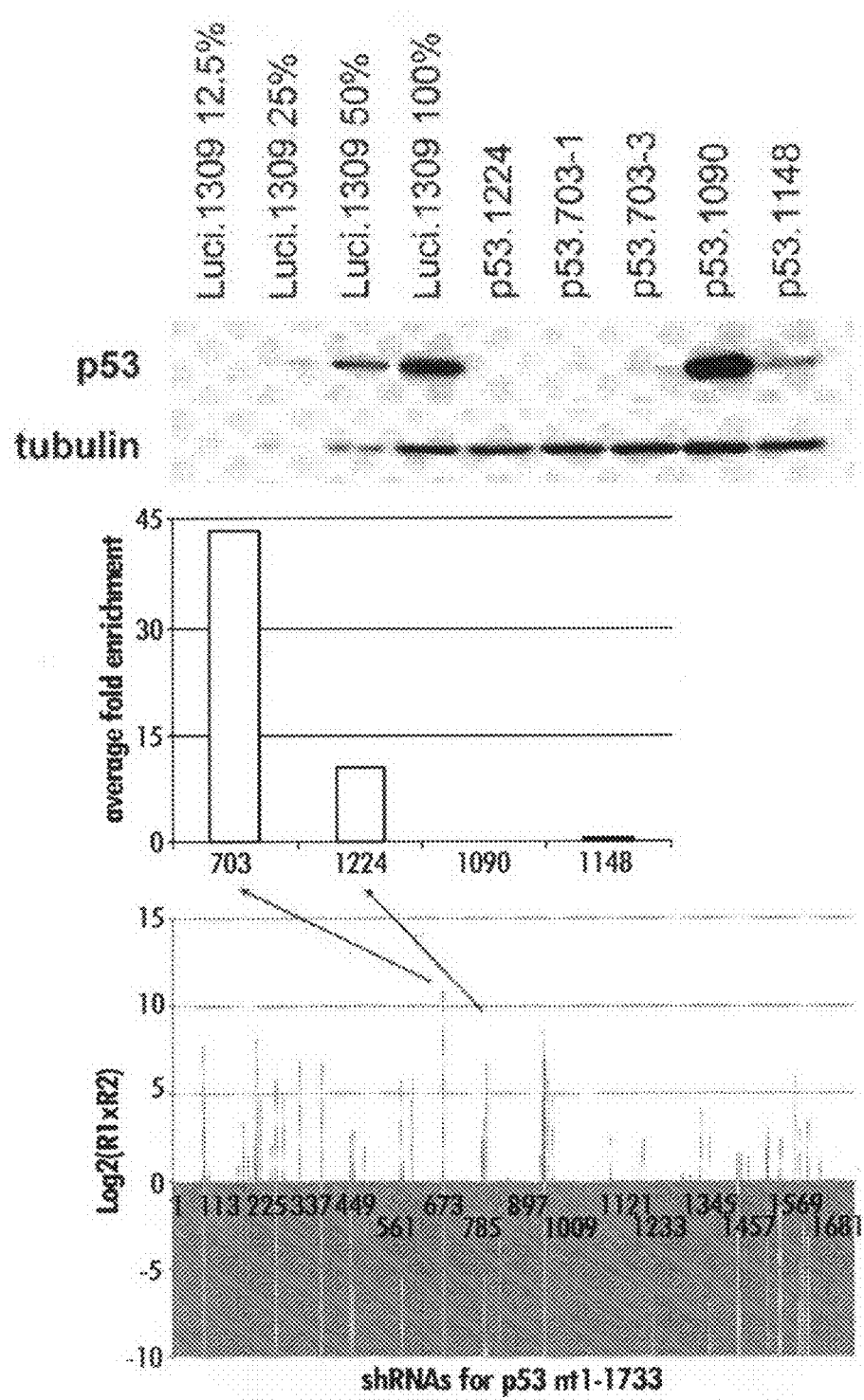

FIG. 22. Validating reported shRNA knockdown efficacy. The Trp53 transcript (1733 nt) was tiled and all possible shRNAs were evaluated by the Sensor assay. Western blotting for p53 of selected scoring and non-scoring shRNAs demonstrates that enrichment levels in the reporter assay (bar graphs, in the middle part for selected shRNAs and in the lower part for the whole transcript) accurately predict shRNA potency. Serial dilutions of the shRNA sh.Luci.1309 against luciferase were used as negative control and for quantification of knockdown.

4. DETAILED DESCRIPTION OF THE INVENTION

RNAi technology enables specific suppression of the expression of virtually any gene and provides a new tool for drug target discovery, validation, and therapy. To obtain functional RNAi reagents for biological, biomedical, and clinical applications, it is important to identify potent interfering RNA molecules (RNAi molecules) for a gene of interest. The efficiency of the suppression of specific target genes (i.e., target mRNA degradation and/or deadenylation and/or inhibition of protein translation) depends heavily on the chosen RNAi trigger. To this end, many laboratories have created algorithms for predicting si- or shRNA efficacy in silico. However, the in silico approach is limited by its failure to accurately predict the potency and dysfunction of RNAi molecule designs, which is due to the incomplete understanding of the sequence-specific rules governing si- or shRNA mediated gene silencing efficacy and the production of potent RNAi triggers.

The core of the invention is the combination, on one construct, of an RNAi molecule-encoding sequence, a sequence encoding a reporter, and a target sequence that is specific for the RNAi molecule (cognate target sequence), and the use of the construct to determine the potency of the encoded RNAi molecule. These results can be extended to several other applications, as described herein.

In particular, the present invention provides technology enabling the design of the most potent RNAi molecules targeting any given transcript. To this end, a reporter assay was established allowing high-throughput evaluation of RNAi potency. In one aspect, this approach, when combined with a sorting strategy termed "Sensor Ping-Pong," enables the identification and isolation of the most potent RNAi molecules from large pools. In another aspect, the capability of the present methods to screen tiled libraries is important because algorithm-based libraries are based on incomplete parameters for defining the potency of RNAi. To find the "best possible" RNAi targeting a specific transcript, all RNAi molecules targeting that transcript can be synthesized in an approach termed "tiling" and then be evaluated by the Sensor assay of the invention. Tiling a transcript allows for unbiased, functional evaluation of RNAi potency and, hence, identification of the most potent RNAi molecule targeting that specific transcript using the Sensor assay.

Thus, the invention provides a reporter assay system that allows for the high-throughput functional analysis of large, tiled RNAi libraries. In another aspect, the reporter assay system allows for the identification of the most potent RNAi molecules within large pools designed by existing algorithms. RNAi molecules that are determined to have sufficient potency are validated in vitro, and their biological potential can be tested in vivo, such as in various mouse models. The data generated by the screening of tiled libraries provides insights into the sequence-specific requirements of RNAi, and can be used for bioinformatic analysis and the generation of new prediction algorithms. Additionally, the data generated by the reporter assay can be used to identify RNAi targets with therapeutic potential, and can also be used to optimize design and potency of RNAi molecules, such as siRNAs, for clinical applications. In one application, the assay can inform design of modified siRNAs. Modified siRNAs include molecules containing nucleotide analogues, including those molecules having additions, deletions, and/or substitutions in the nucleobase, sugar, or backbone; and molecules that are cross-linked or otherwise chemically modified. (See Crooke, U.S. Pat. Nos. 6,107,094 and 5,898,031; Elmen et al., U.S. Publication Nos. 2008/0249039 and 2007/0191294; Manoharan et al., U.S. Publication No. 2008/0213891; MacLachlan et al., U.S. Publication No. 2007/0135372; and Rana, U.S. Publication No. 2005/0020521; all of which are hereby incorporated by reference.)

The target RNA sequence transcribed from the reporter construct comprises a target region that is part of the mRNA of a gene of interest, and is directly targeted by an RNAi molecule (complementary to the RNAi molecule). This target RNA sequence comprises about 22 nucleotides, as siRNA or shRNA molecules that are processed by the RNAi machinery eventually result in a 22 nucleotide guide sequence in the RISC complex. The fusion between the reporter sequence and the target RNA sequence is herein referred to as a "target sensor." The target sensor may optionally include additional sequences (e.g., 0 to 500 nucleotides) from the target mRNA that flank the sequence of the target region in the mRNA of the gene of interest (i.e., the gene to be knocked-down by selected RNAi molecules chosen by the present methods). In theory, flanking sequences can be as large as the remaining transcript from which the target sensor sequence is obtained. However, large flanking sequences are mostly unnecessary, and may cause complications such as retroviral packaging size limitations.

For a given library of RNAi molecules, the coding sequences for candidate RNAi molecules and their respective target sequences are cloned into the same plasmid vector. Further, if the RNAi molecule and its target are expressed from a viral-based vector, infection of an appropriate reporter cell line at low MOI can compartmentalize each RNAi molecule and its target sensor into a single cell. Hence, combined with a suitable reporter, the target sensor reporter system of the invention allows for high throughput analysis of RNAi knockdown efficiencies on, e.g., a flow cytometer.

A reporter construct of this invention is a plasmid vector which minimally comprises: (1) a sequence encoding an RNAi molecule, and (2) a target sensor that comprises a sequence encoding a reporter and a target sequence for the RNAi molecule, located preferably in the UTR of the reporter. Because the target sequence is untranslated, it does not affect the translation and composition of the reporter protein. If the RNAi molecule effectively initiates an RNA interference response against the target-sensor transcript (i.e., a knockdown), its expression is inhibited due to degradation of its target and/or inhibition of its translation, and the detectable level of the reporter protein will go down. If the RNAi molecule is ineffective in knocking down the reporter-sensor transcript, the detectable level of the reporter protein will remain unchanged despite the expression of the RNAi molecule. In other words, by measuring and comparing the knockdown levels of the reporter using different RNAi molecules, one can determine the relative potency of those RNAi molecules.

In other embodiments, the reporter construct of the invention can comprise, in 5' to 3' order, the following elements: (1) a first promoter (which can be inducible, such as a TRE promoter), (2) a selection gene (such as Neomycin) or a first reporter (such as dsRed2) whose expression is under control of the first promoter, (3) a sequence encoding an RNAi molecule, for instance, an shRNA molecule of about 16-29 nucleotides or an shRNA molecule which can be based on an miR30 shRNA design for example, whose expression is also under control of the first promoter, (4) a second promoter (such as PGK), (5) a second reporter sequence that is different than the first reporter sequence (if there is a first reporter sequence; i.e., if the first reporter is a fluorescent protein, then the second reporter is a different color fluorescent protein, such that both reporters can be simultaneously detected), whose expression is controlled by the second promoter, and (6) a target sequence that comprises at least about 8-29 nucleotides of an mRNA sequence, which sequence is complementary to at least a portion of the RNAi molecule in this same reporter construct, and which sequence is located on the same transcript of the second reporter. In a preferred embodiment, the sequence encoding the RNAi molecule comprises about 19-29 nucleotides. In another preferred embodiment, the target sequence comprises about a 19 to about a 22 nucleotide sequence. In one embodiment, the target sensor sequence is about 19 to about 22 nucleotides.

In other embodiments, elements of the reporter construct can be part of a viral vector backbone, such as a retroviral backbone. In this embodiment, the elements are between a viral 5' LTR and 3' LTR, and a packaging sequence is located 5' to the first promoter and 3' of the 5' LTR. This viral construct can then be packaged into virions when transfected into a packaging cell line. These virions, which are replication defective, can then be infected into cell lines for knockdown screening.

This invention provides reporter assays that allow rapid, high throughput identification of RNAi molecules with high potency. In these assays, an RNAi molecule transcribed from a reporter construct suppresses the expression of a reporter on the same construct that harbors the cognate target sequence (target sensor) of the RNAi molecule. The target sequence can be in any region of the construct, provided that is does not affect the function of the reporter protein. For example, the target sensor can be in an untranslated region of the reporter, such as the 3' UTR or the 5' UTR. The 3' region is preferable because insertion of the target sensor here is less likely to affect transcription in a non-RNAi manner. The extent of reporter knockdown, as measured by, e.g., the level of the reporter protein, correlates with the potency of the RNAi molecule and can serves as a gauge for RNAi appraisal.

Single-copy genomic integrations are a prerequisite for large-scale screening applications, since they guarantee a direct coupling of the observed phenotype (i.e., measured fluorescence intensity) and the underlying genotype (i.e., shRNA potency). When infecting cells with viruses, the number of genomic integrations can be controlled in a stochastic process via the multiplicity of infection (MOI). A low MOI is required to achieve single copy genomic integration. Example 3 describes the generation of a novel reporter cell line, ERC, and the conditions that yield single copy integration.

The MOI is defined as the ratio of infectious agents to infection targets, i.e., when referring to a group of cells inoculated with infectious virus particles, the MOI is the ratio defined by the number of infectious virus particles deposited in a well divided by the number of target cells present in that well. The actual number of infectious agents entering an infection target is a statistical process wherein the probability that n infectious agents will integrate into any infection target when inoculated at an MOI of m can be calculated for a given population using a Poisson distribution: $P(n)=m^n*e^{(-m)}/n!$. This mathematical model assumes that the infectability of each cell is equal throughout the whole population. Hence, in order to apply this model to a cell line for the prediction of genomic integration numbers, equal efficiency of retroviral infection has to be given throughout the population, i.e., all cells should statistically behave equally, as opposed to cell populations where fractions of the cells are differentiating and others are not.

4.1 RNAi Background

To date, distinct forms of RNA silencing have been found to regulate gene expression, to mediate antiviral responses, to organize chromosomal domains, and to restrain the spread of selfish genetic elements. For example, miRNAs derived from dsRNA precursors regulate gene expression in somatic cells by reducing translation and stability of protein-coding mRNAs.

The primary step in miRNA biogenesis is the nuclear cleavage of the "primary micro RNA" (pri-miRNA), liberating an approximately 70 nucleotide (nt) stem-loop intermediate known as "micro RNA precursor" (pre-miRNA). This processing step is performed by the RNase III endonuclease Drosha in conjunction with the dsRNA-binding protein "DiGeorge syndrome Critical Region gene 8" (DGCR8) in humans (Pasha in *drosophila*), leading to 5' monophosphates and ~2 nt 3' overhangs characteristic for RNase III endonucleases.

The pre-miRNAs are then actively transported to the cytoplasm by Exportin-5 and the Ran-GTP cofactor. Subsequently, the mature miRNAs are excised by another RNase III endonuclease, Dicer, acting together with the dsRNA-binding protein tar-binding protein (TRBP) in humans or Loquacious (Logs) in flies. Depending on the species, the resulting short dsRNAs are about 21 to 28 nts in length.

For mRNA degradation, translational repression, or deadenylation, mature miRNAs or siRNAs are loaded into the RNA Induced Silencing Complex (RISC) by the RISC-loading complex (RLC). Subsequently, the guide strand leads the RISC to cognate target mRNAs in a sequence-specific manner and the Slicer component of RISC hydrolyses the phosphodiester bound coupling the target mRNA nucleotides paired to nucleotide 10 and 11 of the RNA guide strand. Slicer forms together with distinct classes of small RNAs the RNAi effector complex, which is the core of RISC. Therefore, the "guide strand" is that portion of the double-stranded RNA that associates with RISC, as opposed to the "passenger strand," which is not associated with RISC. The target sequence contained in a reporter construct of the present invention is at least partially complementary to at least a portion of the guide strand.

RNAi is a powerful tool for in vitro and in vivo studies of gene function and for therapy in both human and veterinary contexts. Depending on the application, any type of RNAi, including but not limited to siRNAs or shRNAs, can be used as RNAi triggers. The siRNAs have the advantage of being directly transfectable, chemically synthesized oligonucleotides that circumvent the need for cloning. siRNAs enter the miRNA processing pathway at a later stage (see FIG. 1), and bypass Drosha processing, Exportin-5 export, and, depending on their size, Dicer cleavage. However, when the objective is therapeutic, it is often preferable to use miRNA-based shRNAs as they tend to yield more effective silencing (Chang et al., *Nature Methods*, (2006), 3(9): 707-714, the contents of which are hereby incorporated by reference).

Short hairpin RNAs can be designed to mimic endogenous miRNAs. For example, it was shown that the pri-miRNA of the human miR-30 can be redesigned to allow expression of artificial shRNAs by substituting the stem sequences of the pri-miR-30 with unrelated base-paired sequences (Zeng et al., (2002), *Mol. Cell*, 9: 1327-1333, the contents of which are hereby incorporated by reference). It was determined that miRNAs are more efficiently expressed from Pol II promoters as compared to Pol III promoters (Dickins et al., *Nature Genetics*, (2005), 37: 1289-1295, the contents of which are hereby incorporated by reference).

shRNAs can be expressed from viral vectors to provide sustained silencing and high yield delivery into almost any cell type. Exemplary viral vectors include retroviral, including lentiviral, adenoviral, baculoviral and avian viral vectors. The use of viral vector-based RNAi delivery not only allows for stable single-copy genomic integrations but also avoids the non-sequence specific response via cell-surface toll-like receptor 3 (TLR3), which has raised many concerns for the specificity of siRNA mediated effects.

The choice of the right primary sequence encoding an RNAi has a pivotal role in determining the efficacy and specificity of the resulting RNAi response. To obtain potent RNAi reagents that lead to good loss-of-function phenotypes (i.e., good knockdown efficacy), it is important to choose the right RNAi sequence out of the hundreds to thousands of possible sequences for any particular target transcript. Sometimes differences as subtle as a single base pair shift on the target mRNA can turn a potent RNAi into a weak one.

Current features of design rules for RNAi molecules include the thermodynamic asymmetry of the RNA duplex, sequence homology of the seed sequence to its cognate target mRNA but not to other mRNAs, and a set of empirical single nucleotide position preferences. The thermodynamic asymmetry is important since only the strand with the less stable 5' end is favorable or exclusively loaded into the RISC and will therefore serve as the guide strand. The seed sequence comprises nucleotide positions 2-8 of the guide strand and has been show to be the major specificity determinant of si- and shRNAs. Single nucleotide positional preferences include, for example, the A or U at position 10 of the guide strand that may promote catalytic RISC-mediated passenger strand and substrate cleavage.

These and other understandings of the RNAi machinery have been integrated into algorithms for in silico prediction of effective and specific RNAi molecules. However, predicted RNAi molecules often do not pass the potency thresholds required for clear knockdown phenotypes. In fact, the present disclosure has determined that only ~20% of the forecast shRNAs confer efficient target knockdown. Reflecting the problems of in silico prediction, the design algorithm BIO-PREDsi was designed that is based on an empirically trained neural network. Birmingham et al. ((2007), *Nature Protocols* 2: 2068-2078) provide a comprehensive overview of prediction algorithms. While many such algorithms are known in the art, they are inferior to the methods of the present invention. None of the known methods can guarantee the prediction of potent RNAi triggers or can identify the most potent RNAi trigger. In fact, all of the known methods often fail to identify such RNAi sequences.

In light of RNAi drug target discovery and validation, positive- and negative-selection screens have been developed. Positive selection screens rely on the ability of an interfering RNA to confer a selective advantage (e.g., to promote proliferation and/or transformation, or to rescue a cell from a cytotoxic or cytostatic influence) and are ideal for identifying tumor suppressor genes and essential or sensitizing genes for deleterious effects of a specific drug. In contrast, negative selection screens uncover interfering RNAs that confer negative effects alone, in combination with a certain genetic lesions, or in combination with specific drugs. (The latter to are also referred to as synthetic lethality screens). Such RNAs can identify genes or pathways involved in oncogenic transformation and/or tumor maintenance. The potency of applied RNAi triggers can be validated prior to their experimental use in less complex experimental settings. However, large-scale screening approaches are not informative for the entirety of the screened RNAi targets if the employed library is not functionally validated. Neutral behavior of RNAi molecules in a non-validated RNAi library can be due to insufficient target knockdown or to a lack of biological effect of an efficient target knockdown, and hence, is not informative.

Thus, evaluation of individual RNAi molecules is necessary to validate target knockdowns. Accordingly, the invention provides high-throughput experimental approaches to functionally identify effective RNAi molecules that can complement, screen, or validate rule-driven predictions. The present methods are capable of screening tiled libraries of targets (i.e., every possible RNAi sequence for a given mRNA transcript target) in a functional high-throughput manner.

4.2 Reporter Constructs in the Sensor Approach

In order to produce optimized RNAi triggers or validate libraries, biological assays to functionally evaluate RNAi molecules are needed to rank the efficacy of sequences in order to identify those that are most potent and those that are dysfunctional. In preferred embodiments, the methods herein recapitulate the natural processes involved in RNAi-mediated target protein knockdown to give a clear readout of sRNAi efficacy through an inherent coupling of phenotype and genotype.

Current experimental methods for evaluation of target knockdown include Western blots, quantitative reverse-transcription polymerase chain reactions (Q-RT-PCRs), mass spectroscopy, and co-transfection reporter assays. Western blots suffer from the limitation that antibodies are not always available for a given target, are laborious, and sometimes inaccurate. Q-RT-PCR suffers from imprecise quantitative readouts and only reports the potency of target mRNA degradation, but fails to measure the potency of translational inhibition. Moreover, neither method lends itself to high-throughput approaches. Mass spectroscopy allows for high-throughput methods, but quantification is difficult especially for non-abundant proteins.

Reporter assays can report RNAi activity on both transcriptional and translational levels and allow for high-throughput approaches, but current assays use plasmids carrying target sequence-reporter fusions that are co-introduced into cells together with the target-specific RNAi. The majority of assays are aimed at testing the effect of different RNAi sequences on a single reporter carrying a long target mRNA sequence. One assay did design different reporter targets for different trigger sequence candidates, however this system was also based on co-transfection of the reporter plasmid and the plasmid expressing the siRNA. These prior reporter assays lack the ability to rapidly screen every possible trigger sequence to a target mRNA because they do not couple both the trigger sequence to its specific target sequence (i.e., the specific region the trigger sequence is complementary to within the entire mRNA sequence) on a single vector. This single vector not only expresses the trigger sequence, but also contains a reporter that comprises in its 3' region the specific target sequence. When this vector is based on a viral vector backbone, such as a retroviral vector, the vector can be integrated into the genome of a cell and selected for, enabling single-cell or single-cell colony screening where each individual cell/colony contains a different trigger/target sequence couple or pair. The disclosure below describes how an entire tiled library can be constructed in a single reaction.

4.2.1 Concept of a Reporter Assay for High-Throughput Evaluation of siRNA/shRNA Knockdown Efficacy For the biological or functional assays described herein, the target sensor comprises at least the direct or specific target sequence, and optionally, a stretch of adjacent flanking sequences. This target sequence is cloned into any region of a reporter sequence that does not eliminate reporter function. A functional RNAi molecule specific for the target sequence will result in suppression of reporter expression. The level of this suppressive effect directly correlates with the potency of the corresponding RNAi. In contrast to prior methods, the present methods clone each shRNA and its cognate target sensor into a single plasmid. Besides single shRNA assays, this also allows for pooled strategies (massive parallel screening of thousands of different sequences) since each shRNA is inherently linked to its cognate target sensor.

Furthermore, in embodiments where the shRNA and its target sequence are cloned into a viral vector, infection of a reporter cell line at low MOI compartmentalizes each RNAi and its target sensor into a single cell. Thus, expression of the RNAi impacts the level of reporter expression in each individual cell, which directly reports the potency of the embedded specific RNAi molecule. Within a complex cell population, reporter cells with similar levels of reporter expression contain RNAi molecules of similar potency (i.e., low reporter expression indicates strong RNAi, high reporter expression indicates weak or missing RNAi). Cell populations with similar reporter expression can be isolated through various methods, depending on the reporter (e.g., flow cytometry based cell sorting for fluorescent proteins or surface markers). Following the purification of cells with a certain level of reporter expression (e.g., low reporter expression to identify potent RNAi triggers), the RNAi molecules contained in this population are validated for a certain knockdown potency. These RNAi molecules can subsequently be identified based on their specific sequences and/or on the target sequence, using deep sequencing or hybridization to customized arrays.

4.2.2 RNAi Molecules

As used herein, interfering RNA or small inhibitory RNA (RNAi) molecules include short interfering RNAs (siRNAs), repeat-associated siRNAs (rasiRNAs), and micro-RNAs (miRNAs) in all stages of processing, including shRNAs, pri-miRNAs, and pre-miRNAs. These molecules have different origins: siRNAs are processed from double-stranded precursors (dsRNAs) with two distinct strands of base-paired RNA; siRNAs that are derived from repetitive sequences in the genome are called rasiRNAs; miRNAs are derived from a single transcript that forms base-paired hairpins. Base pairing of siRNAs and miRNAs may be perfect (i.e., completely complementary) or imperfect.

RNAi molecules useful in this invention may be, without limitation, shRNA, siRNA, piwi-interacting RNA (piRNA), micro RNA (miRNA), double-stranded RNA (dsRNA), anti-sense RNA, or any other RNA species that can be cleaved inside a cell to form interfering RNAs.

As used herein, an "shRNA molecule" includes a conventional stem-loop-stem shRNA, which forms a precursor miRNA (pre-miRNA). "shRNA" also includes micro-RNA embedded shRNAs (miRNA-based shRNAs), wherein the guide strand and the passenger strand of the miRNA duplex are incorporated into an existing (or natural) miRNA or into a modified or synthetic (designed) miRNA. When transcribed, an shRNA forms a primary miRNA (pri-miRNA) or a structure very similar to a natural pri-miRNA. The pri-miRNA is subsequently processed by Drosha and its cofactors into pre-miRNA. Therefore, the term "shRNA" includes pri-miRNA (shRNA-mir) molecules and pre-miRNA molecules. In one embodiment, shRNA molecules are designed on the human miR-30 sequence, where the natural stem sequences of the miR-30 is replaced with a stem sequence from about 16 to about 29 nucleotides in length, preferably from about 19 to 29 nucleotides in length, which substitute sequence is a sequence to be tested for its RNAi potency. The loop sequence can be altered such that the length is from about 3 to about 23 nucleotides. In a preferred embodiment, the shRNA molecule is about 22 nucleotides in length. In another preferred embodiment, the target sensor sequence is about 22 nucleotides in length.

As stated, shRNA sequences can be can be designed in the context of miR-30 miRNA (Siolas at al. (2005) *Nature Biotech.* 23: 227-231; Silva et al. (2005), *Nature Genetics* 37: 1281-1288); Zeng et al. (2002), *Molecular Cell* 9: 1327-1333; which are hereby incorporated by reference). The miR-30 natural configuration has been proven beneficial in producing mature synthetic miRNAs. Expression of endogenous miRNAs is controlled by RNA polymerase II (Pol II) promoters. It has been shown that shRNAs are also most efficiently driven by Pol II promoters, as compared to RNA polymerase III promoters (Dickins et al. (2005), *Nature Genetics* 39: 914-921). Furthermore, these previously described shRNA vectors allow the use of tetracycline-responsive promoters, one of the most effective conditional gene expression systems in in vitro and in vivo studies.

In the reporter construct of this invention, the coding sequence for the RNAi molecule is typically controlled by an inducible promoter or a conditional expression system, including, without limitation, RNA polymerase type II promoters. Examples of promoters useful in the constructs of the invention are tetracycline-inducible promoters (including TRE-tight), IPTG-inducible promoters, tetracycline transactivator systems, and reverse tetracycline transactivator (rtTA) systems. Constitutive promoters can also be used, as can cell- or tissue-specific promoters. Many promoters will be ubiquitous, such that they are expressed in all cell and tissue types.

4.2.3 Reporters

Reporters useful in this invention—sequences whose products are easily measurable—are well known in the art. They include, without limitation, acetohydroxyacid synthase (AHAS), alkaline phosphatase (AP), beta galactosidase (LacZ), beta glucoronidase (GUS), chloramphenicol acetyltransferase (CAT), various fluorescent proteins (e.g., green fluorescent protein (GFP) and its variants; red fluorescent protein and its variants, yellow fluorescent protein and its variants, such as VENUS, etc.), luminescent proteins (e.g., horseradish peroxidase (HRP) and luciferase), nopaline synthase (NOS), octopine synthase (OCS), and derivatives thereof. Reporters may also be those that confer resistance to a drug, such as neomycin, ampicillin, bleomycin, chloramphenicol, gentamycin, hygromycin, kanamycin, lincomycin, methotrexate, phosphinothricin, puromycin, doxycycline, and tetracyclin. Reporters can also be lethal genes, such as herpes simplex virus-thymidine kinase (HSV-TK) sequences, as well as sequences encoding various toxins including the diphtheria toxin, the tetanus toxin, the cholera toxin and the pertussis toxin. A further negative selection marker is the hypoxanthine-guanine phosphoribosyl transferase (HPRT) gene for negative selection in 6-thioguanine. In addition, reporters can encode cell surface antigens. Any protein expressed on the cell surface is suitable, with CD4 and CD8 being particularly preferred.

In one embodiment, the reporter constructs of the invention comprise two different reporters. The first reporter optionally reports RNAi expression and serves as a spacer between promoter and shRNA, which can increase RNAi potency for some promoters and RNAi expression systems. A second reporter can serve as an indicator of successful infection when the reporter construct is packaged into a virion by a producer or packaging cell via an appropriate packaging signal (i.e., "ψ" signal) located on the reporter construct. Often, the packaging signal is located immediately downstream of the 5'LTR when the reporter construct is based on a retroviral vector backbone. Preferably, when the second reporter serves as an indicator of infection, the second reporter is a selection gene such that cell selection can be based on survival that is dependent upon the selection gene.

In preferred embodiments, the second reporter sequence codes for a reporter that can be quantified or detected by a high-throughput device, such as a flow cytometer, that does not necessitate lysis or killing of the cell. Flow cytometers are capable of sorting single-cells based on the reporter expression (or lack-thereof). Sorting can be sterile-sorting such that individual cells or gated-populations based on particular levels of reporter expression can be expanded in culture.

As discussed, the target sensor sequence can be located in the 3'UTR of the second reporter. When the second reporter is transcribed, the mRNA contains at its 3' end the target sensor sequence. If the corresponding RNAi molecule is also expressed from the reporter construct (i.e., if induced if under control of an inducible promoter), then the si-/shRNA molecule guides the RISC complex to mediate degradation, translational repression, or deadenylation of the mRNA (if the RNAi molecule has sufficient potency). The amount of mRNA destruction inversely corresponds to the amount of reporter expression from the cell; thus, more potent RNAi molecules result in less or no reporter expression from the cell.

4.2.4 Target Sensors

The target sensors of this invention include a target sequence to which a candidate RNAi molecule is complementary. Less than perfect complementarity can be used to determine off-target effects of shRNAs, to identify mi-RNA targets, and to determine sequence and/or structure requirements of the RNAi mechanism.

The target sequence is at least about 8 nucleotides in length. The target sequence can be derived from any gene of interest, including genes involved in diseases. For example, in cancer, the present invention is useful for identifying the most potent RNAi molecules targeting oncogenes, oncogene targets, oncogene co-factors, and genes required for cancer cell proliferation. The target sequence can be derived from any allelic variant of a gene for custom-designing RNAi molecules suitable for treatment of a given diseased individual or group of diseased individuals. For example, the present invention can target disease-specific fusion products resulting from chromosomal translocations. In addition, single nucleotide polymorphisms (SNPs) can also be specifically targeted with RNAi sequences complementary to a given SNP. The invention can also identify RNAi molecules that specifically target essential mutations occurring in diseases. This approach allows knockdown of only mutated mRNAs and not the "healthy," non-mutated mRNAs (and respective protein products).

In addition to the target sequence, the target sensor may optionally include a stretch of RNA sequence on either or both sides of the target sequence (flanking sequence) to help maintain the structure of the target sequence. The flanking sequence is obtained from the upstream and downstream sequences of the target sequence in the mRNA from which the target sequence of the target sensor is obtained. The flanking sequence may be the entire mRNA sequence. In one embodiment, the flanking sequence comprises at least 1 nucleotide. In one embodiment, the flanking sequence is from about 5 to about 25 nucleotides. In one embodiment, the flanking sequence is from about 10 to about 20 nucleotides. In one embodiment, the flanking sequence is about 15 nucleotides in length.

As discussed above, the target sensor in the reporter construct comprises a target sequence that is co-transcribed with a reporter sequence. The target sequence can be placed in any region of the reporter sequence that does not functionally alter the reporter protein. In preferred embodiments, the target sensor is in the 3' UTR or the 5' UTR. The target sensor can be under the transcriptional control of a constitutive promoter or inducible promoter. Such promoters are well known in the art. An advantage of using a constitutive promoter for this sequence is that the reporter can report on the transfection and infection efficiency of the reporter construct.

4.2.5 Comparison of Retroviral shRNA Expression Systems

The systems of the invention require suitable vectors that effectively express shRNAs. To assess suitability, expression vectors were compared for their efficiency in expressing well-characterized miR-30 based shRNAs (see Example 1). Two constitutive (MLP, MGPP) and one conditional (TGM) shRNA expression vectors were compared. With respect to these vectors, "constitutive" or "conditional" refer to the promoter controlling transcription of at least the RNAi molecule. Preferably, integrating viral vectors are used such that reporter cell lines can be easily infected at low MOI, and infected cells can be selected for (via selection markers carried by the vector constructs) and expanded due to the fact that the vectors integrate into the genome of the reporter cell line. The most important feature of such vectors are that they achieve stable integration in reporter cells, which can be adjusted to single copy, such that only one RNAi and one target sensor are present in a single reporter cell. The virus must also allow cloning of large RNAi/sensor libraries. Integrating viral vectors that can be used include, but are not limited to, avian virus-based vectors and retrovirus-based vectors, in particular, lentivirus based vectors such as those derived from HIV, FIV, and EIAV. Nonintegrating viruses can also be used, such as adenovirus, adeno-associated virus, or herpes-simplex virus-1, but these viruses mediate stable expression only in nondividing cells.

The data from Example 1 indicate that all tested vectors reliably express RNAi and induce target protein knockdown. This alleviated any concerns that the overall expression of shRNA from conditional promoters might be weaker than from constitutive promoters. Thus, in some embodiments, the methods can comprise a Tet-inducible retroviral system because: (1) knockdown efficacy is comparable to constitutive vectors, (2) inducible systems allow for temporal control of shRNA expression, which allows for the monitoring of potentially lethal RNAi molecules and which minimizes representational shifts in large RNAi pools, (3) off-Dox samples can serve as a direct control for the on-Dox samples, and (4) inducible systems allow several rounds of selection/sorting with increased signal to noise ratios.

4.2.6 Tetracycline-Responsive Promoter Systems

The efficacy of RNAi depends on its sequence composition and on that of its target site. In a conventional approach, the potency of RNAi sequences were tested by expressing the molecule and testing the suppression of the target mRNA (e.g., QRT-PCR, Northern blot) or its protein product (e.g., Western blot).

For high-throughput applications, a reporter-target mRNA fusion construct is used as a gauge for RNAi potency. For example, in one embodiment a stretch of the target mRNA, including a stretch of about 22 nucleotides complementary to the shRNA guide strand, is fused to a fluorescent reporter sequence. In another embodiment, the target region comprises a stretch from about 21 to about 22 nucleotides that is complementary to an shRNA guide strand. In another embodiment, the target region comprises a stretch from about 19 to about 22 nucleotides that is complementary to an siRNA guide strand.

In one embodiment, the expression of a given shRNA from the Tet-inducible promoter (or other promoter) knocks-down the cognate reporter-target mRNA construct expressed from an independent promoter cloned into the same vector (see FIG. 2A). In this embodiment, cells expressing a potent RNAi would lose expression of the fluorescent marker upon induction of the Tet-inducible promoter (addition of doxycycline in a Tet-On system) due to RNA interference. Cells expressing a weak RNAi would retain expression of the fluorescent marker due to the lack of a potent RNAi response. This differential expression of the fluorescent marker provides a way of distinguishing RNAi molecules exhibiting varying knock-down efficacy.

Cells expressing different levels of fluorescence (or no fluorescence) can be gated and sorted by flow cytometry. Potent knockdown cells (no fluorescence) can be differentially isolated from intermediate, weak, and no-knockdown populations. These populations can be expanded such that PCR can be performed to clone out the shRNA sequences into other plasmids, such as bacterial plasmids, which can be used to transform bacteria. In this manner, individual colonies contain a single RNAi sequence, and thus, each individual RNAi sequence can be analyzed. For larger pools, identification of individual RNAi sequences can be performed by other methods, such as hybridization on custom arrays.

Tetracycline (Tet)-responsive promoters can be used for in vitro and in vivo studies. Tet-On is a variation of the Tet-Off system (Gossen and Bujard, (1992), *Proc. Natl. Acad. Sci. USA*, 89:5547-5551), and features a modified Tet repressor that has reversed DNA binding properties when compared to the wild-type Tet-repressor (tetR) encoded in the Tn10 Tet-resistance operon of *E. coli*. The reverse tetracycline-controlled transactivator (rtTA) is made from a Tet-repressor fused to the activating domain of virion protein 16 (VP16) of herpes simplex virus (HSV). In contrast to the Tet-Off system, the Tet-On system is optimized for induction by the Tet-analogue doxycycline (Dox) only.

Expression of rtTA can be driven by a constitutive promoter of choice. When rtTA is expressed, the presence of Dox leads to a conformational change and binding of rtTA-Dox to the Tet operator sequence (tetO) of the Tet-resistance operon. Seven serial tetO sequences were fused to a minimal cytomegalovirus (CMV) promoter and termed the Tet-responsive element (TRE). The binding of rtTA-Dox, therefore, induces the expression of a gene of interest from the minimal CMV promoter. Thus, by placing an shRNA under the control of the TRE, the expression of the RNAi molecule is inducible by the addition of Dox.

Various Tet-inducible vectors and cell lines were characterized (see Example 2). For example, the Tet-inducible vector TRMPV was tested in a fibroblast cell line (Rosa-rtTa p53−/− MEF) expressing the reverse Tet-transactivator (rtTA). The TRMPV vector contains two important features: (1) a yellow fluorescent protein (Venus; V) reporting infection efficiency, and (2) a red fluorescent protein (DsRed2; R) reporting induction of RNAi expression. (See FIG. 3A.)

Figure 3A:
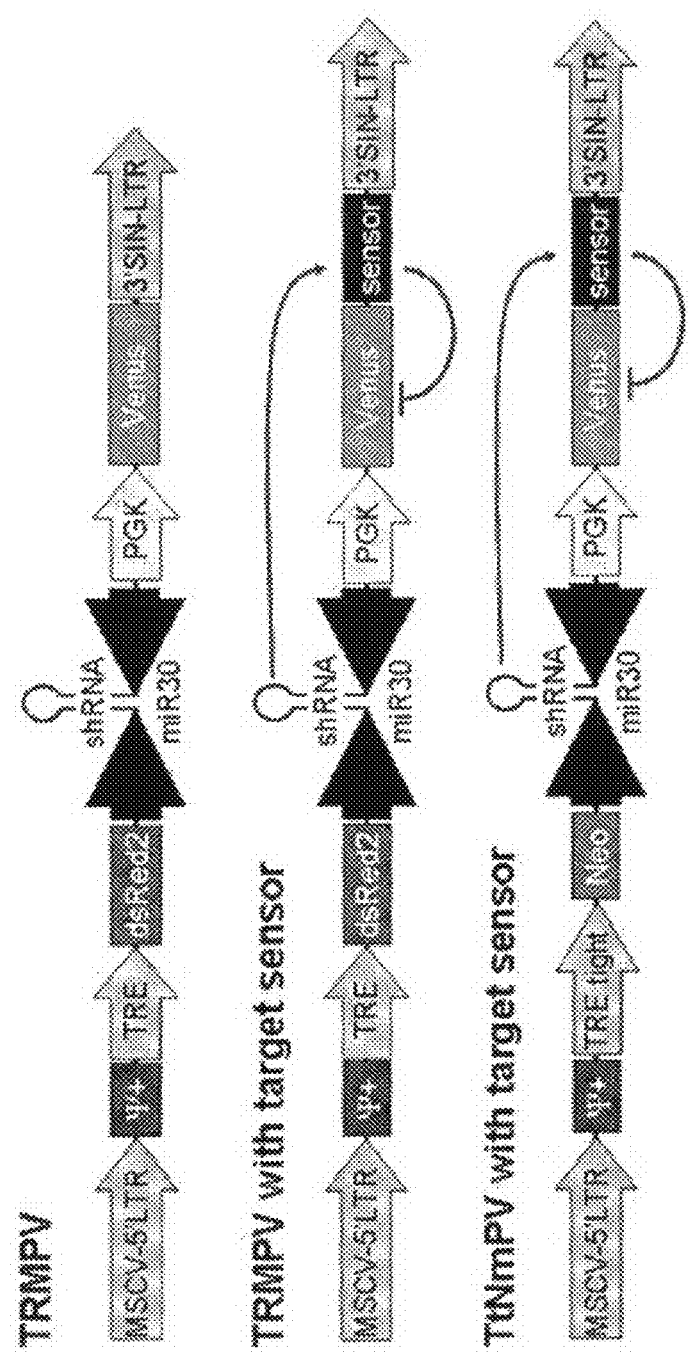
Figure 3B:
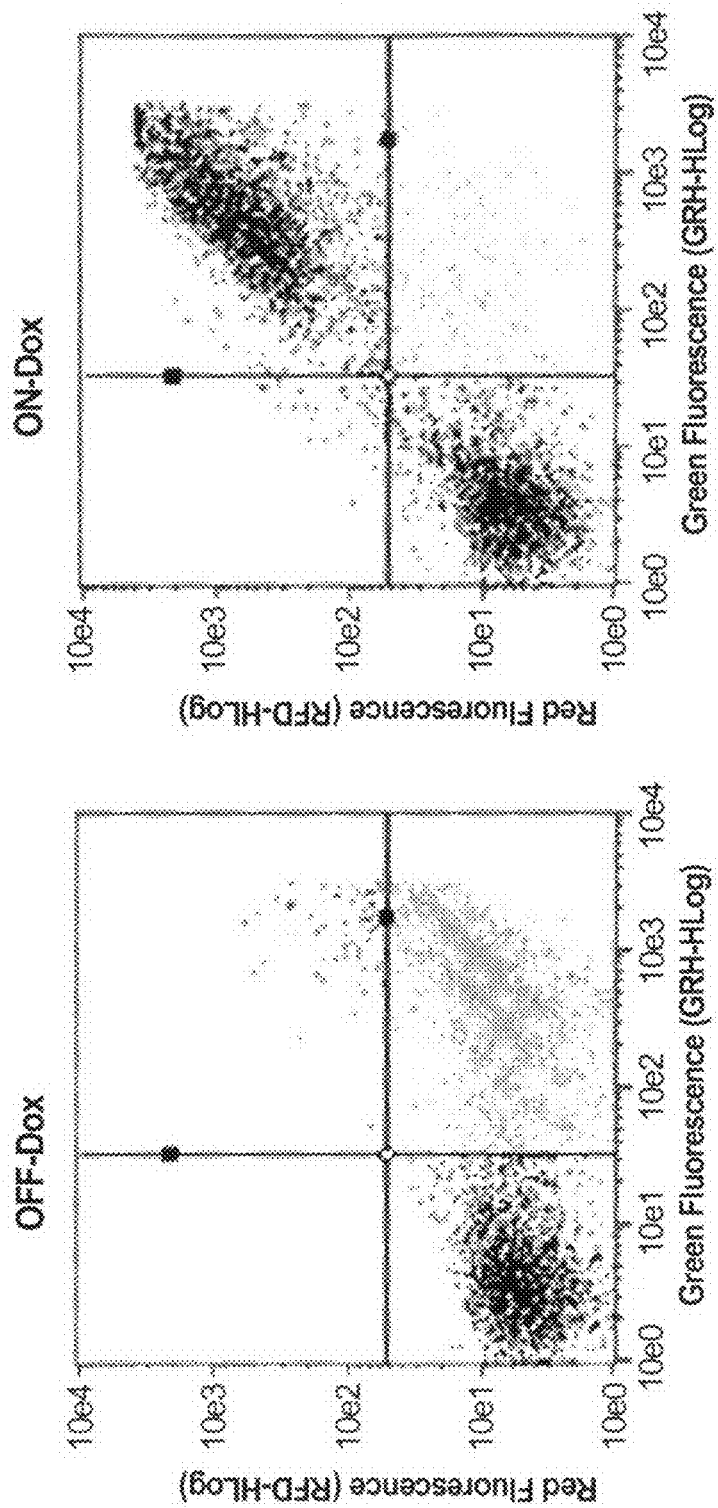
Figure 3C:
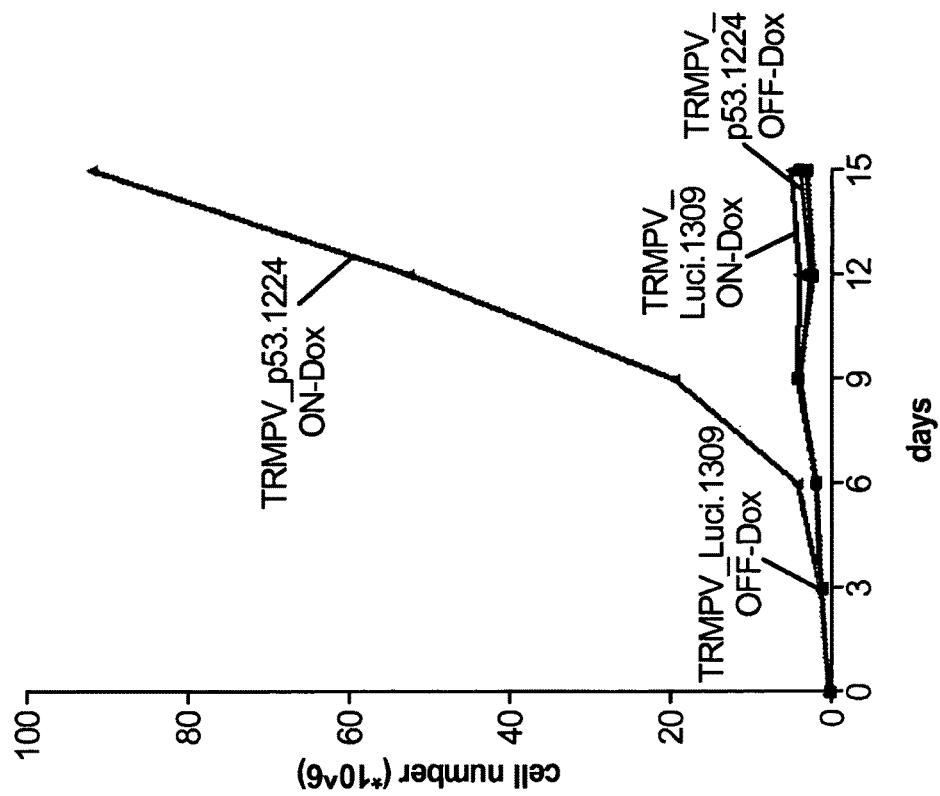
Figure 3C:
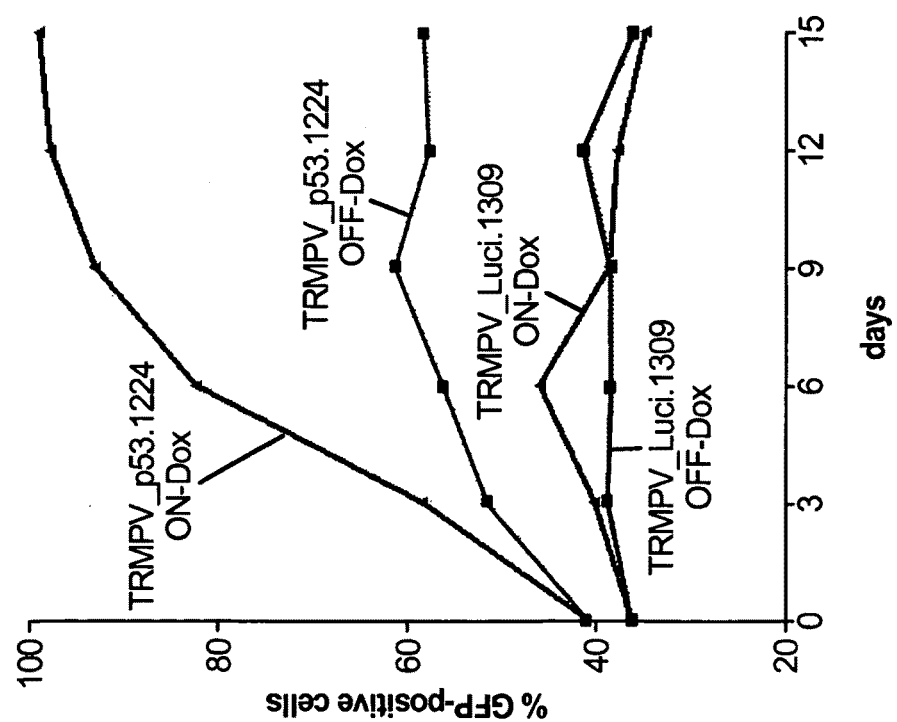
Figure 3D:
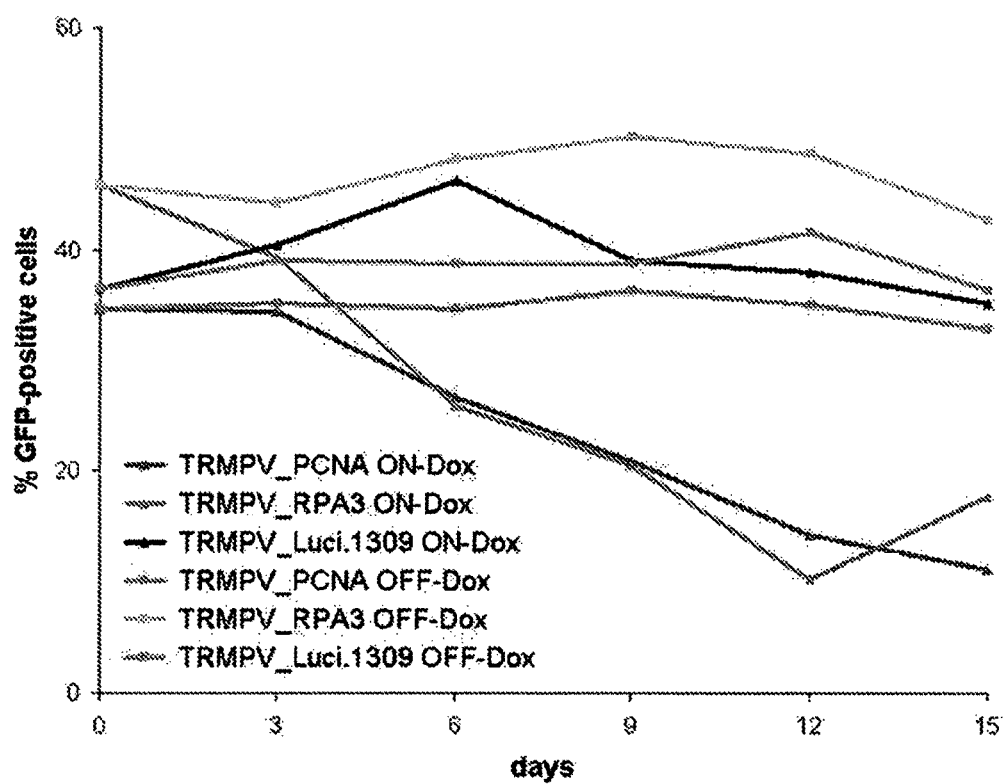

Experiments with Tet-inducible vectors (see Example 2; FIGS. 3B-3D) showed that the infection efficiencies and the induction of RNAi expression are suitable for the methods of the invention. Leakiness of the TRE promoter Off-Dox was observed. Thus, the TRE promoter was compared side-by-side with the enhanced TREtight promoter to see whether the leakiness issues could be addressed (see FIG. 4A). The TRE-tight promoter resolved the leakiness issue while retaining the same infection and induction efficiencies.

The cell line, Rosa-rtTA p53−/− MEF (MEF cell line), was also tested for its suitability for use in the reporter assay methods herein. It was compared to two commercial Tet-inducible cell lines (U2OS-rtTA and HepG2-rtTA; see FIG. 4B). The MEF cell line was more easily infectable and showed much higher induction rates than the two commercial cell lines. A transgenic cell line is preferred over a stably transfected one because the Sensor assay requires a very consistently working tet-On system. The experiments with commercially available stably transfected rtTA cell lines (U2O5-rtTA, HepG2-rtTA) showed only mediocre induction of the TRE promoter upon Dox treatment in vitro.

While the MEF cell line is suitable for use in the invention, it was desirable to create a cell line generally insensitive to effects of the analyzed RNAi molecules on endogenous gene function. To decrease the number of possible endogenous RNAi targets, such a cell line must be derived from an organism evolutionary distant from the organism for which RNAi sequences are evaluated. Concomitantly, the cell line must process miR-30 based shRNAs and correctly predict shRNA potency, which implies that the structural requirements for shRNA processing as well as target recognition and cleavage have to be identical.

A monoclonal, bitransgenic chicken embryonic fibroblast (CEF) cell line expressing the rtTA3 reverse tet-transactivator and the EcoR ecotropic receptor was established and characterized. (See Example 3.) The rtTA3 is an improved variant of the reverse tet-transactivator, showing a more sigmoidal induction curve, which is a result of less background activity Off-Dox (tet-On system) and full induction of transgene expression at lower doxycycline (Dox) concentrations (Urlinger et al., (2000), *Proc. Natl. Acad. Sci. U.S.A.* 97, 7963-7968). EcoR was introduced to allow for secondary infections with ecotropically packaged retroviruses, thereby reducing the biohazard when working with the resulting cell line. Furthermore, a monoclonal cell line is preferred over a polyclonal one due to position effect variegation of retroviral insertion sites, insertional mutagenesis and transgene dosage associated variations.

4.2.7 Confirmation of the Sensor Approach

The Sensor Approach allows for the high-throughput screening of libraries of reporter constructs of the invention that are capable of having a tiled representation of RNAi sequences for any given target gene. The experiments described in Example 2 confirmed the capability of cells and vector systems for testing the Sensor approach. Packaging cell lines, such as Phoenix Eco, HEK293T, were transfected with vectors containing both a shRNA and either its cognate target=−mRNA fragment or a control fragment coupled to the fluorescent reporter. (See Example 4.) The potent RNAi molecules knocked-down the fluorescent reporter when coupled to the cognate target sensor and did not interfere with the expression of the fluorescent report in case of a control sensor. This provided proof of concept for the Sensor approach. (See FIGS. 5A and 5B.)

However, when viral vectors are used as the reporter vector, unwanted knock-down effects can occur during packaging. In particular, packaging cells include three independent transcripts: (i) the viral transcript driven by the LTR, which is the provirus; (ii) the leaky TRE transcript; and (iii) the PGK-reporter-target sensor transcript. (See FIG. 5B.) Transcripts (i) and (ii) contain the shRNA; all three transcripts contain the target sensor. As a consequence, RNAi will be produced and knock-down all three transcripts, which means that the provirus will be reduced and the most potent shRNA will be least efficiently packaged.

Therefore, the RNA interference machinery in the packaging cell line must be disabled. This can be achieved by suppression of its essential components (e.g., DGCR8, Drosha, or Exportin-5) using siRNAs or drugs, or by the production of new transgenic packaging lines deficient for essential RNAi components. Example 4 shows knockdown of DGCR8 using siRNAs and demonstrates that RNAi is disabled and efficient packaging is restored. (See FIG. 5C.)

As shown in Example 4, cells infected with viruses containing shRNA-target sensor reporter constructs showed that the suppression of the fluorescent marker was dependent on doxycycline concentration, proving the specificity of the RNAi response. Further, Example 4 shows that the Sensor approach can correctly predict RNAi knockdown efficacy, or in other words, the measured fluorescence intensity of an infected cell correlates with the potency of the expressed RNAi.

4.2.8 Improvements to the Tet-Based Reporter Vector

In the first version of the reporter vector (TRMPV), the fluorescent reporter dsRed2 was expressed from the Tet-promoter to monitor efficient expression of the shRNA, which was positioned in the 3'UTR of dsRed2. However, the emission of dsRed2 interfered in flow cytometric measurements with sensitive detection of Venus, which was used to report RNAi potency. Thus, DsRed2 was replaced by a neomycin selection marker that had previously been shown to be an ideal spacer, enhancing shRNA expression in the context of miR-30 based retroviral vectors. The Neo-coding region was thus cloned into the TtRMPV vector, leading to TtNmPV (5'-TRE-tight; Neo; miR-30-shRNA; PGK; Venus; target sensor-3'), which has been tested to be at least as good as TRMPV for its infection and induction potential. (See Example 4.)

Thus, in some embodiments, the reporter vectors of the invention comprise a first reporter that reports RNAi expression, and can provide a spacer to make RNAi more potent. The first reporter can indicate whether a cell contains the reporter vector; alternatively, a second reporter can be used for this purpose. The reporter can be, for example, a fluorescent-protein encoding gene or a selection gene. If the first reporter is a fluorescent-protein encoding gene, then the protein emits a different light wavelength that can be distinguished from the light wavelength emission of a second reporter contained in the reporter vector.

4.2.9 Additional Control Elements

In addition to those mentioned above, the reporter constructs of this invention may also include transcriptional control elements, such as enhancers, and transcription initiation and termination sequences. The choice of promoters and other regulatory elements generally varies according to the intended host cell. The regulatory elements can be derived from mammalian, avian, microbial, viral or insect genes. The ability to replicate in a host, usually conferred by an origin of replication, and a selection gene to facilitate recognition of transformants (e.g., ampicillin-resistant gene for E. coli transformant selection), may additionally be incorporated.

The reporter constructs of this invention can be viral-based, i.e., containing genetic elements from viruses such as retroviruses, including lentiviruses, adenoviruses, avian viruses, and baculoviruses, such that the constructs can be packaged and infect host cells. In some embodiments, the reporter constructs can comprise a 5'LTR, a packaging signal, a first promoter controlling expression of a first reporter and the RNAi molecule, a second promoter controlling expression of a second reporter whose transcript contains the target sensor, and a 3'LTR. In some embodiments, constitutive mouse stem cell virus (MSCV)-based shRNA vectors or other retroviral-based vectors featuring the conditional Tet-On system are used.

To minimize the effect of RNAi on the replication and packaging of viral-based reporter constructs, packaging cells can be pre- or co-transfected with, for example, an si/shRNA molecule that interferes with the RNA interference pathway in the cells. For example, an RNAi molecule against DGCR8, Drosha, or Exportin-5 can be used.

4.2.10 Host Cells

The reporter constructs of this invention can be produced using well known recombinant technology in, e.g., bacterial (E. coli) host cells. The constructs can then be further studied in eukaryotic cells such as yeast cells, insect cells, avian cells, or mammalian cells. The constructs can be delivered into host cells via a variety of methods, including but not limited to, liposome fusion (transposomes), viral infection, and routine nucleic acid transfection methods such as electroporation, calcium phosphate precipitation and microinjection. Useful cell lines for studying the reporter constructs and RNAi libraries of the invention include mammalian cell lines such as mouse embryonic fibroblasts (MEF).

In embodiments where the reporter construct is a virus-based construct, the reporter constructs are packaged into virions by transfecting the reporter constructs into producer or packaging cell lines. These producer or packaging cell lines produce virions that contain the reporter construct. The virions can then be used to infect host cells that are capable of infection by the virion. Thus, in some embodiments, the viral construct is an ecotrophic or amphotropic virus-based construct, such that certain mammalian host cells can be infected.

In some embodiments, to minimize endogenous RNAi effects, cell lines from a species that is different from the source of the RNAi molecules are used. For example, to study human or mouse shRNA knockdown efficiency, chicken cell lines can be used. In some embodiments, the cell lines have been modified to include genes for components of an inducible transcription control system, such as rtTA for the TET-On system.

In one embodiment, the cell line is a monoclonal, double-transgenic chicken embryonic fibroblast (CEF) cell line expressing the rtTA3 reverse Tet transactivator and the EcoR ecotropic receptor. Because the reporter assay is most reliable with a consistent inducible system (such as a non-leaky Tet-On system), a transgenic cell line is preferred.

4.3 High Throughput Applications of the Sensor Approach

Tiled Screening 4.3.1 Assessing the Reporter Construct Potential for Pooled shRNA Efficacy Evaluation Strategies were established for conducting sensor-based RNAi screens in a pooled manner. As used herein, the term "pooled" means that a population (such as a library) of reporter constructs, each containing a different coupled pair of RNAi molecule coding sequence and cognate target sensor sequence, is mixed together and concomitantly transfected into packaging or reporter cells (packaging cells if retroviral-based reporter constructs—where the resulting viral supernatant is then used to infect reporter cells), such that the whole pool or population of transfected/infected reporter cells can be assayed in a high-throughput manner.

As mentioned, intensity of the marker whose mRNA contains the target sensor sequence is the readout for RNAi knock-down efficacy. Thus, if RNA interference occurs due to the presence of a strong RNAi the transformed cell loses expression of the marker.

The inherent link between phenotype (e.g., cell is not green or cell is green) and genotype (e.g., potent shRNA or weak shRNA, respectively), guaranteed through the single plasmid approach (coupled RNAi molecule and target sensor in the same vector) developed here, provides the ability to apply high-throughput flow cytometry for separating RNAi molecules of varying potency.

Potent RNAi can be identified through PCR from genomic DNA of cells, sorted/selected for those that report the presence of powerful RNAi. Specific PCR products can be generated using the RNAi encoding region or the target sensor region. In one scenario, the whole shRNA is amplified and subsequently cloned into target vectors and directly used for downstream applications. In a second scenario, high-throughput applications, such as second generation sequencing or hybridization to customized microarrays carrying oligonucleotides complementary to the RNAi pool are used to identify the entirety of RNAi contained in the selected/sorted cell population. Other possible assays to identify potent RNAi molecules include immunologic separation methods and lethal escape assays. In the former, cells expressing potent RNAi sequences lose surface marker expression and consequently do not bind certain antibodies. This method is used in conjunction with immunoseparation columns or immunomagnetic methods. In another embodiment, if the reporter sequence is a lethal gene, cells expressing potent RNAi molecules repress the lethal gene and are more likely to escape death, as assessed using cell culture assays.

As shown in Example 5, the feasibility of such a pooled RNAi knockdown efficacy evaluation was proven. Twenty different retroviral-based reporter constructs were transfected into packaging cells. The produced viruses were infected into RAg MEFs at low MOI. The cells were then treated with or without Dox and separated on a flow cytometer into different fractions. From every fraction, genomic DNA was extracted and shRNAs sub-cloned into vectors for sequencing. The distribution of RNAi molecules in the different fractions were analyzed and ranked. The fact that the RNAi ranking suggested by this Sensor approach correlated with Western blot analyses proved the assay's capability of evaluating RNAi in pools as well as its ability to detect the smallest possible difference between two RNAi molecules, a shift by only one base pair. More generally, the results proved that the Sensor approach allows one to evaluate RNAi knockdown efficacies in pools as well as identifying, separating, and sub-cloning RNAi sequences of a given potency.

4.3.2 Creating a Tiled Library: Strategies for Pooled Cloning of Large shRNA-Target Sensor Libraries As used herein, the term "tiling" or "gene tiling" refers to the process of producing every single RNAi for a given transcript. Thus, a "tiled library" refers to a population of RNAi sequences that in sum represent every possible or almost every possible RNAi sequence for a given transcript. See FIG. 14 for a schematic of tiling.

Tiled libraries can be used to evaluate computationally predicted RNAi in order to create a new library of computationally biased but biologically validated RNAi molecules. Another application is to develop a library containing all possible shRNAs against a set of genes with the aim of identifying the most potent RNAi molecules, independent of design algorithms.

In order to obtain potent RNAi reagents that ultimately lead to good loss-of-function phenotypes for research or treatment, one has to be able to select the most potent RNAi sequences out of the hundreds to thousands of possible sequences for a given gene. Selection requires being able to synthesize, evaluate, identify, and separate the potent RNAi molecules from the dominating bulk population of non-functional and weak sequences. This requires a method for pooled cloning of large libraries of shRNA-target sensor constructs.

Reporter construct libraries of the invention comprise a mix of equal vectors (such as TtNmPV for example) that each contains a different coupled pair of RNAi coding sequence and its cognate target sequence. By pooled cloning, all desired coupled pairs are cloned together into the reporter construct backbone. (See FIG. 15.) This is in contrast to the prior art, where constructs for expression of the RNAi molecule and for reporter-target readout were constructed sequentially, which is technically unfeasible for larger pool sizes.

On-chip synthesis technologies allow for the production of oligonucleotides with a length of up to about 200 nucleotides. Thus, each shRNA and its cognate target sensor can be synthesized on a single oligonucleotide. Cloning such an oligonucleotide into an appropriately cut reporter construct backbone (see TtNmPV vector at FIG. 15) and subsequently cloning the missing part of the vector into the product of the first cloning step guarantees the essential coupling between a given shRNA molecule and its cognate target sequence. (See FIG. 15.) Following this strategy, a pool of approximately 20,000 shRNAs and their cognate sensors were cloned into TtNmPV. In this pool, all possible shRNAs for chosen genes were present.

In order to retain every shRNA-target sensor construct of the initial pool throughout all cloning steps, as well as through all the other steps of the reporter assay, it is important to always guard a representation of 1000×. This means that in this example, every step at least $20 \times 10^6$ (20,000×1,000) oligonucleotides, vectors, or cells had to be present. Successful cloning and retention of the initial representation was confirmed by SOLEXA deep sequencing.

4.3.3 Evaluating, Identifying, and Separating Potent si-/shRNAs Out of Large Pools In one embodiment, cells that have been transformed with a pool or library of reporter constructs are analyzed by flow cytometry. For the fluorescence activated cells sorting (FACS), at least two different sorting strategies can be used.

The first is based on treating target cells transformed with reporter constructs comprising an inducible promoter controlling RNAi molecule expression with and without the agent that induces the promoter (i.e., Dox for Tet-On promoters). Treated and untreated cells are then sorted into different fractions (for example—see Tiled-sensor 4 way sorting strategy FIG. 16). The distribution of reads for a given RNAi over the four fractions On-Dox was compared to its distribution Off-Dox. Cells containing potent RNAi molecules shift into the fractions with low marker expression when On-Dox, while showing equal distribution Off-Dox. Inversely, weak RNAi molecules would enrich in the high marker expression fractions On-Dox as a consequence of the potent RNAi shifting downwards. (See FIG. 16.)

The second sorting concept is based on directly assessing the fluorescence-shift (i.e., green-shift for Venus reporter gene) of inducible shRNA-target sensor constructs through sorting. To implement this, all transformed cells are first treated with the inducing agent for the inducible promoter controlling RNAi expression. Then in a first sorting step, cells are sorted for low fluorescence (i.e., for low GFP or Venus expression). Then, in a second sorting step, the sorted cells are kept in culture without the inducing agent (i.e., doxycycline) and then sorted for high reporter expression. In this strategy with an inducible promoter, the first sorting step allows one to sort for transformed cells that show low GFP expression and, hence, contain correctly synthesized potent shRNA-target sensor constructs. The second sorting step then allows separation of cells transformed with potent shRNAs (low GFP On-Dox; high GFP Off-Dox) from the ones that were selected in the first round due to unfavourable integration sites of the vector (low GFP On-Dox; low GFP Off-Dox). (See FIG. 17.) Thus, this second sorting strategy allows selection of potent shRNAs from a pure library and also permits separation of potent shRNAs from a population with large percentages of background noise.

4.3.4 Proof of Principle Using the Sensor Approach with Tiled Libraries

The invention provides methods to identify the most potent RNAi molecules for any given gene, independent of design algorithms. To do so, one can generate all possible RNAi sequences targeting a certain mRNA and experimentally determine the most potent ones amongst them in a high throughput manner. This approach is sometimes referred to herein as "tiled target sensor" or "tiled sensor" screening.

Tiled sensor screening will yield a unique dataset to further elucidate parameters that govern the efficiency of RNAi. The tiled sensor approach identifies potent RNAi triggers from a large set of shRNAs containing every possible shRNA targeting a given transcript, and therefore is not biased towards any pre-existing design rules. From the tiled sensor screening results, one can use various bioinformatics strategies (1) to search for new sequence autonomous parameters defining potent RNAi molecules, and (2) to implement the data in prediction algorithms (both linear models and models based on artificial neuronal networks or support vector machines and their derivatives, e.g., S3VM/TSVM) to improve existing design strategies.

As mentioned above, the inherent link between phenotype (e.g., the cell is or is not green) and genotype (weak or potent RNAi, respectively), guaranteed through the single plasmid approach developed here (coding sequences for the RNAi and target sequence are cloned into the same vector), offers a unique opportunity to apply high throughput flow cytometry to separate RNAi sequences of varying potency. Potent shRNAs can subsequently be cloned into target vectors and used for downstream applications, including therapeutic applications.

A high throughput method is advantageous because it allows for (1) screening of a large number of reporter constructs at one time, and (2) facile comparison of the knockdown ability and efficiency of different RNAi constructs. High throughput screening can be used to quickly identify potent interfering RNA molecules which may be used as a research tool or as therapeutic agents. It may also be used to compare knockdown efficiency of different RNAi constructs.

The disclosure provides a completed study of large-scale experiments using a pool of approximately 20,000 different TtNmPV shRNA-sensor plasmids covering every possible shRNA of eight mouse and one human mRNAs. Besides having 20,000 tiled shRNA-sensor oligos, oligo library chips also carried 18 different control constructs with known knockdown potencies (FIG. 18), which had been previously tested in MiniPool experiments. The presence of these control oligos as well as sufficient representation of the whole pool was verified by SOLEXA sequencing.

After retroviral transduction of RAg MEF reporter cells, the second sorting strategy ("backshift approach;" see FIG. 17) was conducted. Genomic DNA was isolated from 2 replicates of 10 million sorted cells obtained from the second sort as well as from unsorted control cells. SOLEXA deep sequencing was applied to identify shRNA representation in both sorted and unsorted samples. To prepare SOLEXA samples, the specific shRNA guide sequences with flanking primers containing 5' overhangs were amplified, which also tag SOLEXA adaptors onto PCR products.

Results of deep sequencing demonstrated the presence of 92% of synthesized shRNAs in the unsorted and sorted population. Changes in relative read numbers indicated enrichment or depletion of a certain shRNA during the assay. For example, among the 18 control shRNAs, there was an enrichment for very potent control shRNAs, while weak or dysfunctional control shRNAs were strongly depleted. Analysis of the whole dataset demonstrates that the majority of shRNAs are strongly depleted and only potent shRNAs appear to be enriched using the backshift approach.

An additional sorting step can be included in this approach to further enrich potent shRNAs. This is called an enhanced backshift strategy or Sensor Ping-Pong. (See FIG. 19.) The Sensor Ping-Pong approach is a reference shRNA guided sorting strategy allowing functionally assessing shRNA potency through iterated cycles of suppression and derepression of marker protein expression. The strategy enables isolation of subfractions of cells containing the most potent shRNAs from large, highly complex shRNA libraries.

Thus, a first sort after selection (i.e., +Neo) and induction (i.e., On-Dox) on low reporter (i.e., the reporter with the target sensor integrated into the UTR) expressing cells depletes all weak shRNAs that were not correctly synthesized, while enriching for potent shRNAs. The second sort for reporter expression without induction (i.e., Off-Dox) depletes badly integrated shRNAs (i.e., with retroviral constructs that integrate at a site that interferes with the function of the TRE promoter) and enriches potent shRNAs. A third sort after induction and selection for low reporter expression further enriches for potent shRNAs that show a large GFP shift after the second round. This Ping-Pong strategy is particularly useful if the expected amount of potent RNAi molecules is low, like it is in the case with gene-tiling screens.

Figure 20A:
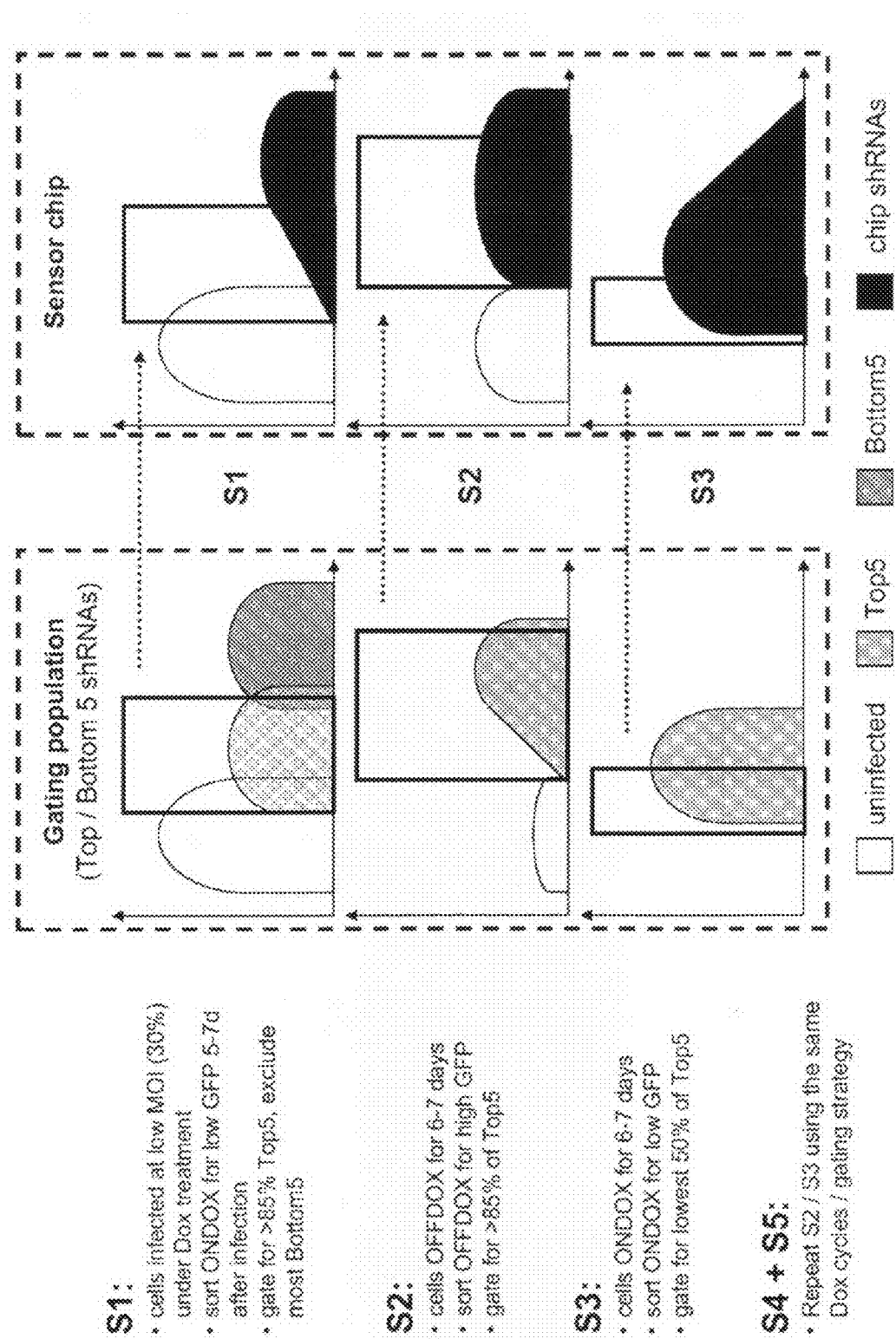

The second and third sorts can also be repeated using the same Dox cycles and gating strategy. (See FIG. 20A.) Repeated cycles of induction and sorting are referred to herein as "Sensor Ping-Pong." Results from screening and sorting tiled libraries using the Sensor Ping-Pong strategy shows that this method accurately enriches for the most potent shRNAs (FIG. 20B), where with each round the complexity of the library is reduced and more potent species increase in representation (FIG. 20C; 20D). FIG. 20G shows that two potent siRNA prediction algorithms, Biopredsi and DSIR, both queried for their ten highest-ranking shRNAs, were only able to predict one or two of the most potent shRNAs of a tiled library to the p53, Bcl2, PCNA1, Hras, and mMyc genes, and were not able to predict any of the most potent shRNAs for Mcl1, Rpa3, Kras, and hMyc. These results underscore the deficiencies of prediction algorithms and the clear advantage of using the methods of the present invention.

4.4 Extended Applications of Sensor Approach

In addition to screening for potent RNAi molecules, the reporter assay of the present invention provides other high throughput applications by modification of the RNAi molecule or target sensor using the same procedures described, wherein other oligonucleotide sequences are synthesized on the initial chip. These additional applications include: off-target analysis, miRNA target identification and/or validation, and analysis of structural requirements of the RNAi machinery for pri- or pre-miRNA processing and target regulation.

For off-target analysis, selected shRNAs are combined with target sensors representing all possible target sequences in the genome of the cell in which the RNAi will be finally used. Possible targets include all sequences having a complete seed sequence match, i.e., nucleotides 2 to 8 on the guide strand. Such a strategy can also imply rules that help eliminate RNAi triggers with undesired off-target effects. This leads to increased knowledge about structural, sequence-specific target recognition.

In another application, miRNAs can be cloned as RNAi molecules either with their naturally occurring bulges and/or mismatches in the stem, or with a completely complementary passenger strand. Targets can be chosen as described for off-target analysis. This screening can reveal functional miRNA targets, providing insight into the biology of miRNAs and their function, which can lead to the discovery of novel genes, e.g., tumor suppressor genes or oncogenes.

The structural requirements for shRNA processing can be analyzed by cloning known shRNAs as RNAi molecules with bulges and/or mismatches in the stem, such that the passenger strand is not 100% complementary. The effects of these alterations on target knockdown can be analyzed with the sensor approach and advantageous modifications can be used for the design of new, more potent RNAi triggers.

The requirements for target mRNA regulation can also be analyzed using the present invention. Known shRNAs or known targets can be combined with their respective counterparts (target sensor or RNAi molecule), wherein bulges or mutations are present. This method determines whether shRNAs that are not 100% complementary mediate stronger target knockdown.

The results of the target sensor assay provided by the present invention can inform optimal designs for all types of RNAi triggers, regardless of the type of trigger used in the assay. It is of particular interest to optimize siRNAs, as this type of RNAi has great potential in a therapeutic context. The methods described herein provide the best possible strategy for optimizing siRNAs and identifying those that are most potent against any given gene.

As demonstrated in the following Examples, the invention provides various new reagents, methods, and experimental protocols, including:
1. The miR30 shRNA-sensor vector (TtNmPV and its derivatives): A retrovirus derived from the pQCXIX retroviral backbone (Clontech), which contains a TREtight-driven Neo-miR30-shRNA transcript and a PGK-driven Venus-target sensor transcript.
2. Various reporter cell lines expressing the reverse tet-transactivator (rtTA) or its improved derivative (rtTA3). Two lines (RAgMEF and DF1ER3) were generated by the inventors and are used as reference reporter cells.
3. An improved retroviral gene transfer protocol involving co-transfection of DGCR8 to guarantee equal retroviral transduction independent of shRNA effects.
4. The shRNA-sensor assay, which directly correlates shRNA potency with the suppression level of Venus expression from the Venus-target sensor mRNA. This assay has been demonstrated to accurately predict RNAi potency.
5. A cloning strategy to generate large pools of shRNA-sensor constructs from chip-synthesized oligonucleotides.
6. Pooled sensor approaches, including specific culture protocols, as well as different flow-cytometry based assays facilitating the isolation of cell fractions depending on the level of shRNA mediated Venus suppression. The now commonly used Ping-Pong strategy involves two or more sorting rounds to enrich sequentially for cells with significant shRNA-mediated changes in Venus expression levels. To contrast the shift of Venus expression, cells are cultured alternately with and without doxycycline between the sorts.
7. Protocols to recover the representation of individual shRNAs in unsorted and sorted cell populations using Solexa sequencing. Those protocols include a customized PCR strategy for recovering shRNA guide sequences from genomic templates and tagging them with Solexa adaptors, as well as computational strategies and programs to perform statistical analyses on that data.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention.

All publications and other references mentioned herein are incorporated by reference in their entirety, as if each individual publication or reference were specifically and individually indicated to be incorporated by reference.

5. EXAMPLES OF THE INVENTION

The following examples are meant to illustrate the methods and materials of the present invention and are not intended to limit the invention in any way.

5.1 Example 1

Comparison of Retroviral shRNA Expression Systems

In order to constitute a suitable system for the planned reporter assay, exemplary retroviral vectors were analyzed for their potential in expressing shRNAs. Two constitutive (MLP, MGPP) and one conditional (TGM) shRNA expression vectors were compared side-by-side for their efficiency in expressing well-characterized miR-30 based shRNAs. Two shRNAs against p19-Arf (sh.Arf.157 and sh.Arf.218), one shRNA against p53 (sh.p53.1224), and an empty miR-30 control were tested.

Knock-down efficacy was tested for Arf in p53−/− MEFs cells and for p53 in NIH3T3 (Arf−/−) cells. Both cell lines were twice infected with pRevTetOFF (Clontech) carrying an LTR-driven tetracycline transactivator (tTA) and a neomycin resistance gene. In the absence of Dox, tTA served as an inducer of the TRE on the TGM vector (Tet-Off system). After selection for tTA integration, the cells were infected at low MOI (generally less that about 60% infected cells, here always less than about 30% infected cells) and high MOI (more than about 80% infected cells) with vectors containing the respective shRNAs. Vector integration into the genome was ensured by puromycin treatment. Subsequently, complete selection as well as efficient TRE promoter activation (for TGM samples) was verified by flow cytometry using the GFP reporter present in all three constructs.

At a purity of >95% GFP positive cells, protein was obtained from total lysates and shRNA knockdown efficacy analyzed on Western blots. The results showed that all tested vectors reliably express potent (sh.p53.1224) and intermediate (sh.Arf.157, sh.Art.218) miR-30 based shRNAs and, therefore, induce target protein knockdown.

The number of genomic integrations of a given shRNA expression vector can impact judgment on shRNA efficacy. At high MOI even inefficient vectors led to strong target protein knockdown and weak shRNAs became potent due to multiple integrations. Thus, individual shRNAs have to be used at single-copy integration per cell in order to retain the direct correspondence between phenotype and genotype.

In these particular experiments, a Tet-inducible retroviral system seemed most suitable on the following basis: (i) knockdown efficacy was comparable to constitutive vectors; (ii) the inducible system allowed for temporal control of shRNA expression, enabling potentially lethal shRNAs to be assayed and minimizing representational shifts in large shRNA pools; and (iii) Off-Dox samples could serve as direct control for the On-Dox samples.

5.2 Example 2

Evaluation of Suitable Tet-On shRNA Expression Systems shRNA specificity and efficiency is affected by at least the loading of the shRNA guide strand into the RNA-induced silencing complex (RISC), and target mRNA recognition. While loading into the RISC is a highly complex mechanism, target recognition may be based on either sequence specificity or the three-dimensional structure of a transcript. In the case of assessing sequence specificity, a reporter-target sequence fusion construct can gauge shRNA potency as well as siRNA potency. For example, a stretch of target mRNA comprising 22 nucleotides (nt) complementary to the shRNA (or siRNA) guide strand may be fused to a fluorescent protein gene driven from an independent promoter. The target length can be at least 16 nucleotides, and is preferably at least 19-22 nucleotides, as short siRNAs can bypass Dicer cleavage and be integrated into the RISC complex at lengths shorter than 22 nucleotides.

Subsequently, this construct may be cloned into an si-/shRNA expression system, such as a Dox-inducible Tet-On shRNA vector (FIG. 3A) and transfected into host cells. Cells expressing a potent si-/shRNA for the target mRNA will lose expression of the fluorescent protein marker upon Dox treatment due to the si-/shRNA-mediated degradation of the reporter gene-target construct. On the other hand, cells expressing a weak si-/shRNA will remain fluorescent since only a minimal degradation of the reporter gene-target construct will result.

The vector TRMPV was chosen for making reporter gene-target constructs in these experiments. This vector has a dsRed2 fluorescent marker to monitor the induction of shRNA expression. This marker can provide such a monitoring function because its sequence is cloned between the inducible TRE promoter and the miR-30 based shRNA cassette (FIG. 3A), such that the TRE promoter controls transcription of both the dsRed2 message and the shRNA molecule. In addition, the PGK-promoter driven Venus marker in the vector allows for the detection of infection efficiencies (as well as being a marker of knockdown). Venus was chosen because of its enhanced fluorescence emission compared to conventional GFPs (insufficient fluorescence when driven by the PGK promoter) and its rapid maturation (Nagai et al. (2002), *Nat. Biotechnol.* 20, 87-90, the contents of which are hereby incorporated by reference).

5.2.1 Vector Infection and Induction Efficiency

The TRMPV vector was tested for its ability to conditionally express shRNAs in the Rosa-rtTA MEF cells that had been previously used for Tet-On assays (Dickins et al. (2007), *Nat. Genet.* 39, 914-921, the contents of which are hereby incorporated by reference).

First, the infection and induction efficiency of TRMPV in Rosa-rtTA MEFs was determined. The results showed that Rosa-rtTA MEFs could easily be infected at 50% and higher (FIG. 3B). When these cells were treated with Dox, shRNA expression was observed in >90% of the infected cells.

Next, a positive selection assay was performed in Rosa-rtTA MEFs with TRMPV constructs expressing either a growth promoting p53 shRNA (sh.p53.1224) or a neutral Luciferase shRNA (sh.Luci.1309). When treated with Dox, cells infected with sh.p53.1224 grew out, raising the percentage of infected cell from initially about 40% to nearly 100% over the next fifteen days (FIG. 3C, left and right panels). By contrast, when keeping the same cells Off-Dox, the percentage increased to about 60%. The control sh.Luci.1309 did not affect the percentage of infected cells either On- or Off-Dox. In an analogous negative selection assay, two shRNAs targeting essential genes involved in DNA replication (proliferating cell nuclear antigen, PCNA; and an replication protein A3, Rpa3) led to a reduction in the percentage of infected cells upon Dox treatment, while in the absence of Dox no changes were observed (FIG. 3D). The control sh.Luci.1309 did not have any effect either On- or Off-Dox. These experiments demonstrated that the TRMPV vector can be used to generate reporter-target constructs for testing si-/shRNA knockdown efficiency.

5.2.2 TREtight Promoter

Slight leakiness of the TRE promoter was observed in one of the positive selection assays (FIG. 3C). Thus, TRE and TREtight (enhanced Tet-responsive element) promoters were compared side-by-side to analyze whether switching the promoter would reduce background activity Off-Dox while maintaining induction efficiency On-Dox. TREtight was previously described and shown to have tighter inducible response to Dox (Sipo et al. (2006), *J. Mol. Med.* 84, 215-225, the contents of which are hereby incorporated by reference).

The TREtight promoter was cloned into TRMPV, replacing the TRE promoter, yielding new vector TtRMPV. This new vector was compared to TRMPV in Rosa-rtTA MEFs. As seen by the growth advantage conferred by sh.p53.1224 (FIG. 4A), TREtight induced shRNA expression at least as potently as TRE in the presence of Dox. Furthermore, basal activity (Off-Dox) was negligible for both TRE and TREtight in this assay. No basal activity of TREtight was observed in this or other assays. Thus TtRMPV seemed to be a better vector than TRMPV for the reporter assay.

5.2.3 Reporter Cell Line Selection

Two commercially available rtTA expressing cell lines (U2OS-rtTA, HepG2-rtTA) were compared with the established Rosa-rtTA p53−/− MEFs. All three cell lines were infected with TRMPV viruses expressing sh.Luci.1309. Infection and induction efficiencies were monitored over several days (FIG. 4B). The results showed that U2OS-rtTA and HepG2-rtTA cells were infected less efficiently than Rosa-rtTA p53−/− MEFs. More importantly, the relative induction efficiency of shRNA expression was considerably higher in Rosa-rtTA p53−/− MEFs than in the two commercial cell lines. Hence, the Rosa-rtTA p53−/− MEF reporter cell line was selected for further reporter assays.

5.3 Example 3

Development of Cell Lines 5.3.1 RAg MEF Cell Line

Rosa-rtTA wild-type (wt) MEFs were isolated from Rosa-rtTA transgenic mice (Hochedlinger et al. (2005), Cell 121, 465-477, which is hereby incorporated by reference). Rosa-rtTA; p53$^{-/-}$ double-transgenic MEFs were isolated from embryos obtained after serial cross-breeding of Rosa-rtTA mice to p53$^{-/-}$ mice (Donehower et al. (1992), *Nature* 356, 215-221, which is hereby incorporated by reference). Rag MEFs were generated by immortalizing Rosa-rtTA MEFs with simian vacuolating virus 40 (SV40) large T antigen (LTAg), through lentiviral infection. Lentiviruses bearing a cytomegalovirus (CMV) promoter driven LTAg cDNA were used. Advantages of MEFs and suitable cell culture techniques have been described previously (McCurrach and Lowe (2001), *Method. Cell Biol.* 66, 197-227, which is hereby incorporated by reference).

5.3.2 ERC Cell Line

The ERC cell line is an rtTA3 (Puro) and EcoR (Hygro) expressing clone of spontaneously immortalized DF-1 chicken embryonic fibroblasts used as a sensitive tet-On reporter cell line that is inert to mammalian shRNAs. The cells are homogeneously infectable with ecotropically packaged retroviruses, and enable single-copy genomic integration of transgenes (e.g., tet-regulatable shRNAs) and nearly complete (>90%) induction of TRE promoters upon doxycycline treatment. DF-1 chicken embryonic fibroblasts (Himly et al. (1998), *Virol.* 248, 295-304; incorporated herein by reference) were co-infected with two VSV-G pseudotyped retroviruses, MSCV-rtTA3-PGK-Puro and MSCV-EcoReceptor-PGK-Hygro. After double selection (Puro/Hygro) and bulk analysis of rtTA3 function, 25 clones were isolated and individually tested for: (i) growth characteristics, (ii) stable and homogenous morphology, (iii) stability in confluent states, (iv) viability after freeze/thaw cycles, (v) ecotropic infectability, (vi) rtTA3 function, (vii) insensitivity to mammalian shRNAs and (viii) miR-30 processing. The ERC cell line was derived from the clone that performed best in these tests.

DF-1 cells (U.S. Pat. No. 5,672,485), a spontaneously immortalized CEF (*Gallus gallus*) cell line, were co-infected with vesicular stomatits virus glycoprotein (VSV-G) pseudotyped retroviruses; MSCV-rtTA3-PGK-Puromycin and MSCV-EcoRec-PGK-Hygro. After double selection with puromycin and hygromycin B, rtTA3 and EcoR function were tested by TRMPV infection and subsequent quantification of shRNA expression on a flow cytometer. Since the bulk population showed the expected infectability and induction of the TRE promoter upon Dox treatment, cells were sparsely plated in presence of the two selection markers and 25 single clones picked. Isolated clones were then individually tested and the final cell line, termed "ERC," was derived from the clone that performed best in these tests.

As primary characterization a doxycycline titration was run with the polyclonal DF1 ER3 cell line (DF-1 cells infected with rtTA3 and EcoReceptor) in order to test the functionality of the tet system and to assess whether miR-30 based shRNAs are processed (FIG. 4C). DF1 ER3 and RAg MEFs were infected at ~50% with TtNmPV sh&t Luci.1309 (excellent shRNA), sh&t PTEN.1523 (excellent shRNA), sh&t PTEN.1524 (intermediate shRNA) and sh&t C/EBPa.577 (weak shRNA) produced in ecotropic Phoenix (HEK 293T). Subsequently, the cells were treated for 4 days with different doxycycline concentrations. The results showed that the tet-On system was functional in the new DF1 ER3 cell line and that the rtTA3 reverse tet-transactivator induced the TRE promoter already at very low doxycycline concentrations (0.01 µg/ml), with full expression starting at 0.1 µg/ml doxycycline.

The effect of a lethal mouse Rpa3 shRNA in RAg MEFs and DF1 ER3 cells was assessed side-by-side. RAg MEFs expressing sh.Rpa3 died, while DF1 ER3 cells were insensitive to this shRNA. Hence, clones were picked to establish a monoclonal reporter cell line. Sparsely plated DF1 ER3s were grown in double selection (Puro/Hygro), and 25 clones were isolated and individually tested for (i) growth characteristics, (ii) stable and homogenous morphology, (iii) stability in confluent states, (iv) viability after freeze/thaw cycles and (v) trypsinization properties. In the 6 clones that passed these tests, rtTA3 function was assessed by TRMPVIN sh.Rpa3 infection, +/−Dox treatment, and analysis of TRE induction by flow cytometry. Five clones successfully induced shRNA expression On-Dox in >90% (90-95%), while leaky induction Off-Dox was nearly absent (0-1%). Clone DF1 ER3 C32 did not induce shRNA expression. All clones were comparably and easily infectable (30-50% at a 1:10 viral dilution rate).

In the two best performing clones, DF1 ER3 C8 and DF1 ER3 C18, neomycin (Neo) selectivity was analyzed for 500 µg/ml and 800 µg/ml Neo. Appropriately infected cells (e.g., TtNmPV, TRMPVIN) were successfully selectable, without bias for weak shRNAs over potent shRNAs, when using the retroviral vector TtNmPV. To assess whether these two clones are insensitive to mammalian shRNAs, RAg MEFs, DF1 ER3 C8, and DF1 ER3 C18 were infected at low MOI with TRMPVIN expressing a previously characterized shRNA against Rpa3, known to have a lethal effect in mouse cells. Infected cells (~15%) were selected on Neo (800 µg/ml) for six days to enrich to 60-85% infected cells. The competition assay was run for 16 days (DF1 ER3 clones: 1000 ng/ml Dox; RAg MEFs: 2000 ng/ml Dox) and proved that both DF1 ER3 clones were resistant to the lethal mouse shRNA.

In order to assess miR-30 processing, we characterized the green-shift and its correlation to Western blot readouts for four established shRNAs covering a wide range of knockdown potencies. DF1 ER3 C8, DF1 ER3 C18, and RAg MEFs were compared side-by-side by infecting the cells with TtNmPV sh.Luci.1309 (excellent shRNA), sh.PTEN.1523 (excellent shRNA), sh.PTEN.1524 (intermediate shRNA) or shC/EBPa.577 (weak shRNA). Subsequently, the cells were treated at different doxycycline concentrations (DF1 ER3 clones: 0.0 µg/ml in duplicates, 0.1 µg/ml, 0.5 µg/ml or 1.0 µg/ml; RAg MEFs: 0.0 µg/ml in duplicates or 2.0 µg/ml in duplicates) for 4 and 7 days (FIG. 8).

The results showed that both chicken clones correctly and accurately predict shRNA potency, which implies that miR-30 based shRNAs are processed in these chicken cell lines in an at least very similar way as in mouse or human cells. The results further showed that the dynamic range of Venus expression and suppression is much wider in the new chicken cell lines as compared to the RAg MEFs. The highest Venus fluorescence intensities are higher than in RAg MEFs, probably due to the fact that the cells are smaller in size. Thus, the produced amount of protein is more concentrated, resulting in a higher intensity on the flow cytometer. More importantly, Venus suppression mediated by the most potent shRNAs leads to much lower Venus fluorescence in the monoclonal chicken cell lines, as compared to the polyclonal RAg MEFs, which could be due to the tet-On system working more consistently and increased performance due to rtTA3. Additionally, the peaks of fluorescence emission are generally sharper in the chicken clones, meaning that there is less variability in fluorescence intensity. This is most likely a consequence of the eliminated retroviral insertion site variability and leads to dramatically increased FACS precision. The DF1 ER3 C18 clone was chosen for further experiments and termed "ERC."

ERCs were co-infected at varying dilution rates (1:1, 1:2.5, 1:5, 1:10, 1:20, 1:40, 1:80, 1:160, 1:320) with MSCV-Red2 and MSCV-GFP constitutively expressing either a red or a green marker. Two days after infection, fluorescence was quantified on a flow cytometer (FIG. 9). To compare the mathematical model described in Section 4, supra, with the experimental data, the theoretical ratio of multiple integrations $P(n>1)$, plotted as a function of the infection rate $P(n>0)$, was compared to the ratio of Red and Green fluorescent ERCs, plotted as a function of the viral dilution rate/MOI. The experimental curve lied underneath the theoretical curve, since cells infected exclusively by multiple MSCV-Red2 or multiple MSCV-GFP viruses are not found in the double-positive population. More importantly, the fact that the two curves shared a common start and endpoint demonstrates that from a given ERC population, ~100% of the cells could theoretically be infected at any time, thereby excluding the possibility of subpopulations with distinct infection characteristics. The initially increasing and then decreasing distance of the experimental curve from the theoretical curve (in both endpoints the curves joined) can be explained by the factors of the polynomial terms and the variable probabilities of higher order multiple integrations.

Taken together, these results show that the ERCs constitute a homogeneous population of cells that can be infected up to 100% with MSCV-based retroviruses. Significantly, the uniform infection efficiency permits using a statistical model allowing the prediction of genomic integration number per cell, based on the MOI. This ultimately allows infection of a target population at (zero or) single-copy genomic integration necessary for large-scale screens.

5.4 Example 4

The Sensor Approach 5.4.1 Knockdown of Venus Expression

TtRMPV was able to effectively and conditionally express shRNAs in the Rosa-rtTA expressing MEFs (FIG. 4A). Thus, it was hypothesized that cloning the cognate target sequence of a given shRNA (or siRNA) into the 3' UTR of a reporter gene (such as Venus) might lead to knockdown of reporter gene expression upon shRNA induction, and reporter gene expression levels would be inversely correlated to shRNA knockdown efficacy.

The following experiments confirmed this hypothesis. In these experiments, the cognate and control target sensor sequences were cloned into the Venus 3' UTR of the TRMPV (and TtRMPV) vectors expressing two potent shRNAs, sh.p53.1224 and sh.Luci.1309. Each target sensor was composed of a 52 nt target sequence. Specifically, this target sequence was composed of the 22 nt target mRNA complementary to the shRNA guide strand, plus the 15 nt flanking sequences up- and downstream on the target mRNA. A length of 15 nucleotides was selected as a compromise between mimicking local secondary structures of target mRNAs and keeping the target sensor as short as possible to allow for easy oligonucleotide cloning.

Following cloning, plasmids were transfected into Phoenix packaging cells and the transfection efficiency was analyzed by epifluorescence microscopy. As expected, cells transfected with control plasmids (i.e., vectors carrying a control target sensor) showed bright green Venus fluorescence emission. However, cells transfected with plasmids encoding the cognate target sensor showed only faint Venus expression. When virus-containing supernatant of these cells were used to infect MEFs (target cells), infection efficiencies were drastically decreased.

This severe reduction in virus production was likely due to RNAi. In Phoenix cells three different transcripts were synthesized: the PGK-driven Venus transcript, the TRE transcript generated because of accumulating leaky TRE activity, and the viral LTR transcript. The latter two transcripts efficiently expressed the shRNA. Meanwhile, all three transcripts harbored the target sensor at its end. Potent shRNAs led to degradation of all three transcripts by RNAi which, in the case of the LTR transcript, led to reduced retrovirus production.

5.4.2 Establishment of Effective Retroviral Packaging

In order to establish retroviral packaging that was equally effective for both functional and dysfunctional shRNAs, shRNA processing was interfered with by depleting components of the miRNA machinery active upstream of the merge of the miRNA and siRNA pathways in the cells. Since DGCR8, an essential cofactor of Drosha, is one such component, three different siRNAs were designed against DGCR8 and tested for their effects on retroviral packaging by co-transfecting them with the various TRMPV vectors. The harvested viruses were then used to infect Rosa-rtTA p53$^{-/-}$ MEFs (FIG. 5).

As monitored by the infection efficiency of Rosa-rtTA p53$^{-/-}$ MEFs, co-transfection of one of the three siRNAs against DGCR8 led to nearly complete re-establishment of viral packaging. Thus, the use of DGCR8 siRNA allowed for the production of retroviruses that were equally infective regardless of the shRNA and target sensor sequences on the vector. Thus, in embodiments involving the use of retrovirus-based vectors, packaging cell lines can be modified such that DGCR8 is knocked-out, whether by siRNA, shRNA, or by gene-targeting for example.

5.4.3 Confirmation of Coupled RNAi Molecule and Target Sensor on a Single Vector-Evaluation of Knockdown Efficiency The ability of potent shRNAs to knock down Venus expression where the shRNA and its cognate target are on the same vector was tested. Rosa-rtTA p53$^{-/-}$ MEFs were infected with TRMPV vectors carrying shRNAs known to be effective and their cognate target sensors (e.g., sh.p53.1224.t.p53.1224, sh.Luci.1309.t.Luci.1309). The infected cells were treated with Dox at six different concentrations. While a control target sensor did not have any effect (data not shown), the presence of a cognate target sensor led to Dox-induced, dose-dependent knockdown of Venus expression (FIG. 6). These data confirm that the basic vector design of the Sensor Approach works, where the basic design of the vector comprises coupling in the same vector an RNAi molecule to its cognate target sensor that is located in the 3'UTR of a reporter gene. In all of the following experiments, Dox was used at a concentration of 1 μg/ml.

5.4.4 Confirmation that the Sensor Approach can Provide Discrimination of Strong, Intermediate, and Weak RNAi Molecule Efficacy—Detection of Intermediate and Weak shRNA Knockdown Activity It was next examined whether an shRNA with varying potencies would be so predicted by the target sensor system or Sensor approach. Several pairs of shRNAs (five for C/EBPα (CCAAT/Enhancer Binding Protein α) and three for Arf) and their corresponding target sensors were cloned into TRMPV. The resultant viral vectors' ability to knock down Venus expression in Rosa-rtTA p53$^{-/-}$ MEFs was then assayed (see, e.g., FIG. 7). Based on Western blot analysis, shRNAs were categorized as "excellent," "good," "medium," and "weak."

Concomitantly, the knockdown efficiency of each C/EBPα shRNA was ranked in Western blots. For this assay, the shRNAs were cloned into MLP, amphotropic viruses produced, and NIH3T3 cells stably over-expressing the C/EBPα cDNA were infected. Total protein was obtained after three days of puromycin selection. The data showed that the shRNA ranking predicted by the target sensor reporter assay corresponded to the ranking deduced from Western blot analyses. Hence, Venus expression levels were inversely correlated to shRNA knockdown efficacy, and thus can serve as a quantitative readout for shRNA potency.

5.4.5 Effect of a Cognate Target Sensor on the Endogenous Function of shRNAs

Before starting to construct a larger set of shRNA-target sensor constructs, it was evaluated whether cognate target sensors would affect the function of the shRNAs on endogenous genes in the host cells. To do so, a colony formation assay and Western analysis was performed to quantify the effect. For the colony formation assay, Rosa-rtTA MEFs were infected at low MOI with TtNmPV (a slightly modified version of TtRMPV carrying a neomycin selection marker; see below), selected with neomycin (Neo), sparsely plated, and then treated with or without Dox. The same cells were selected on Neo to obtain total protein for Western analysis. The results of the colony formation assay showed that p53 shRNA expression strongly increased colony formation in the absence of a cognate target sensor (data not shown). By contrast, in the presence of a cognate target sensor, this effect was nearly abolished and only a minimal number of small colonies resulted from p53 shRNA expression. The results of the Western blot also showed that the presence of a cognate target sensor severely compromised p53 knockdown (data not shown). The slight knockdown observed in the sh.p53.1224.t.Luci.1309 Off-Dox sample could be explained by insufficient Off-Dox treatment after Neo selection (On-Dox) or by enrichment of leaky TRE promoters during the long selection period (32 days).

In addition, the consequences of a target sensor on the endogenous function of lethal shRNAs was also tested in a negative selection assay. RAg MEFs (Rosa-rtTA SV40 large T antigen MEFs) were infected with TtNmPV constructs carrying lethal (sh.PCNA.538) or neutral (sh.Luci.1309) shRNAs either in presence or absence of their cognate target sensor. The ~70% infected cells were subsequently treated with and without doxycycline and growth characteristics monitored over time. Similar to the previous assays, the presence of a cognate target sensor partially inhibited the endogenous function of lethal shRNAs. Taken together, these assays indicated that the co-expression of a cognate target sensor diminished the effect of shRNAs on endogenous targets without ever completely abolishing it.

5.4.6 Replacement of dsRed2 Spacer with Neomycin

Slight fluorescence emission was observed from dsRed2 in the green filter of the flow cytometers used in the experiments described above. Thus, dsRed2 was replaced with a Neo coding sequence, which had previously been shown to drastically enhance shRNA expression in the context of miR-30 based viral vectors (Stegmeier et al. (2005), *PNAS* 102, 13212-13217, which is hereby incorporated by reference). This Neo-coding sequence was cloned into TtRMPV, leading to TtNmPV. The new TtNmPV vector was characterized for its infection and induction potential and was found to be similar in those potentials to TRMPV and TtRMPV. TtNmPV was therefore used in all subsequent experiments.

To confirm that the Neo spacer would allow for selection of infected cells, a neomycin selection assay was performed with infected Rosa-rtTA MEFs. These MEFs may not be an ideal setting to assess Neo selection since growth-conferring shRNAs inherently affect the selection procedure. But the experiment showed that infected cells could easily be enriched. Consequently, Neo selection or other growth-selection reporter genes are an alternative to fluorescent or other non-growth selection based reporter genes in pooled approaches for the enrichment of infected cells. The only caveat with this option is that Rosa-rtTA $p53^{-/-}$ MEFs already carry a neomycin resistance gene, which had been introduced to knockout p53.

To circumvent this problem, a new cell line was established by immortalizing Rosa-rtTA MEFs with lentiviruses carrying SV40 large T antigen expressed from a CMV promoter. This cell line was termed RAg MEFs. Microscopy analysis showed that at least part of the cells infected with Lenti-CMV-LTAg became immortalized and started to proliferate faster and faster, while cells infected with a control viral vector entered senescence and eventually died. Immortalization was shown by the fact that after the first five to six passages, a confluent plate of RAg MEFs split 1:10 grew confluent again in two to three days. This process was repeated up to 30 passages. Further cell culture analysis showed that RAg MEFs were smaller ($8-10 \times 10^6$ cell/confluent 10 cm plate) and more homogenous than Rosa-rtTA $p53^{-/-}$ MEFs ($4-5 \times 10^6$ cell/confluent 10 cm plate). Additional experiments showed that RAg MEFs could be kept confluent up to 10 days without showing raised lethality (<3% dead cells) and that induction of shRNA expression was at least as efficient as in Rosa-rtTA $p53^{-/-}$ MEFs. In a Neo selection assay a population of 25% infected RAg MEFs (low MOI) increased to over 75% in 4 days and over 85% in 6 days. These data confirmed that RAg MEFs were a useful cell line for further reporter assays where Neo selection was used to select for viral infected cells.

5.4.7 Effect of Target Sensor Flanking Regions

It was evaluated whether the target sensor flanking regions affect si-/shRNA potency. In the design of the described reporter assay, the target sensor is composed of the 22 nucleotides of target mRNA directly complementary to the shRNA guide strand plus the flanking 15 nt sequence up- and downstream on the target mRNA.

Both a weak-to-intermediate and a potent shRNA against two different genes (Trp53, sh.1224 and sh.1647; PTEN, sh.1523 and sh.1524) were cloned into vectors that contained either the cognate target sensor or, in the case of the potent shRNA, a target sensor composed of the cognate core sensor (the 22 nt directly complementary to the shRNA guide strand) and the flanking regions from the weak shRNA's target sensor. Rosa-rtTA $p53^{-/-}$ MEFs were infected at low MOI. Two days after infection cells were split into triplicates and treated+/−doxycycline (1 μg/ml) for four days.

The results showed that the flanking regions had no or only a negligible impact on shRNA efficacy prediction.

5.5 Example 5

The High-Throughput Sensor Approach—Pooled Cloning of Tiled Libraries and Screens Thereof

5.5.1 Reporter Assay Prediction

A set of 20 shRNAs (referred to as a "MiniPool" below) and their cognate target sensors were cloned into TtNmPV together with one negative control. Since all preliminary difficulties with the reporter assay (the Sensor Approach in Example 4) had been resolved, each shRNA-target sensor construct of this set was then analyzed in the RAg MEF cell line. The aim of this single-construct experiment was to assess the capability of the reporter assay to correctly predict si-/shRNA efficacy one-by-one.

Hence, each TtNmPV shRNA-target sensor construct was tested in three independent replicates (FIG. 10). As mentioned supra, shRNAs were chosen according to western blot results in order to have about equal amounts of excellent, good, medium, and weak shRNAs. Results showed that the reporter assay predicted shRNA efficacy very accurately and consistently (three independent replicates) in nearly all cases. The data shows that the reporter assay predicts shRNA efficacy very reliably in single-construct approaches. Thus, the assay was next tested to determine whether it would also reliably forecast correct si-/shRNA potency ranking if a set of shRNA-target sensor constructs were pooled and jointly analyzed.

5.5.2 A Pooled Approach for Identifying Efficient si-/shRNAs

The Sensor approach shows an inherent link between phenotype (e.g., green vs. non-green cells) and genotype (potent vs. weak shRNA), which is achieved through the single-construct approach—coding sequences for an si-/shRNA and its cognate target sensor are cloned into the same vector. This inherent link due to coupling of the RNAi molecule and the reporter gene-target sensor allows using high-throughput flow cytometry to separate cells containing si-/shRNAs with varying potency.

The following experiment demonstrated that the Sensor approach accurately predicts the knockdown efficiency of individual si-/shRNAs when a set of si-/shRNA-target sensor constructs are pooled and jointly analyzed. In this experiment, the coding sequences for the 20 shRNAs (the MiniPool) and their respective cognate target sensors, along with one negative control, were cloned into TtNmPV and transfected into packaging cells (Phoenix HEK293T). Then viruses so produced were used to infect RAg MEFs at low MOI.

To increase the percentage of infected cells in the population (from about 25% to more than 90%), cells were either pre-sorted by FACS for green fluorescence or Neo-selected for 8 days (see FIG. 2 for scheme). Subsequently, cells were treated with or without Dox for six days and then separated by FACS. For both the On- and Off-Dox samples, three fractions were sorted: 20% lowest GFP expression, 20% medium GFP expression (as assessed on a logarithmic scale of GFP intensity), and 20% highest GFP expression. Genomic DNA was isolated from each fraction, and target sensors were PCR amplified.

Amplified PCR fragments were then directly cloned into TOPO TA vectors (Invitrogen) and transformed into Top10 *E. coli* cells. For each pre-sorted fraction, 288 colonies were picked and the constructs contained in them were sequenced.

For each Neo-selected fraction (only On-Dox), 192 colonies were picked and the constructs contained in them were sequenced. The distribution of the different shRNA-target sensor constructs was analyzed in each fraction (FIG. 11).

The results showed that the reporter assay could correctly rank shRNA in order of knockdown efficiency when analyzed in a pooled fashion. 89.8% of sequenced sequences were unambiguously identifiable without bias for any given fraction. Furthermore, an approximately equal representation of each shRNA was observed both On- and Off-Dox. This means that no shift in representation took place due to the expression of shRNAs On-Dox, thereby excluding lethal or growth promoting influences of specific shRNAs. This notion was also confirmed by a correlation analysis that yielded a square Pearson correlation coefficient $R^2=0.603$ for a linear regression with intercept at 0, indicating a high correlation between the two datasets.

In an analogous data evaluation, it was probed whether excellent shRNAs were lost during Neo selection due to shRNA-mediated knockdown of the Neo resistance gene. The data indicated that this was not the case. Besides these global analyses, the number of sequence reads for each shRNA-target sensor construct in a given fraction produced highly significant results. For example, when comparing the two shRNAs PTEN.1523 and PTEN.1524, it was deduced that PTEN.1523 was an excellent shRNA because significantly more sequences were found in the low GFP fraction than in the medium or high GFP fraction (FIG. 12). On the other hand, PTEN.1524 was predicted to be an intermediate shRNA because only a few reads were detected in the low GFP fractions while many were found in the medium and high GFP fractions.

These results correlated with Western blot analyses and demonstrated that the reporter assay was very sensitive because PTEN.1523 and PTEN.1524 were shifted by only one base pair on the target mRNA (FIG. 12). This correlation between Western blot ranking and number of reads per fraction was consistent for the entire pool (FIG. 11).

In fact, the distribution of shRNAs in the Off-Dox population was homogeneous over all three fractions. By contrast, in the On-Dox population (where shRNAs were expressed) the distribution reflected the efficacy of each shRNA. Excellent shRNAs were primarily present in the low GFP fraction, due to knockdown of Venus in the reporter assay, and nearly absent from the high GFP fraction. Good and medium shRNAs were mainly present in the medium GFP fraction. Weak shRNAs were principally observed in the high GFP fraction. Hence, these studies showed that pooled analysis of shRNA efficacy and isolation of the most potent shRNAs using flow cytometry-based sorting strategies is possible for small sets of 20 shRNAs. The same analysis shown here for the pre-sorted samples was also carried out for the Neo-selected samples and led to the same results.

In order to have a single evaluation variable for future de novo shRNA efficacy predictions, a reporter assay based shRNA ranking system was established and tested (FIG. 13).

The value for the shRNA ranking was calculated for each shRNA as follows: A=(reads in low GFP fraction)×(1); B=(reads in medium GFP fraction)×(0); and C=(reads in high GFP fraction)×(−1).

Subsequently, a positional value was attributed to each shRNA: Positive value=(A+B+C)/(Total # of reads at low, medium, high).

The final ranking was calculated using the formula: Ranking=(Positive value On-Dox)−(Positive value Off-Dox).

When this system was applied to the dataset, the resulting shRNA ranking (FIG. 13) corresponded well with both the Western blot classification and with the direct data analysis (FIG. 11). This ranking system is a useful tool for fast analysis of larger sets of shRNAs.

5.5.3 Pooled Cloning of Large shRNA-Target Sensor Libraries

The term "shRNA-target sensor library" or "target sensor library" refers to a mix of equal vectors (for example, TtNmPV) each containing a unique si-/shRNA-target sensor construct. All desired si-/shRNA-target sensor constructs are cloned into the expression vector together (i.e., "pooled cloning"), in contrast to single cloning where each construct is cloned separately. Each shRNA and its cognate target sensor were synthesized on a single oligonucleotide via on-chip oligonucleotide synthesis techniques, which allowed for the production of oligonucleotides of up to 200 nucleotides. The strategy for pooled cloning of shRNAs is shown in FIG. 15.

A pool of approximately 20,000 shRNAs and their cognate target sensors was synthesized and cloned into TtNmPV. In this pool, all possible shRNAs were generated for a couple of chosen genes in a process termed "gene tiling." (See FIG. 14.) Initially each shRNA and its cognate target sensor were synthesized by on-chip synthesis as one oligonucleotide. This step guaranteed the essential coupling of an shRNA and its corresponding target sensor. Pools of approximately 20,000 shRNA-target sensor oligonucleotides were synthesized on each chip.

These pools were subsequently amplified by polymerase chain reaction (PCR) with primers that added endonuclease restriction sites. PCR products were then cloned into expression vectors in which the sequence between the beginning of the shRNA and the end of the target sensor had been cut out (cloning step I; FIG. 15). In a subsequent cloning step the missing part of the expression vector was inserted between the shRNA and the target sensor, thereby completing the vector. In the case of TtNmPV, in a first step the 3' miR30-PGK-Venus coding sequence was excised from the vector and replaced by a PCR-amplified, with restriction enzymes cut, oligonucleotide encoding a shRNA-target sensor construct from the shRNA-target sensor library. In the second step, this 3' miR30-PGK-Venus fragment was re-inserted into the product of cloning step I to reconstitute the complete TtNmPV vector, which now contained a member of an shRNA-target sensor library.

In order to retain every shRNA-target sensor construct of the initial pool throughout all the cloning and reporter assay steps, it was useful to guard a representation of 1000×. This means that in every step, at least $20\times10^6$ oligonucleotides, vectors or cells had to be present. Successful cloning and retention of the initial representation was shown by SOLEXA deep sequencing.

5.5.4 Evaluating, Identifying and Separating Potent shRNAs from Large Pools

After successfully cloning a large shRNA-target sensor library, the last step to the completion of the tiled-sensor reporter assay was to demonstrate the ability to extract potent shRNAs from large pools. In a process similar to that described above, RAg MEFs target cells were infected with viruses expressing the shRNA-target sensor library, treated with or without doxycycline, and sorted into fractions of cells showing different levels of fluorescent marker expression on a flow cytometer.

For FACS, two different strategies were employed. The first one, analogous to that described previously for the 20-member pool, was based on treating the target cells+/−doxycycline and then sorting both treated and untreated cells into four fractions. (See FIG. 16.) The distribution of reads for a given shRNA over the four fractions On-Dox was compared to its distribution Off-Dox.

Using the first sorting strategy the background noise of the library was too high to sort the cells and obtain any correct readouts. While it is relatively easy to sort pools of a small size (e.g., 20 shRNAs, as shown above), larger pools complicate the situation due to complexity associated problems (conspicuous background noise, miss synthesized shRNAs or target sensors, large percentage of non-functional shRNAs, retroviral insertion site variegation) and require more dynamic approaches with repetitive cycles of purification and enrichment, ultimately leading to the isolation of the most potent shRNAs.

The second sorting strategy entails directly assessing the green-shift of shRNA-target sensor constructs through sorting. In this strategy, all infected cells are first treated with doxycycline and then sorted for low GFP (Venus) expression. In a second step, the sorted cells are kept in culture without doxycycline and then sorted for high GFP expression. (See FIG. 17.) This strategy allows sorting potent, functional shRNAs, as non-functional shRNAs will not be able to shift and non-potent shRNAs are not found in the low GFP fraction On-Dox.

Using the second strategy, good results were obtained for the control shRNAs that were spotted with a 15× overrepresentation (FIG. 18); however, for the other shRNAs the sorting was not yet precise enough. Furthermore, it was observed that for essential genes (e.g., PCNA, Rpa3), potent shRNAs were lost. Hence, the neutral ERC cell line, described in Example 3, was used, as it is not affected by the mammalian shRNAs from the libraries screened here. The ERC cell line was used with an improved variant of the second sorting strategy (FIG. 19) and with a third-generation sorting strategy (FIG. 20).

This third-generation sorting strategy for large pools entails functionally assessing the shRNA-mediated green-shift in iterated cycles of suppression and derepression of marker protein (Venus) expression. In this approach, FACS gates are drawn based on a guide population of well-characterized, excellent shRNAs. A population of weak shRNAs serves as an additional control for exclusion gates. This sorting strategy is termed "Sensor Ping-Pong" (FIG. 20A).

In the Sensor Ping-Pong strategy cells infected On-Dox at low MOI (20-30%) are kept On-Dox for an additional 5-7 days and then sorted for low GFP expression. The low GFP gate is set to include >85% of the Top5 gating population (Top5=5 excellent reference shRNAs) and exclude most Bottom5 shRNAs (Bottom5=5 bad reference shRNAs). Subsequently, the sorted cells are kept Off-Dox for 6-7 days and then sorted for high GFP expression. The gate is again set to include >85% of the Top5 shRNAs. In step 3, the twice-sorted shRNAs are kept On-Dox for 6-7 days and then sorted for low GFP expression. This time the gating is set to include the lowest 50% of the Top5 shRNA population. To further select and purify the population of shRNAs (from the initial library), sorting steps 2 and 3 can be reiterated using the same Dox cycles and gating strategy. During all On-Dox cycles, cells can additionally be put on neomycin to prevent contamination and to further select for infected cells expressing shRNAs. While sorting steps 1 and 2 mainly serve to purify the population (i.e., eliminate non-functional shRNAs and bad integrants) and to reduce the apparent complexity to the actual complexity of the pool, the subsequent sorting steps gradually enrich potent shRNAs and deplete weak and intermediate ones.

5.5.5 Evaluating, Tiled shRNAs

As a proof-of-concept for the reporter assay, pooled cloning, and sorting strategy, and for the production of optimized shRNAs targeting virtually any gene, a tiled shRNA-target sensor library targeting a small set of genes was generated and the optimized shRNAs were validated by Western blot. This set included: i) Hras1 (Harvey rat sarcoma virus oncogene 1, *Mus musculus*); ii) Trp53 (Transformation related protein 53; *Mus musculus*); iii) Kras (v-Ki-ras2, Kirsten rat sarcoma viral oncogene homolog; *Mus musculus*); iv) Mcl1 (myeloid cell leukemia sequence; *Mus musculus*); v) PCNA (proliferating cell nuclear antigen; *Mus musculus*); vi) Rpa3 (replication protein A3; *Mus musculus*); vii) Bcl2 (B-cell leukemia/lymphoma 2; *Mus musculus*; only the common sequence of both murine Bcl2 transcript variants was used for the design of shRNAs); viii) Myc (myelocytomatosis oncogene; *Mus musculus*); ix) MYC (v-myc myelocytomatosis viral oncogene homolog; *Homo sapiens*). As intrinsic controls for the assay, 18 of the 20 shRNAs from the MiniPool (as described above) were included in the oligonucleotide synthesis. (The missing two shRNAs, sh.Trp53.1224 and sh.Rpa3, are included as part of the tiling of the respective genes.)

The tiled shRNA-target sensor library containing ~20,000 shRNAs was cloned as described previously. To prove that the theoretical complexity was retained throughout all cloning steps, the library was analyzed by deep-sequencing (FIG. 20F). Subsequently, ERC reporter cells were infected at low MOI with retroviruses expressing the described shRNA-target sensor library and subjected to the Sensor Ping-Pong sorting strategy described above. In total, five sorts were carried out and genomic DNA extracted from cells collected before and after every sort. As a final readout, the shRNA guide strands were PCR-amplified from the genomic DNA and identified and quantified by deep-sequencing (SOLEXA).

Figure 20B:
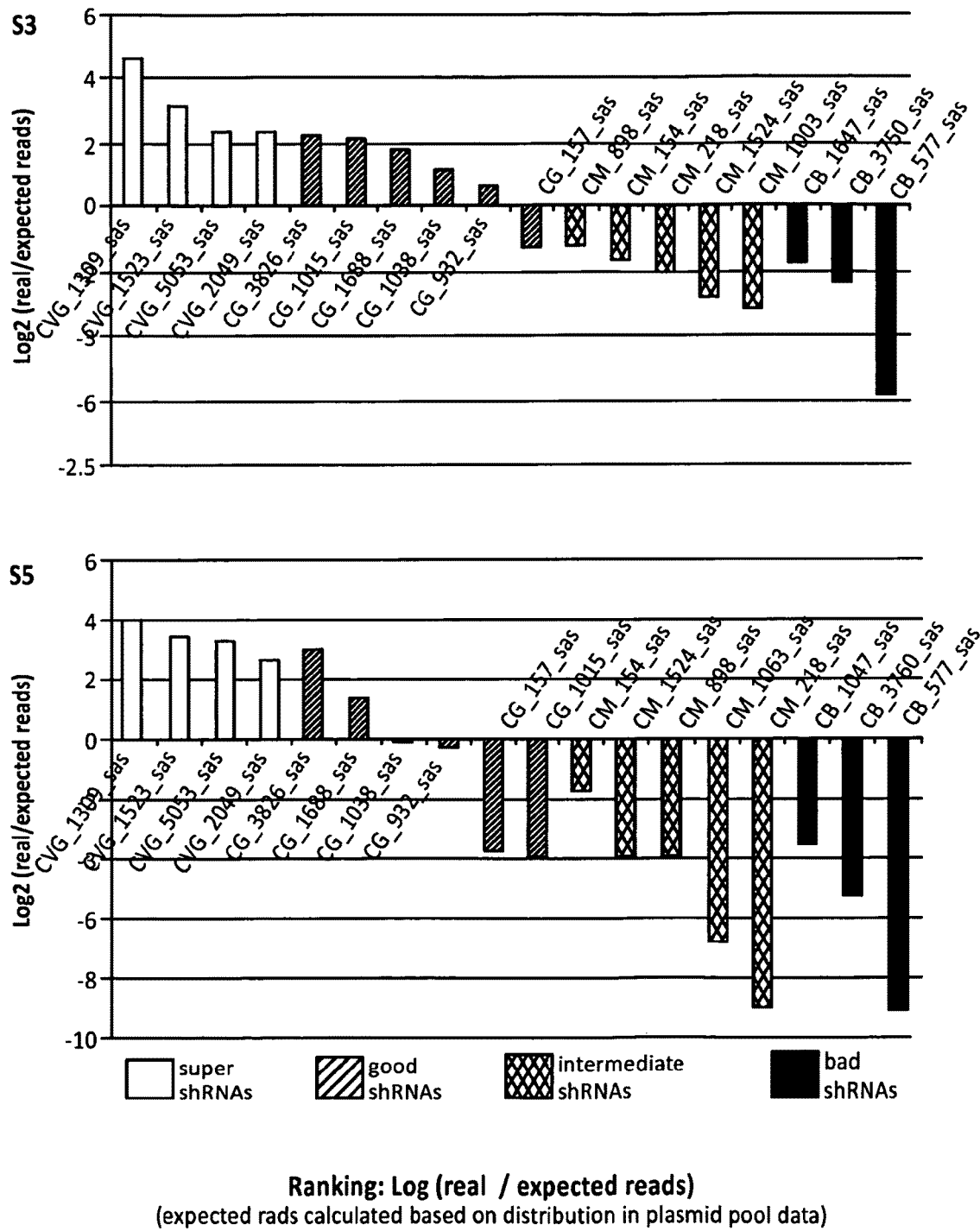
Figure 20C:
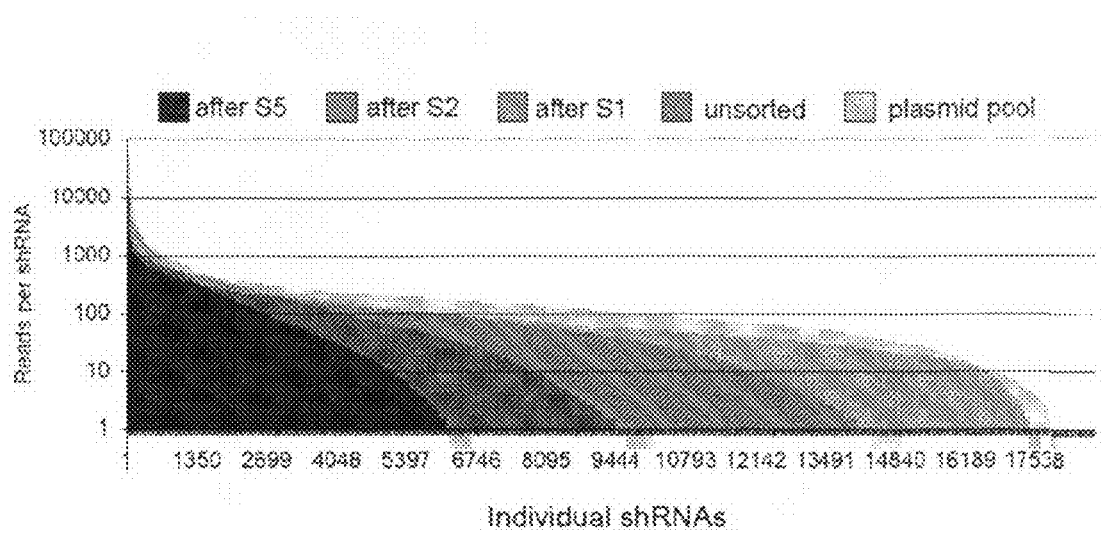

Whether the control shRNAs that were spotted on the chip (in addition to the tiled shRNAs) were predicted correctly was analyzed as a first validation of the reporter assay (FIG. 20B). As the graph shows (FIG. 20B), the potencies predicted by the Sensor assay correlated very well with the potencies previously measured by Western blot analysis. Encouragingly, the differences between potent and non-functional shRNAs became more prominent with increasing sorting cycles. However, since these controls were all spotted in 15× overrepresentation, it was questionable whether 1× spotted shRNAs were also correctly predicted. A close look at the "1224" region encompassing the well-characterized, excellent shRNA p53.1224 revealed that after 5 Sensor Ping-Pong sorts, sh.p53.1224 was strongly enriched, while all the surrounding shRNAs were generally depleted. This provides robust proof that the reporter assay is able to precisely pinpoint the most potent shRNAs by selectively enriching them.

To analyze the general effect of Sensor Ping-Pong sorting on the shRNA-target sensor library, shRNA pool complexity was monitored over time (FIG. 20C). Pool complexity decreased with increasing numbers of sorts as a consequence of shRNA depletion to a null value. At the same time an increase in representational variability was observed, showing that specific shRNAs enrich, while the majority deplete over the course of the sorts. If this observation is correct, then the correlation between initial and endpoint representation should also decrease with increasing sorts.

Figure 20D:
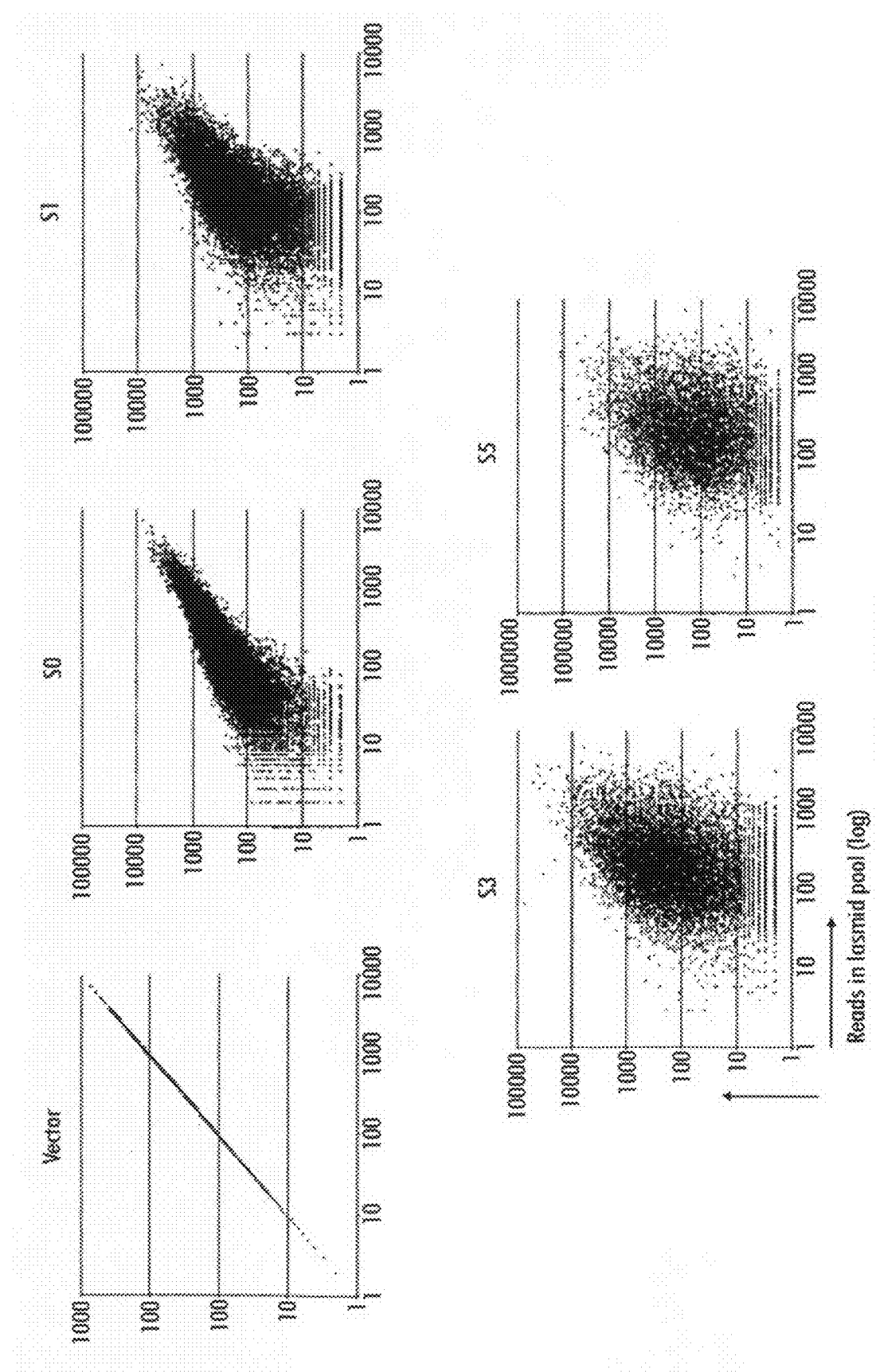
Figure 20E:
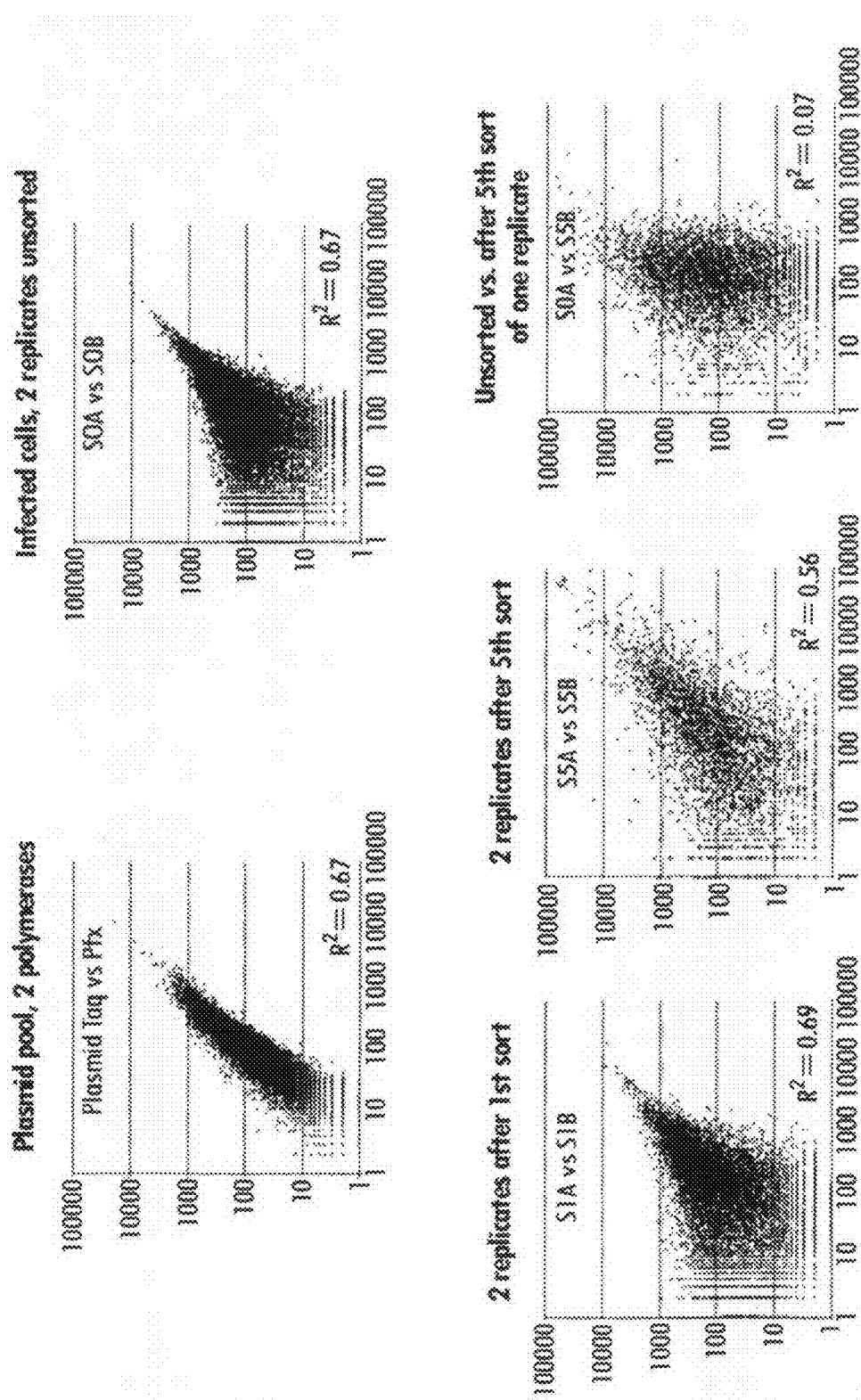
Figure 20F:
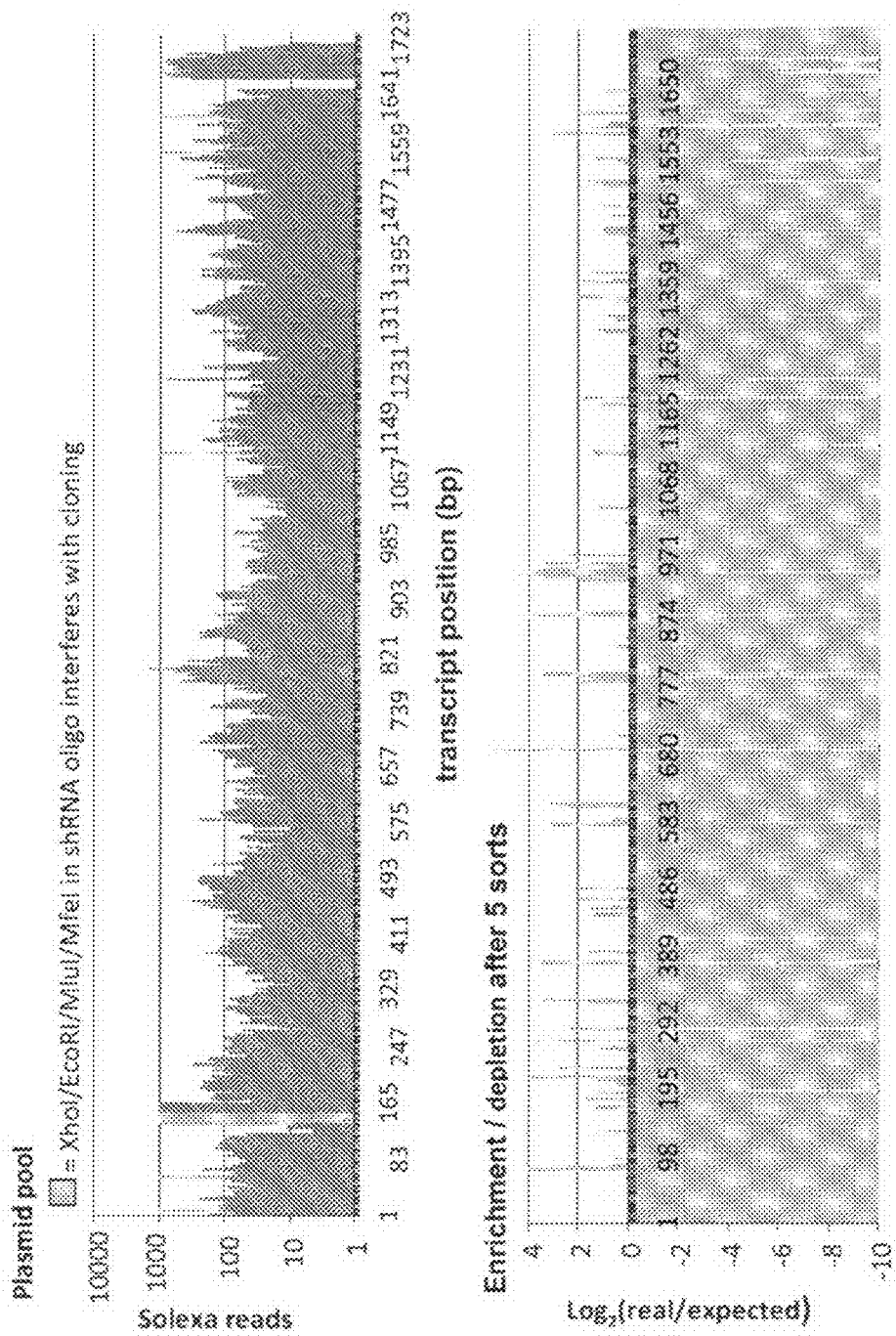
Figure 20G:
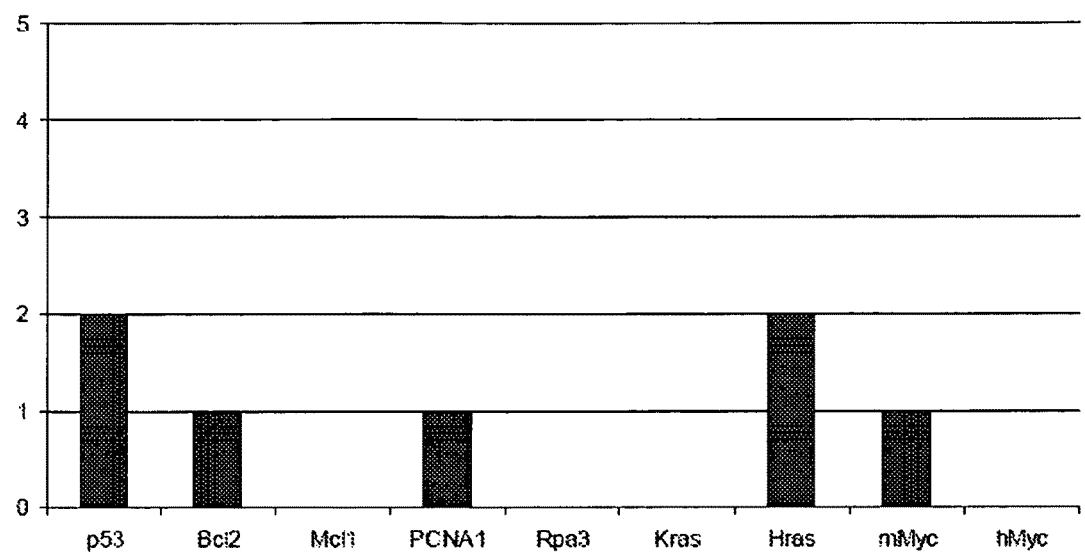

In fact, this decrease was observed in correlation between initial and endpoint representation (FIG. 20D). To make sure that decreasing correlation was not just a cell culture or sort induced artefact due to statistical variability or lack of representation of single shRNA, the correlation in representation between two biological replicates over the course of the sorts was investigated (FIG. 20E). The biological replicates showed only minimal variability, in large contrast to the net change in representation between initial (shRNA-target sensor library plasmid pool) and endpoint (shRNA pool in cells after 5$^{th}$ sort) representation. Thus, these results demonstrate that it is possible to specifically and reproducibly enrich given shRNAs while depleting other ones from large shRNA pools (~20,000 shRNAs) using the Sensor assay.

In order to find the best shRNA targeting a given transcript, it is crucial that the tiled shRNA library that is subjected to the Sensor assay completely covers the entire transcript. Hence, transcript coverage for all tiled genes was investigated. (See, e.g., FIG. 20F.) While transcript coverage before sorting gives insight as to how well the initial shRNA-target sensor library was generated (oligonucleotide synthesis, pooled cloning), transcript coverage after sorting reveals the characteristics of overall distribution of enriched or depleted shRNAs.

One would not expect to be able to clone absolutely all shRNA-target sensor constructs, since some of them contain restriction sites for the endonucleases used for cloning (XhoI, EcoRI, MluI, MfeI) and others might not have been synthesized in the first place. Constructs with used restriction sites represent 1 to 2% of the whole shRNA population. Surprisingly, nearly all (18,703/18,972) shRNAs targeting the 9 tiled transcripts were generated, including some containing restriction sites (FIG. 20F). In fact, about one third of such constructs were unexpectedly cloned using the mentioned restriction enzymes, even though the digestions were very successful (the system inherently selects for non-cut internal restriction sites). Only in rare cases were small "holes" in the transcript coverage observed, probably due to spots of poor synthesis during on-chip oligonucleotide generation.

To investigate whether top-scoring shRNAs from the Sensor assay are predicted by existing algorithms, the number of the top 5 shRNAs from the present reporter assay (per selected gene) were counted in the predicted top 10 lists of either BIOPREDsi (Huesken et al. (2005), *Nat. Biotech.* 23, 995-1001) or DSIR (Vert et al. (2006), *BMC Bioinformatics* 7, 520), two commonly used prediction algorithms (FIG. 20G). Remarkably, only a minority of the top scoring shRNAs from the reporter assay of the invention were predicted by the existing algorithms. Hence, these data underline the novelty and innovation of this approach in generating shRNAs that potentially knockdown target protein expression much more potently than shRNAs generated using existing tools.

To demonstrate that the Sensor assay not only predicts novel shRNAs, but that they are also optimized in regard to knockdown potential, selected shRNAs having variable scores in the Sensor assay (excellent, intermediate, weak) were validated side-by-side with the highest scoring predictions from existing algorithms (FIGS. 21 and 22).

As demonstrated in FIGS. 21 and 22, the reporter assay correctly predicts shRNA potency. All shRNAs highly scoring in the Sensor assay also showed potent target knockdown in Western blots. On the other hand, all non-scoring shRNAs from the Sensor assay knocked down target protein expression minimally or not at all. For p53 the shRNA "1224" obtained by far the most reads in the final deep-sequencing round. However, since "1224" also showed greater-than-average reads in the initial pool, its ranking/enrichment was not yet the highest. This caveat can be addressed by further Sensor Ping-Pong sorting cycles and/or an alternative ranking system that takes into account a steady increase of sequence reads number over the sorting time course.

Taken together, the data confirms that the RNAi Sensor reporter assay combined with the Sensor Ping-Pong sorting strategy allow isolation of potent shRNAs from large bulk population of non-functional or missynthesized shRNAs. If further combined with the pooled cloning strategies for the production of tiled shRNA libraries, the technology enables the design and generation of the most potent shRNAs targeting virtually any transcript. Last but not least, the increased knockdown potential of optimized shRNAs created by the here proposed methods and technology (as compared to existing technology) has been demonstrated and validated by Western blot analysis and thus constitutes a solid proof of the invention.

5.6 Example 6

Additional Experimental Methods 5.6.1 Cell Culture

NIH3T3 cells were grown in Dulbecco's Modified Eagle Medium (DMEM) supplemented with 10% bovine calf serum (CS) and 100 units/ml penicillin-streptomycin at 37° C. with 5% $CO_2$. Primary and immortalized mouse embryonic fibroblasts (MEFs), Phoenix-Ampho and Phoenix-Eco HEK293T cells, U2OS-rtTA (Clontech), and HepG2-rtTA (Clontech) were grown in DMEM supplemented with 10% fetal bovine serum (FBS) and 100 units/ml penicillin-streptomycin at 37° C. with 5% CO2. HepG2-rtTA cells were passed through a 25 G needle before plating. Immortalized chicken embryonic fibroblasts (DF-1s, DF1 ER3s, ERCs) were grown in DMEM supplemented with 10% fetal bovine serum (FBS), 1 mM sodium pyruvate, and 100 units/ml penicillin-streptomycin at 37° C. with 5% CO2.

5.6.2 Development of Plasmids, shRNAs, and Target Sensors

MLP (previously referred to as LMP) was a mouse stem cell virus (MSCV) based retrovirus (Clontech) that expressed miR-30-embedded shRNAs from the retroviral LTR and harbored a PGK-Puromycin-IRES-GFP cassette (Dickins et al. (2005), *Nat. Genet.* 37, 1289-1295; which is hereby incorporated by reference).

MSCV-based MGPP (5'LTR-psi-GFP-miR-30-(loxP)—PGK-Puro-(loxP)-3'LTR) expressed GFP and miR-30-shRNAs from the retroviral LTR and contained a PGK-Puromycin cassette.

TGM was a self-inactivating retrovirus that was based on the pQCXIX retroviral backbone (Clontech) and expressed a GFP-miR-30-shRNA fusion transcript under the control of a tetracycline responsive element (TRE).

pQCXIX-based TRMPV contained a TRE-driven dsRed2-miR-30 cassette followed by a PGK promoter driving expression of the green fluorescent marker Venus (Nagai et al. (2002), *Nat. Biotechnol.* 20, 87-90; which is hereby incorporated by reference).

TtRMPV was cloned by inserting a XhoI/NheI restriction fragment excised from TRMPV into the TtRM vector, which had a vector structure analogous to that of TRMPV, containing TREtight instead of TRE). The XhoI/NheI restriction fragment comprised the shRNA, the 5' miR-30 cassette, and the PGK-Venus construct.

TtNmPV was produced by replacing dsRed2 in TtRMPV with the Neomycin (Neo) spacer from pPRIME-CMV-Neo (Stegmeier et al. (2005), *Proc. Natl. Acad. Sci. USA* 102, 13212-13217; which is hereby incorporated by reference).

The pPRIME-CMV-Neo and TtRMPV vectors were digested with SbfI/XhoI. After ligation, the resulting vector was digested with BamHI/SbfI, Klenow treated, and blunt ligated. It was observed that the miR-30 context of pPRIME- CMV-Neo plasmid had a single base pair mutation. In order to obtain TtNmPV vectors with the longer and non-mutated miR-30 construct, an extra cloning step with NotI/XhoI was performed, excising the miR-30 from a TRMPV vector and ligating it into TtNmPV. Both 5' miR-30s were tested and no difference in shRNA expression efficiency was observed.

In some experiments, shRNAs were obtained from previously prepared plasmids by excising 110 bp XhoI/EcoRI restriction fragments and cloning them into the target vector. A set of 20 pre-existing, characterized shRNAs was chosen to create a set containing approximately equal numbers of shRNAs characterized as excellent, good, medium, or weak as determined by Western blot analysis.

Target sensors were cloned by annealing complementary oligonucleotides to form dsDNA. These linkers were then ligated into MluI/BsiWI digested recipient vectors (TRMPV, TtRMPV, and TtNmPV). All oligonucleotides had the following structure: 5' MluI—52 bp shRNA target sequence—AvrII—primer binding site—MfeI—BsiWI 3'.

Target sequences comprised the 22 nucleotide sequence complementary to the cognate shRNA guide strand plus 15 additional nucleotides up- and down-stream of the target mRNA. The restriction sites MluI and BsiWI were only partially coded on the oligonucleotides in order to create sticky ends. Pasha siRNAs (targeting DGCR8, the human orthologue of Pasha) were custom-designed, prepared, and applied according to the manufacturer's recommendations (Qiagen).

5.6.3 Transfection, Virus Production, and Infection

Transfections of Phoenix cells, retrovirus production, and infection of target cells was carried out as described (McCurrach and Lowe (2001), *Method. Cell Biol.* 66, 197-227; which is hereby incorporated by reference). Phoenix cells were plated 6-8 h prior to calcium phosphate transfection; 16 µg plasmid DNA and 6.5 µg helper plasmid or 15 µg plasmid DNA, 5 µg helper plasmid, and 5 µg siRNA (when targeting DGCR8 or other RNAi genes in the packaging cell) were co-transfected. Chloroquine was used to enhance efficiency. Virus was collected six times during the 36-72 h following transfection. Target cells were plated 6-8 h prior to infection (for MEFs, $1 \times 10^6$ cells/10 cm plate; for ERCs, $2 \times 10^6$ cells/10 cm plate). Where a specific infection rate was desired, test infections were carried out with different dilution rates, power functions fitted to the data, and ideal infection ratios deduced.

Rates of infection were quantified by assessing the percentage of green-fluorescent cells by flow cytometry (GUAVA EASYCYTE, Guava Technologies). According to the virus titrations, infections were carried out at dilutions rates ranging from 2 to 8. Infective units (IU)/ml viral supernatant were calculated to be $6-7 \times 10^4$.

In green-shift and competition assays, fluorescence intensities of infected cells were quantified by flow cytometry, either on a GUAVA EASYCYTE (Guava Technologies), an LSRII flow cytometer (BD Biosciences), or a FACS ARIA (BD Biosciences); the latter two were also used for FACS. Colony formation was determined by crystal violet staining.

5.6.4 Drugs

In the doxycycline (Dox) titration experiment, six different Dox concentrations were tested for MEFs: 0.00 µg/ml, 0.01 µg/ml, 0.02 µg/ml, 0.10 µg/ml, 0.20 µg/ml, and 1.00 µg/ml. In all other experiments Dox was used at 1.0 µg/ml, or at 1.0 µg/ml and 0.2 µg/ml. For CEFs, including ERCs, the Dox titration was repeated with 0.00 µg/ml, 0.10 µg/ml, 0.50 µg/ml, 1.00 µg/ml, and 2.00 µg/ml. In all other experiments, Dox was used at 0.5 µg/ml for ERCs. Neomycin (G418; InvivoGen) was used at 500 or 800 µg/ml for selection; puromycin (Sigma-Aldrich) at 2.5 µg/ml, and hygromycin B (Roche) at 100, 200 or 400 µg/ml. Ampicillin was used at 100 µg/ml in LB broth for bacterial cultures. Doxorubicin was used at 50 µg/ml to induce p53 expression 4-12 h prior to cell harvest for Western blots.

5.6.5 Western Blot Analysis

Cells were harvested, suspended in Laemmli buffer, and boiled. Protein concentrations were measured in Bradford assays and samples diluted to an equal concentration. For each sample 10-15 µg total protein was loaded and run on 10-15% SDS-PAGE gels. Expression of p19-Arf in shRNA infected p53$^{-/-}$ MEFs was analyzed using full protein and the rat anti-mouse p19-Arf (5-C3-1) primary antibody (Upstate, 1:500). Levels of p53 expression were determined in NIH3T3 using full protein and a mouse anti-mouse p53 (IMX25) primary antibody (Vector Laboratories, 1:1000). Expression of C/EBPα was analyzed in NIH3T3-C/EBPα-Hyg fibroblasts, which stably express C/EBPα and a hygromycin resistance gene. We used full protein and a rabbit polyclonal IgG anti-mouse C/EBPα primary antibody (Santa Cruz Biotechnology, 1:1000). Expression of Bcl2 in shRNA-infected NIH3T3s was analyzed using full protein and a mouse IgG1 anti-mouse/rat Bcl-2 (BCL/10C4) primary antibody (BioLegend, 1:1000). Loading control blots were performed using a mouse anti-mouse α-tubulin (B-5-1-2) antibody (Sigma, 1:5000) and a mouse monoclonal IgG1 isotype anti-β-actin (AC-15) antibody (Sigma, 1:5000). Secondary antibodies were: ECL anti-rabbit IgG horseradish peroxidase linked whole antibody from donkey (GE Healthcare UK), ECL anti-mouse IgG horseradish peroxidase linked whole antibody from sheep (GE Healthcare UK), and ECL anti-rat IgG horseradish peroxidase linked whole antibody from goat (GE Healthcare UK).

We claim:

1. A single construct comprising:
   a first sequence comprising a first promoter and
   a sequence encoding an shRNA molecule, operably linked to the first promoter, wherein the shRNA molecule comprises a guide strand; and
   a second sequence comprising a second promoter and
   a target sensor, operably linked to the second promoter, the target sensor comprising: a sequence encoding a reporter and a target sequence that is co-transcribed with the sequence encoding the reporter, and the target sequence comprises from about 8 to about 29 contiguous nucleotides complementary to at least a portion of the guide strand of the shRNA molecule, such that the functional shRNA molecule is specific for the target sequence and is capable of suppressing reporter expression.

2. The construct of claim 1, wherein the first promoter is an inducible promoter and the second promoter is a constitutive promoter.

3. The construct of claim 2, wherein the first promoter is a TRE promoter.

4. The construct of claim 1, wherein the first promoter or the second promoter or both promoters are ubiquitous.

5. The construct of claim 1, wherein the first promoter or the second promoter or both promoters are cell-type specific or tissue specific.

6. The construct of claim 1, wherein the single construct is capable of single-copy genomic integration.

7. The construct of claim 1, wherein the reporter is a fluorescent protein.

8. The construct of claim 1, further comprising a sequence encoding an additional reporter, operably linked to the first promoter.

9. The construct of claim 8, wherein the sequence encoding the additional reporter is a selection gene.

10. The construction of claim 1, wherein the target sequence is located in an untranslated region of the sequence encoding the reporter.

11. The construct of claim 1, wherein the target sequence comprises from about 16 to about 29 contiguous nucleotides complementary to at least a portion of the guide strand of the shRNA molecule.

12. The construct of claim 1, wherein the target sequence comprises from about 19 to about 22 contiguous nucleotides complementary to at least a portion of the guide strand of the shRNA molecule.

13. The construct of claim 1, wherein the target sequence is completely complementary to at least a portion of the guide strand of the shRNA molecule.

14. A single construct comprising:
   (i) a viral 5'LTR;
   (ii) a viral packaging signal;
   (iii) a first sequence comprising a first promoter and a sequence encoding an shRNA molecule, operably linked to the first promoter, wherein the shRNA molecule comprises a guide strand;
   (iv) a second sequence comprising a second promoter and a target sensor, operably linked to the second promoter, the target sensor comprising: a sequence encoding a reporter and a target sequence that is co-transcribed with the sequence encoding the reporter, and the target sequence comprises from about 8 to about 29 contiguous nucleotides complementary to at least a portion of the guide strand of the shRNA molecule, such that the functional shRNA molecule is specific for the target sequence and is capable of suppressing reporter expression; and
   (v) a viral 3'LTR.

15. The construct of claim 14, wherein the viral 5'LTR, the viral packaging signal, and the viral 3'LTR are from a retrovirus, a baculovirus, or an avian virus.

16. The construct of claim 15, wherein the retrovirus is a lentivirus.

17. The construct of claim 14, wherein the first promoter is an inducible promoter and the second promoter is a constitutive promoter.

18. The construct of claim 17, wherein the first promoter is a TRE promoter.

19. The construct of claim 17, wherein the 3'LTR is self-inactivating.

20. The construct of claim 14, wherein the first promoter or the second promoter or both promoters are ubiquitous.

21. The construct of claim 14, wherein the first promoter or the second promoter or both promoters are cell-type specific or tissue specific.

22. The construct of claim 14, wherein the single construct is capable of single-copy genomic integration.

23. The construct of claim 14, wherein the reporter is a fluorescent protein.

24. The construct of claim 14, further comprising a sequence encoding an additional reporter, operably linked to the first promoter.

25. The construct of claim 24, wherein the sequence encoding the additional reporter is a selection gene.

26. The construct of claim 14, wherein the target sequence is located in an untranslated region of the sequence encoding the reporter.

27. The construct of claim 14, wherein the target sequence comprises from about 16 to about 29 contiguous nucleotides complementary to at least a portion of the guide strand of the shRNA molecule.

28. The construct of claim 14, wherein the target sequence comprises from about 19 to about 22 contiguous nucleotides complementary to at least a portion of the guide strand of the shRNA molecule.

29. The construct of claim 14, wherein the target sequence is completely complementary to at least a portion of the guide strand of the shRNA molecule.

30. An shRNA library comprising a plurality of the construct of claim 1, wherein the sequence encoding the shRNA molecule is different in each construct.

31. An shRNA library comprising a plurality of the construct of claim 14, wherein the sequence encoding the shRNA molecule is different in each construct.

32. The shRNA library of claim 30 or claim 31, wherein the shRNA library is a tiled library.

33. A method for determining potency of an shRNA molecule, the method comprising:
    (a) introducing the construct of claim 1 into a cell; and
    (b) determining the amount of reporter expression in the cell, wherein high reporter expression indicates a less potent shRNA molecule and low or no reporter expression indicates a more potent shRNA molecule.

34. A method for determining potency of shRNA molecules, the method comprising:
    (a) introducing the shRNA library of claim 30 into cells; and
    (b) determining the amount of reporter expression in the cells, wherein high reporter expression indicates less potent shRNA molecules and low or no reporter expression indicates more potent shRNA molecules.

35. A method for determining potency of an shRNA molecule, the method comprising:
    (a) introducing the construct of claim 14 into a first cell, wherein the construct is packaged into a virion in the first cell;
    (b) infecting a second cell with the virion;
    (c) determining the amount of reporter expression in the cell, wherein high reporter expression indicates a less potent shRNA molecule and low or no reporter expression indicates a more potent shRNA molecule.

36. A method for determining potency of shRNA molecules, the method comprising:
    (a) introducing the shRNA library of claim 31 into a first population of cells, wherein the constructs of the RNAi library are packaged into virions in the first population of cells;
    (b) infecting a second population of cells with the virions;
    (c) determining the amount of reporter expression in the cells, wherein high reporter expression indicates less potent shRNA molecules and low or no reporter expression indicates more potent shRNA molecules.

* * * * *

SEQUENCE LISTING

<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tggtctgcca gctaaaggtg aagatatatt cctcc                             35

```
<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
accaagtcct tcgaggacat ccatcagtac agggagcaga tcaagcgggt gaaagattca          60

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gccagctaaa ggtgaagata ta                                                  22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccagctaaag gtgaagatat at                                                  22
```